(12) United States Patent
Hughes et al.

(10) Patent No.: US 8,816,088 B2
(45) Date of Patent: *Aug. 26, 2014

(54) DIAMIDE COMPOUNDS HAVING MUSCARINIC RECEPTOR ANTAGONIST AND β₂ ADRENERGIC RECEPTOR AGONIST ACTIVITY

(71) Applicant: Theravance, Inc., South San Francisco, CA (US)

(72) Inventors: Adam D. Hughes, Belmont, CA (US); Yan Chen, Foster City, CA (US); John R. Jacobsen, San Mateo, CA (US); Eric L. Stangeland, Pacifica, CA (US); Rose Yen, San Francisco, CA (US)

(73) Assignee: Theravance Respiratory Company, LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/964,484

(22) Filed: Aug. 12, 2013

(65) Prior Publication Data

US 2013/0331364 A1 Dec. 12, 2013

Related U.S. Application Data

(60) Continuation of application No. 13/369,109, filed on Feb. 8, 2012, now Pat. No. 8,551,978, which is a division of application No. 12/761,532, filed on Apr. 16, 2010, now Pat. No. 8,138,345.

(60) Provisional application No. 61/172,039, filed on Apr. 23, 2009.

(51) Int. Cl.
*C07D 401/12* (2006.01)
*C07D 401/00* (2006.01)

(52) U.S. Cl.
USPC .................................................... 546/157

(58) Field of Classification Search
None
See application file for complete search history.

(56) References Cited

U.S. PATENT DOCUMENTS

| | | |
|---|---|---|
| 7,141,671 B2 | 11/2006 | Mammen et al. |
| 7,320,990 B2 | 1/2008 | Chao et al. |
| 7,345,175 B2 | 3/2008 | Mammen et al. |
| 7,355,046 B2 | 4/2008 | Mammen et al. |
| 7,507,751 B2 | 3/2009 | Mammen et al. |
| 7,514,558 B2 | 4/2009 | Mammen et al. |
| 7,521,558 B2 | 4/2009 | Chao et al. |
| 7,521,561 B2 | 4/2009 | Mammen et al. |
| 7,524,959 B2 | 4/2009 | Mammen et al. |
| 7,524,965 B2 | 4/2009 | Colson et al. |
| 7,528,253 B2 | 5/2009 | Mammen et al. |
| 7,569,586 B2 | 8/2009 | Mammen et al. |
| 7,687,521 B2 | 3/2010 | Colson et al. |
| 7,829,583 B2 | 11/2010 | Mammen et al. |
| 7,879,879 B2 | 2/2011 | Mammen et al. |
| 7,880,010 B2 | 2/2011 | Bolton et al. |
| 8,101,766 B2 | 1/2012 | Chao et al. |
| 8,134,006 B2 | 3/2012 | Colson et al. |
| 8,143,277 B2 | 3/2012 | Mammen et al. |
| 2004/0167167 A1 | 8/2004 | Mammen et al. |
| 2004/0209860 A1 | 10/2004 | Mammen et al. |
| 2004/0209915 A1 | 10/2004 | Mammen et al. |
| 2006/0035931 A1 | 2/2006 | Chao et al. |
| 2007/0208176 A1 | 9/2007 | Mammen et al. |
| 2009/0182010 A1 | 7/2009 | Mammen et al. |

FOREIGN PATENT DOCUMENTS

| | | |
|---|---|---|
| WO | 2006/023454 A1 | 3/2006 |
| WO | 2007/090859 A1 | 8/2007 |
| WO | 2010/011314 A1 | 1/2010 |

OTHER PUBLICATIONS

International Search Report for PCT/US2010/031356 dated Jul. 8, 2010.
Final Office Action for U.S. Appl. No. 12/761,532 dated May 9, 2011.
Ray et al., "Muscarinic antagonist-beta-adrenergic agonist dual pharmacology molecules as bronchodilators: a patent review", Expert Opin. Ther. Patents (2009) 19(1):1-12.
Silverman, Richard B., The Organic Chemistry of Drug Design and Drug Action, Academic Press (1992).

*Primary Examiner* — Janet L Andres
*Assistant Examiner* — Timothy R Rozof
(74) *Attorney, Agent, or Firm* — Jeffrey A. Hagenah

(57) ABSTRACT

This invention relates to a compound of formula I:

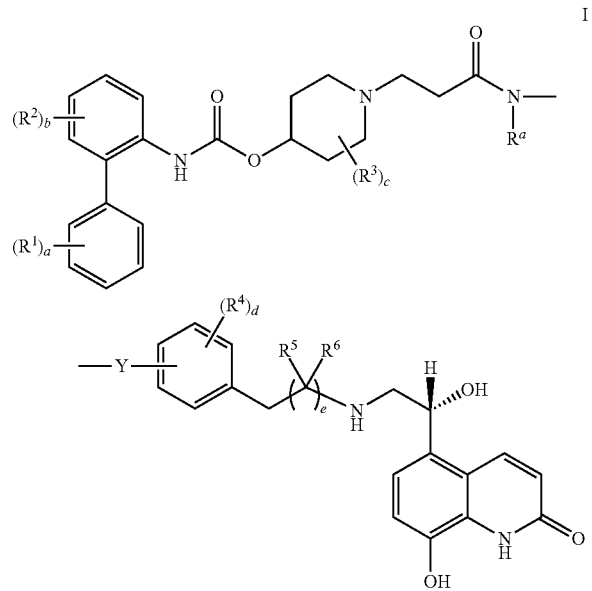

or a pharmaceutically acceptable salt thereof. Such compounds possess both muscarinic receptor antagonist and β₂ adrenergic receptor agonist activities. The invention also relates to pharmaceutical compositions comprising such compounds, processes and intermediates for preparing such compounds, and methods of using such compounds as bronchodilating agents to treat pulmonary disorders.

1 Claim, No Drawings

DIAMIDE COMPOUNDS HAVING MUSCARINIC RECEPTOR ANTAGONIST AND $\beta_2$ ADRENERGIC RECEPTOR AGONIST ACTIVITY

CROSS-REFERENCE TO RELATED APPLICATIONS

This application is a continuation of U.S. application Ser. No. 13/369,109, filed Feb. 8, 2012 (now U.S. Pat. No. 8,551,978 B2); which application is a divisional of U.S. application Ser. No. 12/761,532, filed Apr. 16, 2010 (now U.S. Pat. No. 8,138,345 B2); which application claims the benefit of U.S. Provisional Application No. 61/172,039, filed on Apr. 23, 2009; the entire disclosures of which are incorporated herein by reference in their entirety.

BACKGROUND OF THE INVENTION

1. Field of the Invention

This invention relates to novel diamide compounds having muscarinic receptor antagonist and $\beta_2$ adrenergic receptor agonist activity. The invention also relates to pharmaceutical compositions comprising such compounds, processes and intermediates for preparing such compounds, and methods of using such compounds as bronchodilating agents to treat pulmonary disorders.

2. State of the Art

Pulmonary disorders, such as chronic obstructive pulmonary disease (COPD) and asthma, are commonly treated with bronchodilators. See, for example, Ziedalski et al., *Advances in the Management of Chronic Obstructive Pulmonary Disease*, Expert Opin. Pharmacother., (2003) 4(7), 1063-1082; Tashkin et al., *The Role of Long-Acting Bronchodilators in the Management of Stable COPD*, Chest, 2004: 125; 249-259; and Donohue, *Therapeutic Responses in Asthma and COPD: Bronchodilators*, Chest, 2004: 126; 125-137. Such bronchodilators are typically administered by inhalation using a hand-held inhaler device.

Commonly-used bronchodilating agents typically have muscarinic receptor antagonist activity (i.e., anticholinergic agents) or $\beta_2$ adrenergic receptor (adrenoceptor) agonist activity. More recently, compounds having both muscarinic receptor antagonist and $\beta_2$ adrenergic receptor agonist (MABA) activities in the same molecule have been reported. For example, U.S. Pat. No. 7,141,671, issued Nov. 28, 2006, discloses biphenyl compounds having both muscarinic receptor antagonist and $\beta_2$ adrenergic receptor agonist activities.

Dual-acting MABA compounds are expected to be particularly useful for treating pulmonary disorders because such compounds can be formulated and administered as a single therapeutic agent but, once administered, they provide bronchodilation through two distinct, and possibly synergistic, modes of action. Additionally, MABA compounds have the potential to be combined with an anti-inflammatory agent, such as an inhaled corticosteroid (ICS), to provide triple therapy in a single inhaler using only two therapeutic agents (MABA+ICS).

Thus, a need exists for new MABA compounds. In particular, a need exists for new MABA compounds that are highly effective as both a muscarinic receptor antagonist and a $\beta_2$ adrenergic receptor agonist. Additionally, MABA compounds having a long duration of action, i.e., compounds that provide significant bronchodilation for at least about 24 hours after administration by inhalation, may be particularly useful for treating certain pulmonary disorders where once-daily administration of a bronchodilating agent is desired.

SUMMARY OF THE INVENTION

This invention relates to novel diamide compounds having both muscarinic receptor antagonist and $\beta_2$ adrenergic receptor agonist activities. Such compounds produce bronchodilation when administered to a mammal by inhalation. In some cases, compounds of this invention have been found to possess a long duration of action, i.e., to produce bronchodilation for at least about 24 hours after administration. Accordingly, compounds of this invention are expected to be useful and advantageous as bronchodilating agents for treating pulmonary disorders.

In one aspect, this invention relates to a compound of formula I:

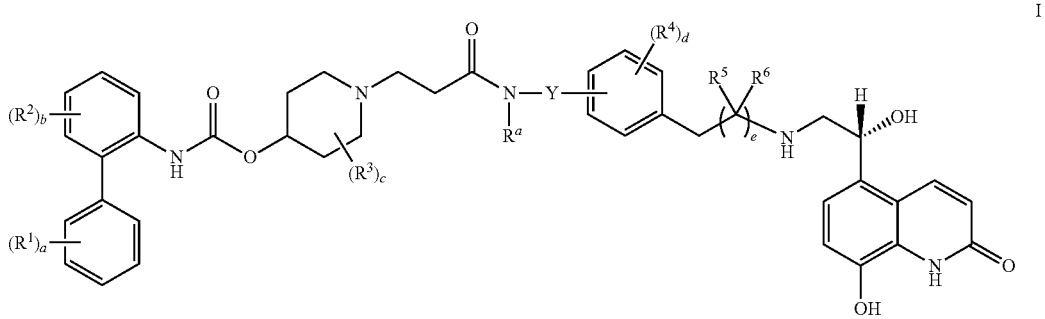

wherein
Y is a group of formula (a):

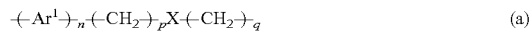

and Y is attached at the 3- or 4-position of the phenylene ring relative to the —$CH_2$—($CR^5R^6$)$_e$— group;

X is selected from —C(O)NH— and —NHC(O)—;

$Ar^1$ is selected from phen-1,3-ylene and phen-1,4-ylene, wherein the phenylene group is unsubstituted or substituted with 1 to 3 substituents selected independently from $C_{1-3}$ alkyl, —O—($C_{1-3}$ alkyl) and halo;

each $R^1$ is selected independently from $C_{1-3}$ alkyl, —O—($C_{1-3}$ alkyl), hydroxyl and halo;

each $R^2$ is selected independently from $C_{1-3}$ alkyl, —O—($C_{1-3}$ alkyl) and halo;

each $R^3$ is selected independently from $C_{1-3}$ alkyl; or two $R^3$ groups are joined to form $C_{1-3}$ alkylene, $C_{2-3}$ alkenylene or oxiran-2,3-diyl;

each $R^4$ is selected independently from $C_{1-3}$ alkyl, —O—($C_{1-3}$ alkyl) and halo;
$R^5$ is selected from hydrogen, methyl and ethyl;
$R^6$ is selected from hydrogen, methyl and ethyl;
$R^a$ is selected from $C_{1-6}$ alkyl;
a is 0, 1, 2 or 3;
b is 0, 1, 2 or 3;
c is 0, 1, 2, 3 or 4;
d is 0, 1, 2 or 3;
e is 0 or 1;
n is 0 or 1;
p is 0, 1, 2, 3, 4, 5 or 6; provided that when n is 0, p is 1, 2, 3, 4, 5 or 6;
q is 0, 1, 2, 3, 4, 5 or 6;
or a pharmaceutically acceptable salt thereof.

As used hereinafter, the phrase "compound of formula I" means a compound of formula I or a pharmaceutically acceptable salt thereof; i.e., this phrase means a compound of formula I in free base form or in a pharmaceutically acceptable salt form unless otherwise indicated.

In another aspect, this invention relates to a pharmaceutical composition comprising (a) a compound of formula I; (b) a pharmaceutically acceptable carrier. This aspect of the invention includes, for example, pharmaceutical compositions suitable for administration by inhalation.

In yet another aspect, this invention relates to a composition comprising (a) a compound of formula I, and (b) a steroidal anti-inflammatory agent (e.g., a corticosteroid). The term "steroidal anti-inflammatory agent" as used herein includes pharmaceutically acceptable salts and/or solvates of such agents unless otherwise indicated. This invention also relates to a pharmaceutical composition comprising (a) a compound of formula I; (b) a steroidal anti-inflammatory agent; and (c) a pharmaceutically acceptable carrier. These aspects of the invention include, for example, compositions suitable for administration by inhalation. In a particular embodiment, the steroidal anti-inflammatory agent is a corticosteroid (e.g., a glucocorticoid), such as fluticasone propionate or a solvate thereof or fluticasone furoate or a solvate thereof.

In still another aspect, this invention relates to a method for treating a pulmonary disorder in a patient comprising administering a compound of formula I to the patient. This aspect of the invention includes, for example, treating chronic obstructive pulmonary disease or asthma. Also included are methods in which a steroidal anti-inflammatory agent is administered simultaneously or sequentially with compound of formula I to treat a pulmonary disorder.

In another aspect, this invention relates to a method for producing bronchodilation in a mammal comprising administering a bronchodilation-producing amount of a compound of formula I to the mammal. This aspect includes, for example, producing bronchodilation in a human.

In yet another aspect, this invention relates to a method for antagonizing a muscarinic receptor and agonizing a $\beta_2$ adrenergic receptor in a biological system or sample comprising a muscarinic receptor and a $\beta_2$ adrenergic receptor, the method comprising treating the biological system or sample with a compound of formula I. This aspect includes both in vivo and in vitro methods.

This invention also relates to processes and novel intermediates useful for preparing compounds of formula I. In one such embodiment, this invention relates to a compound of formula 3a:

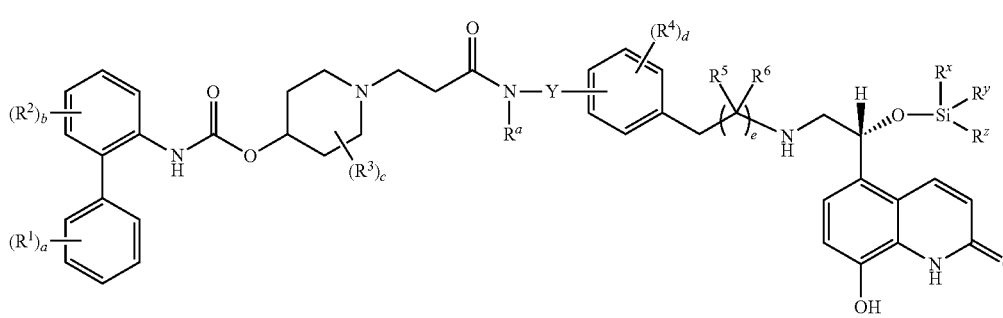

3a or a salt thereof, wherein $R^x$ and $R^y$ are independently selected from $C_{1-4}$ alkyl, phenyl, and —$C_{1-4}$ alkyl-(phenyl); and le is selected from $C_{1-4}$ alkyl, phenyl, —$C_{1-4}$ alkyl-(phenyl) and —O—($C_{1-4}$ alkyl).

In yet another of its method aspects, this invention relates to a process of preparing a compound of formula I, the process comprising deprotecting a compound of formula 3a to provide a compound of formula I.

Other aspects and embodiments of this invention are described herein.

DETAILED DESCRIPTION OF THE INVENTION

In one of its composition aspects, this invention relates to compounds of formula I. Such compounds contain one or more chiral centers and therefore, such compounds (and intermediates thereof) can exist as racemic mixtures; pure stereoisomers (i.e., enantiomers or diastereomers); stereoisomer-enriched mixtures and the like. Chiral compounds shown or named herein without a defined stereochemistry at a chiral center are intended to include any or all possible stereoisomer variations at the undefined stereocenter unless otherwise indicated. The depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

Compounds of formula I also contain several basic groups (e.g., amino groups) and therefore, such compounds can exist as the free base or in various salt forms, such a mono-protonated salt form or a di-protonated salt form or mixtures thereof. All such forms are included within the scope of this invention, unless otherwise indicated.

This invention also includes isotopically-labeled compounds of formula I, i.e., compounds of formula I where an atom has been replaced or enriched with an atom having the same atomic number but an atomic mass different from the atomic mass that predominates in nature. Examples of isotopes that may be incorporated into a compound of formula I include, but are not limited to $^2$H, $^3$H, $^{11}$C, $^{13}$C, $^{14}$C, $^{13}$N, $^{15}$N, $^{15}$O, $^{17}$O, $^{18}$O, $^{35}$S, $^{36}$Cl, and $^{18}$F. Of particular interest are compounds of formula I enriched in tritium or carbon-14, which compounds can be used, for example, in tissue distribution studies. Also of particular interest are compounds of formula I enriched in deuterium especially at a site of metabolism, which compounds are expected to have greater metabolic stability. Also of particular interest are compounds of formula I enriched in a positron emitting isotope, such as $^{11}$C, $^{18}$F, $^{15}$O and $^{13}$N, which compounds can be used, for example, in Positron Emission Tomography (PET) studies.

Additionally, where applicable, all cis-trans or E/Z isomers (geometric isomers), tautomeric forms and topoisomeric forms of the compounds of the invention are included within the scope of the invention, unless otherwise specified.

The compounds described herein have typically been named using the AutoNom feature of the commercially-available MDL® ISIS/Draw software (Symyx, Santa Clara, Calif.).

Representative Embodiments

The following substituents and values are intended to provide representative examples of various aspects and embodiments of this invention. These representative values are intended to further define and illustrate such aspects and embodiments and are not intended to exclude other embodiments or to limit the scope of this invention. In this regard, the representation that a particular value or substituent is preferred is not intended in any way to exclude other values or substituents from this invention unless specifically indicated.

In one embodiment, n is 0, and Ar$^1$ is absent. In another embodiment, n is 1, and Ar$^1$ is present.

When present, in one embodiment, Ar$^1$ is unsubstituted phen-1,3-ylene. In another embodiment, Ar$^1$ is phen-1,3-ylene substituted with 1 to 3 substituents selected independently from C$_{1-3}$ alkyl, —O—(C$_{1-3}$ alkyl) and halo. In another embodiment, Ar$^1$ is phen-1,3-ylene substituted with 1 or 2 substituents selected independently from methyl, ethyl, methoxy, fluoro or chloro. Representative examples of Ar$^1$ include, but are not limited to, phen-1,3-ylene, 2-methylphen-1,3-ylene, 4-methylphen-1,3-ylene, 5-methylphen-1,3-ylene, 6-methylphen-1,3-ylene, 2-methoxyphen-1,3-ylene, 4-methoxyphen-1,3-ylene, 5-methoxyphen-1,3-ylene, 6-methoxyphen-1,3-ylene, 2-fluorophen-1,3-ylene, 4-fluorophen-1,3-ylene, 5-fluorophen-1,3-ylene, 6-fluorophen-1,3-ylene, 2-chlorophen-1,3-ylene, 4-chlorophen-1,3-ylene, 5-chlorophen-1,3-ylene, 6-chlorophen-1,3-ylene, 2,4-dimethylphen-1,3-ylene, 2,5-dimethylphen-1,3-ylene, 2,6-dimethylphen-1,3-ylene, 4,6-dimethylphen-1,3-ylene, 2-chloro-5-methoxyphen-1,3-ylene, and 5-chloro-2-methoxyphen-1,3-ylene. In a particular embodiment, Ar$^1$ is phen-1,3-ylene or 6-methylphen-1,3-ylene.

In another embodiment, Ar$^1$ is unsubstituted phen-1,4-ylene. In yet another embodiment, Ar$^1$ is phen-1,4-ylene substituted with 1 to 3 substituents selected independently from C$_{1-3}$ alkyl, —O—(C$_{1-3}$ alkyl) and halo. In another embodiment, Ar$^1$ is phen-1,4-ylene substituted with 1 or 2 substituents selected independently from methyl, ethyl, methoxy, fluoro or chloro. Representative examples of Ar$^1$ include, but are not limited to, phen-1,4-ylene, 2-methylphen-1,4-ylene, 3-methylphen-1,4-ylene, 5-methylphen-1,4-ylene, 6-methylphen-1,4-ylene, 2-methoxyphen-1,4-ylene, 3-methoxyphen-1,4-ylene, 5-methoxyphen-1,4-ylene, 6-methoxyphen-1,4-ylene, 2-fluorophen-1,4-ylene, 3-fluorophen-1,4-ylene, 5-fluorophen-1,4-ylene, 6-fluorophen-1,4-ylene, 2-chlorophen-1,4-ylene, 3-chlorophen-1,4-ylene, 5-chlorophen-1,4-ylene, 6-chlorophen-1,4-ylene, 2,3-dimethylphen-1,4-ylene, 2,5-dimethylphen-1,4-ylene, 2,6-dimethylphen-1,4-ylene, 3,5-dimethylphen-1,4-ylene, 2-chloro-5-methoxyphen-1,4-ylene, and 5-chloro-2-methoxyphen-1,4-ylene.

In a particular embodiment, Ar$^1$ is phen-1,3-ylene, phen-1,4-ylene or 6-methylphen-1,3-ylene.

In separate embodiments, p is 0, 1, 2, 3, 4, 5 or 6; provided that p cannot be 0 when n is 0. Additionally, in one embodiment, when n is 0 and X is —NHC(O)—, then p is typically not 1. Representative —(CH$_2$)$_p$— groups include —CH$_2$—, —(CH$_2$)$_2$—, —(CH$_2$)$_3$—, —(CH$_2$)$_4$—, —(CH$_2$)$_5$—, and —(CH$_2$)$_6$—. In a particular embodiment, p is 0, 1, 2, 3, or 4.

In separate embodiments, q is 0, 1, 2, 3, 4, 5 or 6. Representative —(CH$_2$)$_q$— groups include —CH$_2$—, —(CH$_2$)$_2$—, —(CH$_2$)$_3$—, —(CH$_2$)$_4$—, —(CH$_2$)$_5$—, and —(CH$_2$)$_6$—. In a particular embodiment, q is 0, 1 or 2.

In one embodiment, X is —C(O)NH—. In another embodiment, X is —NHC(O)—.

In a particular embodiment, Y forms a group of the formula: —(CH$_2$)$_p$—X—(CH$_2$)$_q$—, where X, p and q are as defined herein. Representative examples include:
 —(CH$_2$)$_p$—C(O)NH—(CH$_2$)$_q$—; and
 —(CH$_2$)$_p$—NHC(O)—(CH$_2$)$_q$—.

In another particular embodiment, Y forms a group of the formula: —(CH$_2$)$_p$—X—, where X and p are as defined herein. Representative examples include:
 —(CH$_2$)$_p$—C(O)NH—; and
 —(CH$_2$)$_p$—NHC(O)—.

In another particular embodiment, Y forms a group of the formula: —Ar$^1$—(CH$_2$)$_p$—X—(CH$_2$)$_q$—, where Ar$^1$, X, p and q are as defined herein. Representative examples include:
 -(phen-1,3-ylene)-(CH$_2$)$_p$—C(O)NH—(CH$_2$)$_q$—;
 -(phen-1,3-ylene)-(CH$_2$)$_p$—NHC(O)—(CH$_2$)$_q$—;
 -(phen-1,4-ylene)-(CH$_2$)$_p$—C(O)NH—(CH$_2$)$_q$—; and
 -(phen-1,4-ylene)-(CH$_2$)$_p$—NHC(O)—(CH$_2$)$_q$—;
where the phen-1,3-ylene or phen-1,4-ylene group is unsubstituted or substituted as defined herein.

In another particular embodiment, Y forms a group of the formula: —Ar$^1$—(CH$_2$)$_p$—X—, where Ar$^1$, X and p are as defined herein. Representative examples include:
 -(phen-1,3-ylene)-(CH$_2$)$_p$—C(O)NH—;
 -(phen-1,3-ylene)-(CH$_2$)$_p$—NHC(O)—;
 -(phen-1,4-ylene)-(CH$_2$)$_p$—C(O)NH—; and
 -(phen-1,4-ylene)-(CH$_2$)$_p$—NHC(O)—;
where the phen-1,3-ylene or phen-1,4-ylene group is unsubstituted or substituted as defined herein.

In another particular embodiment, Y forms a group of the formula: —Ar$^1$—X—(CH$_2$)$_q$—, where Ar$^1$, X and q are as defined herein. Representative examples include:
 -(phen-1,3-ylene)-C(O)NH—(CH$_2$)$_q$—;
 -(phen-1,3-ylene)-NHC(O)—(CH$_2$)$_q$—;
 -(phen-1,4-ylene)-C(O)NH—(CH$_2$)$_q$—; and
 -(phen-1,4-ylene)-NHC(O)—(CH$_2$)$_q$—;
where the phen-1,3-ylene or phen-1,4-ylene group is unsubstituted or substituted as defined herein.

In another particular embodiment, Y forms a group of the formula: —Ar$^1$—X—, where Ar$^1$ and X are as defined herein. Representative examples include:
 -(phen-1,3-ylene)-C(O)NH—;
 -(phen-1,3-ylene)-NHC(O)—;
 -(phen-1,4-ylene)-C(O)NH—; and
 -(phen-1,4-ylene)-NHC(O)—;
where the phen-1,3-ylene or phen-1,4-ylene group is unsubstituted or substituted as defined herein.

In one embodiment, Y is attached at the 3-position of the phenylene ring relative to the —$CH_2$—$(CR^5R^6)_e$— group. In another embodiment, Y is attached at the 4-position of the phenylene ring relative to the —$CH_2$—$(CR^5R^6)_e$— group.

In one embodiment, a is 0, and $R^1$ is absent. In other separate embodiments, a is 1, 2 or 3, i.e., one, two or three $R^1$ groups are present at any available position of the phenyl ring to which $R^1$ is attached. For example, when a is 1, $R^1$ can be at the 2-, 3-, 4-, 5- or 6-position of the phenyl ring to which $R^1$ is attached; when a is 2, $R^1$ groups can be at the 2,3-, 2,4-, 2,5-, 2,6-, 3,4-, or 3,5-positions of the phenyl ring to which $R^1$ is attached; and when a is 3, $R^1$ groups can be at the 2,3,4-, 2,3,5-, 2,3,6-, 2,4,5-, 2,4,6-, or 3,4,5-positions of the phenyl ring to which $R^1$ is attached.

When present, in one embodiment, each $R^1$ is selected independently from $C_{1-3}$ alkyl, —O—($C_{1-3}$ alkyl), hydroxyl and halo. In another embodiment, each $R^1$ is selected independently from $C_{1-3}$ alkyl, —O—($C_{1-3}$ alkyl), and halo. In another embodiment, each le is selected independently from methyl, ethyl, methoxy, fluoro, chloro and bromo.

In one embodiment, b is 0, and $R^2$ is absent. In other separate embodiments, b is 1, 2 or 3, i.e., one, two or three $R^2$ groups are present at any available position of the phenylene ring to which $R^2$ is attached. For example, when b is 1, an $R^2$ group can be at the 3-, 4-, 5- or 6-position of the phen-1,2-ylene ring to which $R^2$ is attached; when b is 2, $R^2$ groups can be at the 3,4-, 3,5-, 3,6-, 4,5-, 4,6-, or 5,6-positions of the phen-1,2-ylene ring to which $R^2$ is attached; and when b is 3, $R^2$ groups can be at the 3,4,5-, 3,4,6-, or 4,5,6-positions of the phen-1,2-ylene ring to which $R^2$ is attached.

When present, in one embodiment, each $R^2$ is selected independently from $C_{1-3}$ alkyl, —O—($C_{1-3}$ alkyl), and halo. In another embodiment, each $R^2$ is selected independently from halo. In another embodiment, each $R^2$ is selected independently from methyl, ethyl, methoxy, fluoro, chloro and bromo.

In one embodiment, c is 0, and $R^3$ is absent. In other separate embodiments, c is 1, 2, 3 or 4, i.e., one, two, three or four $R^3$ groups are present at any available position of the piperidin-1,4-yl ring to which $R^3$ is attached.

When present, in one embodiment, each $R^3$ is selected independently from $C_{1-3}$ alkyl. In another embodiment, each $R^3$ is methyl. Representative $R^3$ groups include methyl, ethyl, n-propyl and isopropyl.

In another embodiment, two $R^3$ groups are joined to form $C_{1-3}$ alkylene or $C_{2-3}$ alkenylene or oxiran-2,3-diyl. Representative groups include —$CH_2$—, —$CH_2CH_2$—, —CH=CH—, —$CH_2CH_2CH_2$—, and —$CH_2CH$=CH—. For example, two $R^3$ groups at the 2- and 6-positions on the piperidine ring can be joined to form an ethylene bridge (i.e., the piperidine ring and the $R^3$ groups form an 8-azabicyclo[3.2.1]octane ring); or two $R^3$ groups at the 1- and 4-positions on the piperidine ring can be joined to form an ethylene bridge (i.e., the piperidine ring and the $R^3$ groups form an 1-azabicyclo[2.2.2]octane ring); or two $R^3$ groups at the 2- and 6-positions on the piperidine ring can be joined to form an ethenylene bridge (i.e., the piperidine ring and the $R^3$ groups form an 8-azabicyclo[3.2.1]oct-6-ene ring). In this embodiment, other $R^3$ groups as defined herein may also be present.

In still another embodiment, two $R^3$ groups are joined to form an oxiran-2,3-diyl group. For example, two $R^3$ groups at the 2- and 6-positions on the piperidine ring can be joined to form a 3-oxatricyclo[3.3.1.0$^{2,4}$]nonane ring. In this embodiment, other $R^3$ groups as defined herein may also be present.

In one embodiment, d is 0, and $R^4$ is absent.

In other separate embodiments, d is 1, 2, or 3, i.e., one, two or three $R^4$ groups may be attached at any available position of the phenylene ring to which $R^4$ is attached. For example, when d is 1 and Y is attached at the 3-position of the phenylene ring, an $R^4$ group can be at the 2-, 4-, 5- or 6-position of the phen-1,3-ylene ring to which $R^4$ is attached. When d is 1 and Y is attached at the 4-position of the phenylene ring, an $R^4$ group can be at, for example, the 2-, 3-, 5- or 6-position of the phen-1,4-ylene ring to which $R^4$ is attached.

When d is 2 and Y is attached at the 3-position of the phenylene ring, $R^4$ groups can be at, for example, the 2,4-, 2,5-, 2,6-, 4,5-, 4,6-, or 5,6-positions of the phen-1,3-ylene ring to which $R^4$ is attached. When d is 2 and Y is attached at the 4-position of the phenylene ring, $R^4$ groups can be at, for example, the 2,3-, 2,5-, 2,6-, 3,5-, 3,6-, or 5,6-positions of the phen-1,4-ylene ring to which $R^4$ is attached.

When d is 3 and Y is attached at the 3-position of the phenylene ring, $R^4$ groups can be at, for example, the 2,4,5-, 2,4,6-, 2,5,6-, or 4,5,6-positions of the phenylene ring to which $R^4$ is attached. When d is 3 and Y is attached at the 4-position of the phenylene ring, $R^4$ groups can be at, for example, the 2,3,5-, 2,3,6-, 2,5,6-, or 3,5,6-positions of the phenylene ring to which $R^4$ is attached.

When present, in one embodiment, each $R^4$ is selected independently from $C_{1-3}$ alkyl, —O—($C_{1-3}$ alkyl), and halo. In another embodiment, each $R^4$ is selected independently from methyl, ethyl, methoxy, fluoro, chloro and bromo. In a particular embodiment, $R^4$ is selected from methyl, methoxy, chloro and fluoro. In another particular embodiment, d is 2, and each $R^4$ is methyl. In yet another particular embodiment, d is 2, and one $R^4$ is methoxy, and the other $R^4$ is chloro.

In one embodiment, e is 0, and —$CR^5R^6$— is absent. In another embodiment, e is 1.

When present, in one embodiment, $R^5$ is hydrogen. In another embodiment, $R^5$ is methyl. In still another embodiment, $R^5$ is ethyl.

When present, in one embodiment, $R^6$ is hydrogen. In another embodiment, $R^6$ is methyl. In still another embodiment, $R^6$ is ethyl. In a particular embodiment, $R^6$ is hydrogen, and $R^5$ is hydrogen or methyl. In another particular embodiment, $R^5$ and $R^6$ are both methyl.

When $R^5 \neq R^6$, the carbon to which $R^5$ and $R^6$ are attached is chiral. In one embodiment, this stereocenter has the (R)-configuration. In another embodiment, this stereocenter has the (S)-configuration. In particular embodiments, the group —$CH_2$—$(CR^5R^6)_e$— is selected from —$CH_2$—, —$CH_2CH_2$—, —$CH_2C$*$H(CH_3)$—, where C* has the (R) configuration, the (S) configuration or is racemic.

In one embodiment, $R^a$ is selected from $C_{1-6}$ alkyl. In another embodiment, $R^a$ is $C_{1-4}$ alkyl. In still another embodiment, $R^a$ is $C_{1-3}$ alkyl. Representative $R^a$ groups include methyl, ethyl, n-propyl, isopropyl, n-butyl, sec-butyl, isobutyl, tert-butyl, n-pentyl and n-hexyl. In a particular embodiment, $R^a$ is methyl.

In one embodiment, the compound of formula I is a free base. In another embodiment, the compound of formula I is a mono-salt form. In yet another embodiment, the compound of formula I is a di-salt form.

Representative Sub Generic Groupings

The following subgeneric formulae and groupings are intended to provide representative examples of various aspects and embodiments of this invention and as such, they are not intended to exclude other embodiments or to limit the scope of the embodiments or the invention, unless otherwise indicated.

A particular embodiment of this invention relates to a compound of formula Ia:

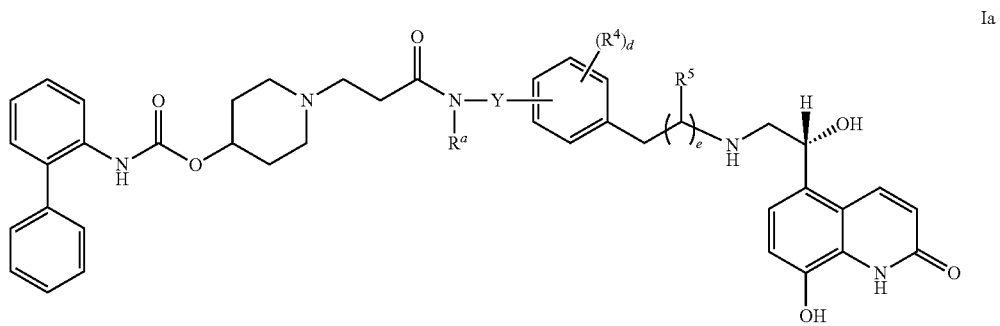

i.e., a compound of formula I wherein a, b and c are 0 (i.e., $R^1$, $R^2$ and $R^3$ are absent), $R^6$ is hydrogen, and $R^4$, $R^5$, $R^a$, Y, d and e are as defined herein, or a pharmaceutically acceptable salt thereof.

Another particular embodiment relates to a compound of formula Ib:

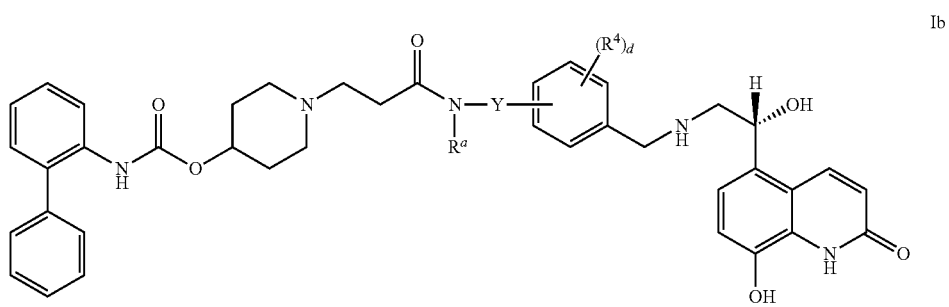

i.e., a compound of formula I wherein a, b, c and e are 0 (i.e., $R^1$, $R^2$, $R^3$ and $CR^5R^6$ are absent), and $R^4$, $R^a$, Y and d are as defined herein, or a pharmaceutically acceptable salt thereof.

Another particular embodiment relates to a compound of formula Ic:

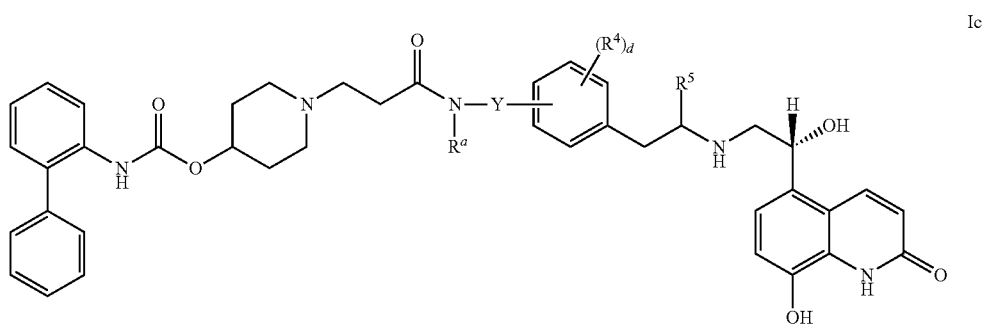

i.e., a compound of formula I wherein a, b and c are 0 (i.e., $R^1$, $R^2$ and $R^3$ are absent), $R^6$ is hydrogen, e is 1, and $R^4$, $R^5$, $R^a$, Y and d are as defined herein, or a pharmaceutically acceptable salt thereof.

Another particular embodiment relates to a compound of formula II:

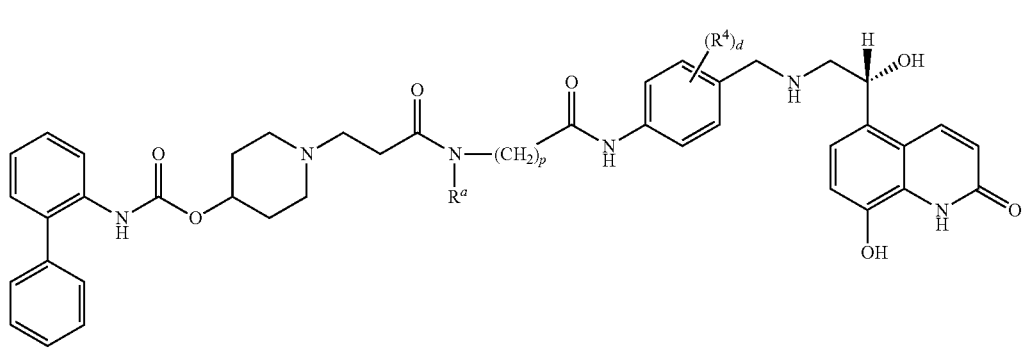

i.e., a compound of formula I wherein a, b, c and e are 0 (i.e., $R^1$, $R^2$, $R^3$ and $CR^5R^6$ are absent), Y forms a group of the formula: —$(CH_2)_p$—C(O)NH—, and $R^4$, $R^a$, d and p are as defined herein, or a pharmaceutically acceptable salt thereof.

In a particular embodiment of compounds of formula II, $R^a$ is methyl; p is 3 or 4; and d is 0, 1 or 2; and each $R^4$ is selected independently from methyl; methoxy, chloro and fluoro.

In another particular embodiment of compounds of formula II, $R^a$ is methyl; p is 4; and d is 0, 1 or 2; and each $R^4$ is selected independently from methyl; methoxy, chloro and fluoro. As shown in Table III, all compounds of this embodiment tested in the rat Einthoven assay (100 μg) exhibited a bronchoprotective effect at 24 h.

Another particular embodiment relates to a compound of formula III:

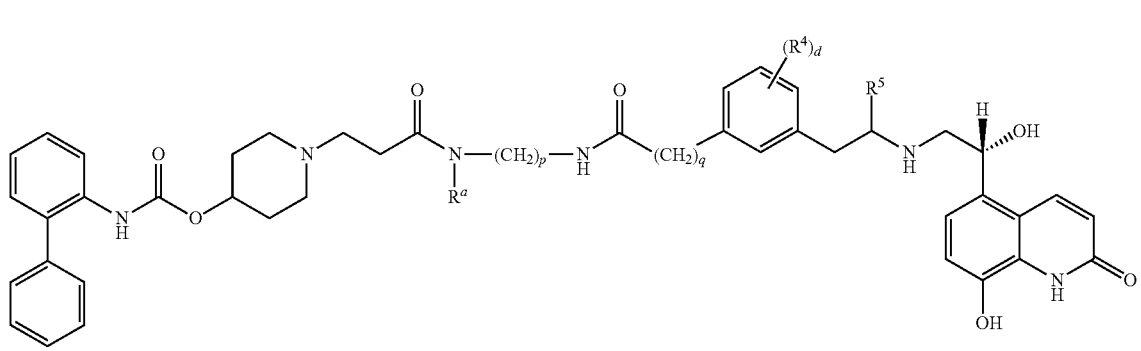

i.e., a compound of formula I wherein a, b and c are 0 (i.e., $R^1$, $R^2$ and $R^3$ are absent), $R^6$ is hydrogen, e is 1, Y forms a group of the formula: —$(CH_2)_p$—NHC(O)—$(CH_2)_q$— and $R^4$, $R^5$, $R^a$, d, p and q are as defined herein, or a pharmaceutically acceptable salt thereof.

In a particular embodiment of compounds of formula III, $R^a$ is methyl; p is 3 or 4; q is 1; $R^5$ is methyl; and d is 0.

In another embodiment, this invention relates to a compound of formula IV:

IV

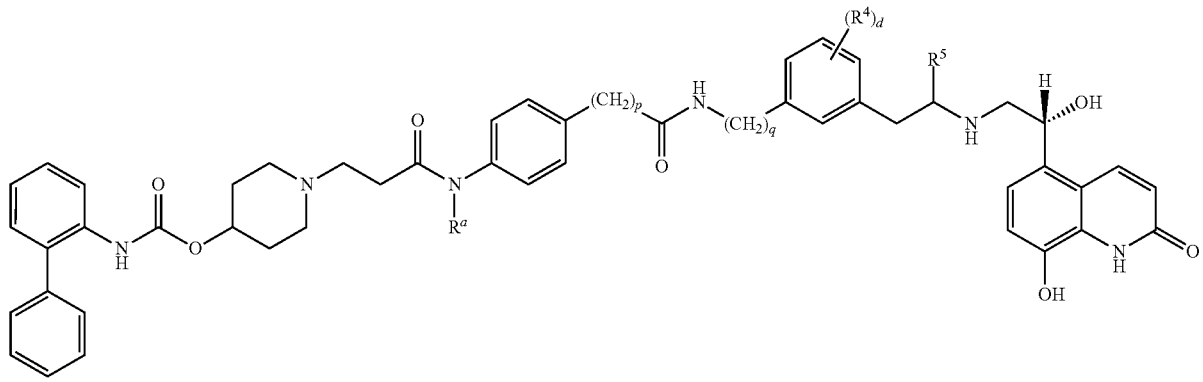

i.e., a compound of formula I wherein a, b and c are 0 (i.e., $R^1$, $R^2$ and $R^3$ are absent), $R^6$ is hydrogen, e is 1, Y forms a group of the formula: —$Ar^1$—$(CH_2)_p$—C(O)NH—$(CH_2)_q$—, $Ar^1$ is phenyl-1,4-ene, and $R^4$, $R^5$, $R^a$, d, p and q are as defined herein, or a pharmaceutically acceptable salt thereof.

In a particular embodiment of compounds of formula IV, $R^a$ is methyl; p is 1; q is 1 or 2; $R^5$ is hydrogen or methyl; d is 0 or 1; and $R^4$ is selected from methyl; methoxy, and fluoro.

In another embodiment, this invention relates to a compound of formula V:

V

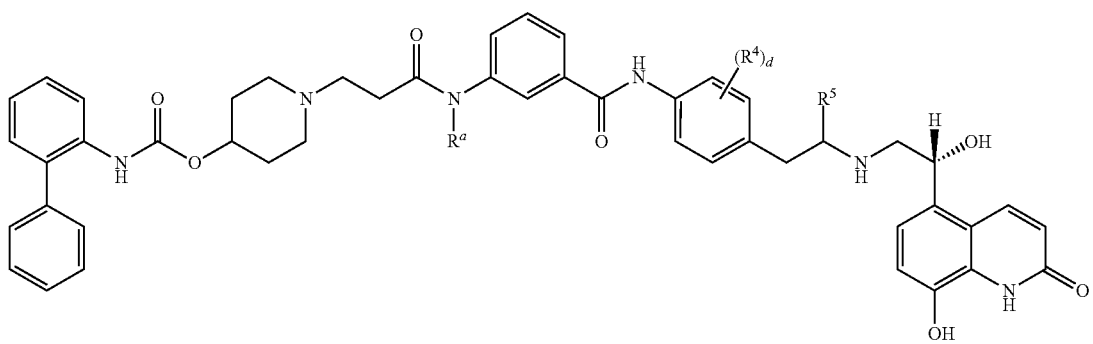

i.e., a compound of formula I wherein a, b and c are 0 (i.e., $R^1$, $R^2$ and $R^3$ are absent), $R^6$ is hydrogen, e is 1, Y forms a group of the formula: —$Ar^1$—C(O)NH—, $Ar^1$ is phenyl-1,3-ene, and $R^4$, $R^5$, $R^a$, and d are as defined herein, or a pharmaceutically acceptable salt thereof.

In a particular embodiment of compounds of formula V, $R^a$ is methyl; $R^5$ is hydrogen or methyl; d is 0, 1 or 2; and each $R^4$ is selected independently from methyl; methoxy, chloro and fluoro.

Particular embodiments of compounds of formula I are compounds where a, b and c are 0 (i.e., $R^1$, $R^2$ and $R^3$ are absent), $R^a$ is methyl; and $(Ar^1)_n$, $(CH_2)_p$, X, $(CH_2)_q$, $(R^4)_d$ (and the phenylene ring to which it is attached), and —$CH_2(CR^5R^6)_e$— are as defined in Table I:

TABLE I

| ID | $(Ar^1)_n$ | $(CH_2)_p$ | X | $(CH_2)_q$ | ($R^4)_d$ phenyl | $R^5 R^6$ / e |
|---|---|---|---|---|---|---|
| I-1 | — | $(CH_2)_3$ | C(O)NH | — | 1,4-phenyl | $CH_2$ |

TABLE I-continued

| ID | (Ar¹)ₙ | (CH₂)ₚ | X | (CH₂)q | ![aryl with (R⁴)d] | ![alkyl with R⁵ R⁶] |
|---|---|---|---|---|---|---|
| I-2 | — | (CH₂)₃ | C(O)NH | — | 2-methyl-1,4-phenylene (H₃C on ring) | CH₂ |
| I-3 | — | (CH₂)₃ | C(O)NH | — | 2-methoxy-1,4-phenylene (H₃C—O on ring) | CH₂ |
| I-4 | — | (CH₂)₃ | C(O)NH | — | 3-methoxy-1,4-phenylene (O—CH₃ on ring) | CH₂ |
| I-5 | — | (CH₂)₃ | C(O)NH | — | 2,5-dimethyl-1,4-phenylene (H₃C, CH₃ on ring) | CH₂ |
| I-6 | — | (CH₂)₃ | C(O)NH | — | 2-chloro-5-methoxy-1,4-phenylene (Cl, O—CH₃ on ring) | CH₂ |
| I-7 | — | (CH₂)₃ | C(O)NH | — | 1,3-phenylene | (CH₂)₂ |
| I-8 | — | (CH₂)₃ | C(O)NH | — | 1,4-phenylene | (CH₂)₂ |
| I-9 | — | (CH₂)₃ | C(O)NH | — | 2-methoxy-1,4-phenylene | (CH₂)₂ |
| I-10 | — | (CH₂)₃ | C(O)NH | — | 1,3-phenylene | CH₂CH(CH₃) |

TABLE I-continued

| ID | (Ar¹)ₙ | (CH₂)ₚ | X | (CH₂)q | Ar² (with (R⁴)d) | R⁵R⁶ chain |
|---|---|---|---|---|---|---|
| I-11 | — | (CH₂)₃ | NHC(O) | CH₂ | 1,3-phenylene | isobutyl (CH₃ branch) |
| I-12 | — | (CH₂)₃ | NHC(O) | CH₂ | 1,3-phenylene | (S)-sec-butyl (H, CH₃) |
| I-13 | — | (CH₂)₃ | NHC(O) | CH₂ | 1,3-phenylene | (R)-sec-butyl (H₃C, H) |
| I-14 | — | (CH₂)₄ | C(O)NH | — | 1,4-phenylene | CH₂ |
| I-15 | — | (CH₂)₄ | C(O)NH | — | 2-methyl-1,4-phenylene (H₃C) | CH₂ |
| I-16 | — | (CH₂)₄ | C(O)NH | — | 2-methoxy-1,4-phenylene (H₃C—O) | CH₂ |
| I-17 | — | (CH₂)₄ | C(O)NH | — | 3-methoxy-1,4-phenylene (O—CH₃) | CH₂ |
| I-18 | — | (CH₂)₄ | C(O)NH | — | 2,5-dimethyl-1,4-phenylene (H₃C, CH₃) | CH₂ |
| I-19 | — | (CH₂)₄ | C(O)NH | — | 2-chloro-5-methoxy-1,4-phenylene (Cl, O—CH₃) | CH₂ |

TABLE I-continued
| ID | $(Ar^1)_n$ | $(CH_2)_p$ | X | $(CH_2)_q$ | 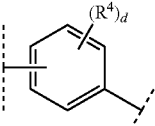 | 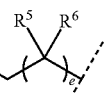 |
|---|---|---|---|---|---|---|
| I-20 | — | $(CH_2)_4$ | C(O)NH | — | 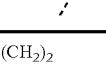 | $(CH_2)_2$ |
| I-21 | — | $(CH_2)_4$ | C(O)NH | — | 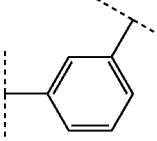 | $(CH_2)_2$ |
| I-22 | — | $(CH_2)_4$ | NHC(O) | $CH_2$ | 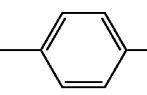 | 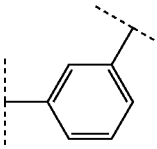 |
| I-23 | — | $(CH_2)_4$ | NHC(O) | $CH_2$ | 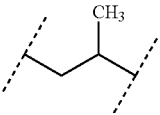 | 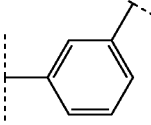 |
| I-24 | — | $(CH_2)_4$ | NHC(O) | $CH_2$ | 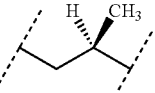 | 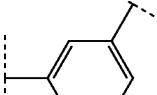 |
| I-25 | 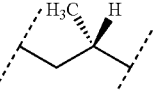 | — | C(O)NH | — | 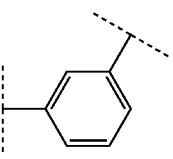 | $CH_2$ |
| I-26 | 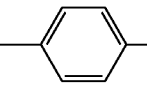 | — | C(O)NH | — | 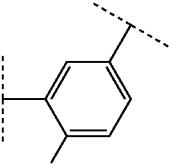 | $CH_2$ |
| I-27 | 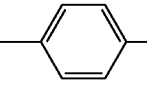 | — | C(O)NH | — | 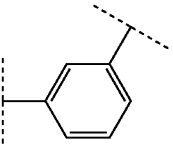 | $CH_2$ |
| I-28 | 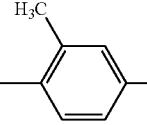 | — | C(O)NH | — | 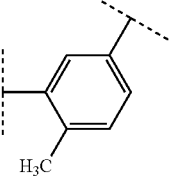 | $CH_2$ |

TABLE I-continued

| ID | (Ar¹)ₙ | (CH₂)ₚ | X | (CH₂)_q | ![(R⁴)_d aryl] | ![R⁵ R⁶ chain] |
|---|---|---|---|---|---|---|
| I-29 | *meta-phenyl* | — | C(O)NH | — | 2-OMe-phenyl (1,4-linked) | CH₂ |
| I-30 | *meta-phenyl* | — | C(O)NH | — | 2,5-dimethyl-phenyl (1,4-linked) | CH₂ |
| I-31 | *meta-phenyl* | — | C(O)NH | — | 2-Cl-5-OMe-phenyl (1,4-linked) | CH₂ |
| I-32 | *meta-phenyl* | — | C(O)NH | — | *meta-phenyl* | (CH₂)₂ |
| I-33 | 4-methyl-phenyl (1,3-linked) | — | C(O)NH | — | *meta-phenyl* | (CH₂)₂ |
| I-34 | *meta-phenyl* | — | C(O)NH | — | *para-phenyl* | (CH₂)₂ |
| I-35 | 4-methyl-phenyl (1,3-linked) | — | C(O)NH | — | *para-phenyl* | (CH₂)₂ |
| I-36 | *meta-phenyl* | — | C(O)NH | — | *meta-phenyl* | CH₂CH(CH₃) |

TABLE I-continued
| ID | $(Ar^1)_n$ | $(CH_2)_p$ | X | $(CH_2)_q$ | 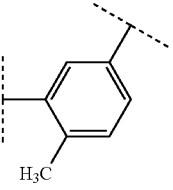 | 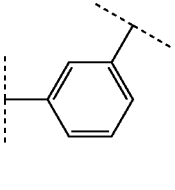 |
|---|---|---|---|---|---|---|
| I-37 | 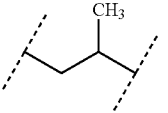 | — | C(O)NH | — | 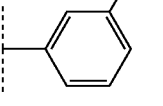 | 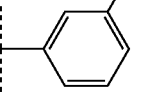 |
| I-38 | 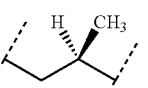 | — | C(O)NH | — | 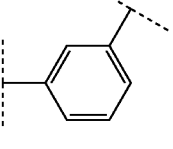 | 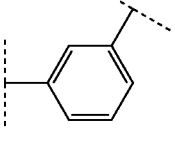 |
| I-39 | 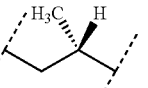 | — | C(O)NH | — | 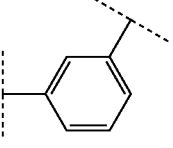 | 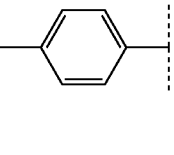 |
| I-40 | 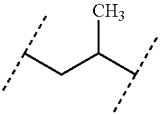 | — | C(O)NH | — | 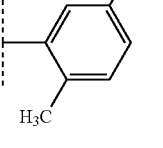 | 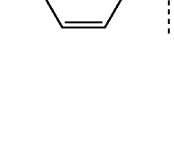 |
| I-41 | 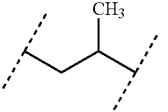 | — | C(O)NH | — | 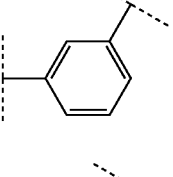 | 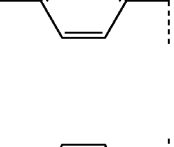 |
| I-42 | 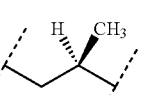 | — | C(O)NH | — | 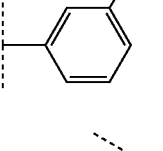 | 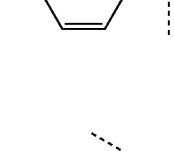 |
| I-43 | 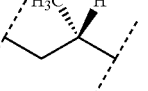 | — | C(O)NH | — | 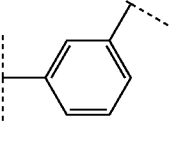 | 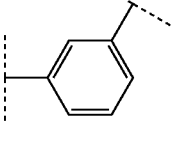 |
| I-44 | 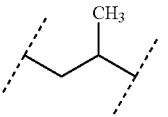 | — | C(O)NH | $CH_2$ | | |

TABLE I-continued
| ID | $(Ar^1)_n$ | $(CH_2)_p$ | X | $(CH_2)_q$ | 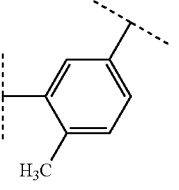 | 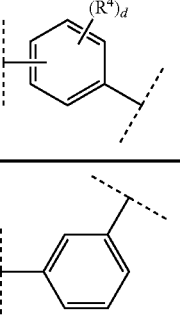 |
|---|---|---|---|---|---|---|
| I-45 | 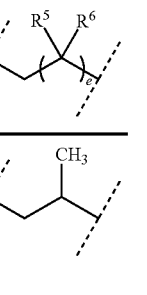 | — | C(O)NH | CH$_2$ | 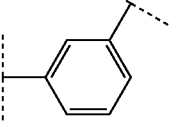 | 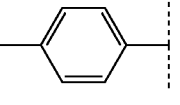 |
| I-46 | 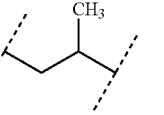 | — | C(O)NH | CH$_2$ | 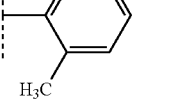 | 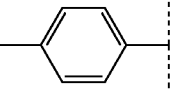 |
| I-47 | 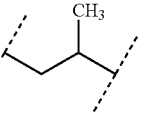 | — | C(O)NH | CH$_2$ | 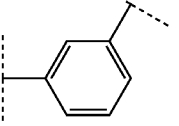 | 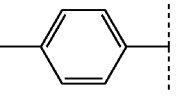 |
| I-48 | 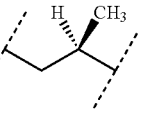 | — | C(O)NH | CH$_2$ | 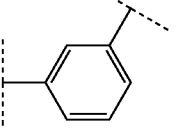 | 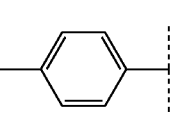 |
| I-49 | 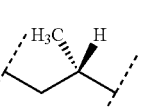 | — | C(O)NH | CH$_2$ | 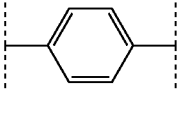 | 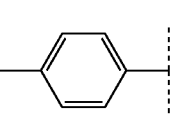 |
| I-50 | 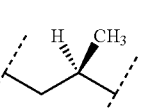 | — | C(O)NH | CH$_2$ | 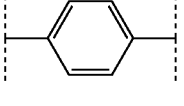 | 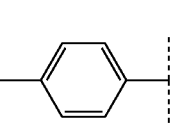 |
| I-51 | 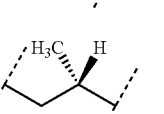 | — | C(O)NH | CH$_2$ | 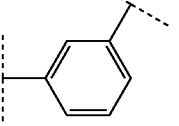 | 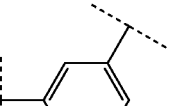 |
| I-52 | 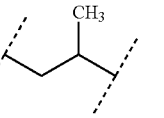 | — | NHC(O) | CH$_2$ | 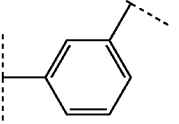 | 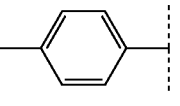 |
| I-53 | 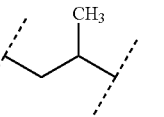 | — | NHC(O) | CH$_2$ | | |

TABLE I-continued

| ID | $(Ar^1)_n$ | $(CH_2)_p$ | X | $(CH_2)_q$ | phenyl with $(R^4)_d$ | $R^5, R^6$ chain (length $e$) |
|---|---|---|---|---|---|---|
| I-54 | 3-phenylene | — | NHC(O) | $CH_2$ | 4-methoxyphenyl (2-substituted) | $CH_2CH(CH_3)$– |
| I-55 | 1,4-phenylene | — | C(O)NH | $(CH_2)_2$ | 3-phenylene | $CH_2C^*H(CH_3)$– (H wedge) |
| I-56 | 1,4-phenylene | — | C(O)NH | $(CH_2)_2$ | 3-phenylene | $CH_2C^*H(CH_3)$– ($H_3C$ wedge) |
| I-57 | 1,4-phenylene | — | C(O)NH | $(CH_2)_2$ | 1,4-phenylene | $CH_2C^*H(CH_3)$– (H wedge) |
| I-58 | 1,4-phenylene | — | C(O)NH | $(CH_2)_2$ | 1,4-phenylene | $CH_2C^*H(CH_3)$– ($H_3C$ wedge) |
| I-59 | 3-phenylene | $CH_2$ | C(O)NH | — | 1,4-phenylene | $CH_2$ |
| I-60 | 3-phenylene | $CH_2$ | C(O)NH | — | 2,5-dimethyl-1,4-phenylene | $CH_2$ |
| I-61 | 3-phenylene | $CH_2$ | C(O)NH | — | 2-chloro-5-methoxy-1,4-phenylene | $CH_2$ |
| I-62 | 3-phenylene | $CH_2$ | C(O)NH | — | 3-phenylene | $(CH_2)_2$ |

TABLE I-continued

| ID | (Ar¹)ₙ | (CH₂)ₚ | X | (CH₂)_q | aryl (R⁴)_d | R⁵ R⁶ (CH)_e |
|---|---|---|---|---|---|---|
| I-63 | meta-phenylene | CH₂ | C(O)NH | — | para-phenylene | (CH₂)₂ |
| I-64 | para-phenylene | CH₂ | C(O)NH | CH₂ | para-phenylene | (CH₂)₂ |
| I-65 | para-phenylene | CH₂ | C(O)NH | CH₂ | meta-phenylene | (CH₂)₂ |
| I-66 | para-phenylene | CH₂ | C(O)NH | CH₂ | para-phenylene | CH₂CH(CH₃) |
| I-67 | para-phenylene | CH₂ | C(O)NH | CH₂ | meta-phenylene | CH₂CH(CH₃) |
| I-68 | para-phenylene | CH₂ | C(O)NH | CH₂ | meta-phenylene | CH₂C(H)(CH₃) |
| I-69 | para-phenylene | CH₂ | C(O)NH | CH₂ | meta-phenylene | CH₂C(CH₃)(H) |
| I-70 | para-phenylene | CH₂ | C(O)NH | CH₂ | 3,4-disubstituted 4-methylphenyl | CH₂CH(CH₃) |
| I-71 | para-phenylene | CH₂ | C(O)NH | CH₂ | 2-methyl-1,3-disubstituted phenyl | CH₂CH(CH₃) |

TABLE I-continued

| ID | $(Ar^1)_n$ | $(CH_2)_p$ | X | $(CH_2)_q$ | Ar² with $(R^4)_d$ | $R^5, R^6$ chain |
|---|---|---|---|---|---|---|
| I-72 | phenylene | CH₂ | C(O)NH | CH₂ | 2-methoxyphenyl | -CH₂-CH(CH₃)- |
| I-73 | phenylene | CH₂ | C(O)NH | CH₂ | 2-fluorophenyl | -CH₂-CH(CH₃)- |
| I-74 | phenylene | CH₂ | NHC(O) | CH₂ | 1,3-phenylene | CH₂ |
| I-75 | phenylene | CH₂ | NHC(O) | CH₂ | 1,4-phenylene | CH₂ |
| I-76 | phenylene | CH₂ | NHC(O) | CH₂ | 1,3-phenylene | (CH₂)₂ |
| I-77 | phenylene | CH₂ | NHC(O) | CH₂ | 1,3-phenylene | -CH₂-CH(CH₃)- |
| I-78 | phenylene | CH₂ | NHC(O) | CH₂ | 1,3-phenylene | -CH₂-C(H)(CH₃)- (S) |
| I-79 | phenylene | CH₂ | NHC(O) | CH₂ | 1,3-phenylene | -CH₂-C(H)(CH₃)- (R) |
| I-80 | phenylene | CH₂ | NHC(O) | CH₂ | 1,4-phenylene | -CH₂-CH(CH₃)- |

TABLE I-continued

| ID | (Ar¹)ₙ | (CH₂)ₚ | X | (CH₂)q | Ar²(R⁴)d | R⁵R⁶ chain |
|---|---|---|---|---|---|---|
| I-81 | 1,4-phenylene | CH₂ | NHC(O) | CH₂ | 4-methoxyphenyl (attached at 3-position) | isobutyl (CH₃ branch) |
| I-82 | 1,4-phenylene | CH₂ | NHC(O) | CH₂ | 4-methoxyphenyl (attached at 3-position) | (S)-sec-butyl-like (H, CH₃) |
| I-83 | 1,4-phenylene | CH₂ | NHC(O) | CH₂ | 4-methoxyphenyl (attached at 3-position) | (R)-sec-butyl-like (H₃C, H) |
| I-84 | 1,4-phenylene | CH₂ | NHC(O) | CH₂ | 4-fluorophenyl (attached at 3-position) | isobutyl (CH₃ branch) |
| I-85 | 1,4-phenylene | CH₂ | C(O)NH | (CH₂)₂ | 1,3-phenylene | isobutyl (CH₃ branch) |
| I-86 | 1,4-phenylene | CH₂ | C(O)NH | (CH₂)₂ | 1,3-phenylene | (H, CH₃) |
| I-87 | 1,4-phenylene | CH₂ | C(O)NH | (CH₂)₂ | 1,3-phenylene | (H₃C, H) |
| I-88 | 1,4-phenylene | CH₂ | C(O)NH | (CH₂)₂ | 1,4-phenylene | isobutyl (CH₃ branch) |
| I-89 | 1,4-phenylene | CH₂ | C(O)NH | (CH₂)₂ | 1,4-phenylene | (H₃C, H) |

TABLE I-continued

| ID | $(Ar^1)_n$ | $(CH_2)_p$ | X | $(CH_2)_q$ | Ar² with $(R^4)_d$ | $R^5, R^6$ chain |
|---|---|---|---|---|---|---|
| I-90 | 1,4-phenylene | $CH_2$ | $C(O)NH$ | $(CH_2)_2$ | 1,4-phenylene | $-CH_2-CH(H)(CH_3)-$ (stereo) |
| I-91 | 1,4-phenylene | $CH_2$ | $NHC(O)$ | $(CH_2)_2$ | 1,3-phenylene | $-CH_2-CH(CH_3)-$ |
| I-92 | 1,4-phenylene | $CH_2$ | $NHC(O)$ | $(CH_2)_2$ | 1,3-phenylene | $-CH_2-CH(H)(CH_3)-$ (stereo) |
| I-93 | 1,4-phenylene | $CH_2$ | $NHC(O)$ | $(CH_2)_2$ | 1,3-phenylene | $-CH_2-CH(H_3C)(H)-$ (stereo) |
| I-94 | 1,4-phenylene | $CH_2$ | $NHC(O)$ | $(CH_2)_2$ | 3-methoxy-1,4-phenylene ($H_3C-O$) | $-CH_2-CH(CH_3)-$ |
| I-95 | 1,4-phenylene | $CH_2$ | $NHC(O)$ | $(CH_2)_2$ | 4-fluoro-1,3-phenylene (F) | $-CH_2-CH(CH_3)-$ |
| I-96 | 1,4-phenylene | $(CH_2)_2$ | $NHC(O)$ | $CH_2$ | 1,3-phenylene | $CH_2$ |

The compounds listed in Table I may be in free base form or may be in a pharmaceutically acceptable salt form. Of particular interest are compounds of Table I that demonstrate a bronchoprotective effect 24 hours after administration by inhalation, e.g., as determined in the rat Einthoven Assay.

DEFINITIONS

When describing this invention including its various aspects and embodiments, the following terms have the following meanings unless otherwise indicated.

The singular terms "a," "an" and "the" include the corresponding plural terms unless the context of use clearly dictates otherwise.

The term "alkyl" means a monovalent saturated hydrocarbon group which may be linear or branched. Unless otherwise defined, such alkyl groups typically contain from 1 to 10 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

When a specific number of carbon atoms are intended for a particular term, the number of carbon atoms is shown preceding the term. For example, the term "$C_{1-3}$ alkyl" means an alkyl group having from 1 to 3 carbon atoms wherein the carbon atoms are in any chemically-acceptable configuration, including linear or branched configurations.

The term "alkylene" means a divalent saturated hydrocarbon group that may be linear or branched. Unless otherwise defined, such alkylene groups typically contain from 1 to 10 carbon atoms. Representative alkylene groups include, by way of example, methylene, ethane-1,2-diyl ("ethylene"), propane-1,2-diyl, propane-1,3-diyl, butane-1,4-diyl, pentane-1,5-diyl and the like.

The term "amino-protecting group" means a protecting group suitable for preventing undesired reactions at an amino group. Representative amino-protecting groups include, but are not limited to, tert-butoxycarbonyl (BOC), trityl (Tr), benzyloxycarbonyl (Cbz), 9-fluorenylmethoxycarbonyl (Fmoc), benzyl, formyl, trimethylsilyl (TMS), tert-butyldimethylsilyl (TBS), and the like.

The term "carboxyl-protecting group" means a protecting group suitable for preventing undesired reactions at a carboxyl group (i.e., —COOH). Representative carboxyl-protecting groups include, but are not limited to, esters, such as methyl, ethyl, tert-butyl, benzyl (Bn), p-methoxybenzyl (PMB), 9-fluorenylmethyl (Fm), trimethylsilyl (TMS), tert-butyldimethylsilyl (TBS, TBDMS), diphenylmethyl (benzhydryl, DPM) and the like.

The term "halo" means fluoro, chloro, bromo, and iodo.

The term "hydroxyl-protecting group" means a protecting group suitable for preventing undesirable reactions at a hydroxyl group. Representative hydroxyl-protecting groups include, but are not limited to, silyl groups including tri($C_{1-6}$ alkyl)silyl groups, such as trimethylsilyl (TMS), triethylsilyl (TES), tert-butyldimethylsilyl (TBS) and the like; esters (acyl groups) including $C_{1-6}$ alkanoyl groups, such as formyl, acetyl and the like; arylmethyl groups, such as benzyl (Bn), p-methoxybenzyl (PMB), 9-fluorenylmethyl (Fm), diphenylmethyl (benzhydryl, DPM) and the like. Additionally, two hydroxyl groups can also be protected as an alkylidene group, such as prop-2-ylidine, formed, for example, by reaction with a ketone, such as acetone.

The term "leaving group" means a functional group or an atom that can be displaced by another functional group or atom in a substitution reaction, such as a nucleophilic substitution reaction. By way of example, representative leaving groups include, but are not limited to, chloro, bromo and iodo groups; sulfonic ester groups, such as mesylate, tosylate, brosylate, nosylate and the like; and acyloxy groups, such as acetoxy, trifluoroacetoxy and the like.

The term "micronized" or "in micronized form" means particles in which at least about 90 percent of the particles have a diameter of less than about 10 μm unless otherwise indicated.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "protected derivatives thereof" means a derivative of the specified compound in which one or more functional groups of the compound are protected or blocked from undergoing undesired reactions with a protecting or blocking group. Functional groups that may be protected include, by way of example, carboxy groups, amino groups, hydroxyl groups, thiol groups, carbonyl groups and the like. Suitable protecting groups for such functional groups are well known to those of ordinary skill in the art as exemplified by the teachings in T. W. Greene and P. G. M. Wuts, *Protecting Groups in Organic Synthesis*, Third Edition, Wiley, New York, 1999, and the references cited therein.

The term "salt thereof" means a compound formed when the hydrogen of an acid is replaced by a cation, such as a metal cation or an organic cation and the like. For example, the cation can be a protonated form of a compound of formula I, i.e. where one or more amino groups having been protonated by an acid. Typically, the salt is a pharmaceutically acceptable salt, although this is not required for salts of intermediate compounds that are not intended for administration to a patient.

The term "solvate" means a complex or aggregate formed by one or more molecules of a solute, i.e. a compound of formula I or a pharmaceutically acceptable salt thereof, and one or more molecules of a solvent. Such solvates are typically crystalline solids having a substantially fixed molar ratio of solute and solvent. Representative solvents include, by way of example, water, methanol, ethanol, isopropanol, acetic acid and the like. When the solvent is water, the solvate formed is a hydrate.

The term "therapeutically effective amount" means an amount sufficient to effect treatment when administered to a patient in need of treatment.

The term "treating" or "treatment" as used herein means the treating or treatment of a disease or medical condition (such as COPD or asthma) in a patient, such as a mammal (e.g., a human), that includes any of the following or combinations thereof:
(a) preventing the disease or medical condition from occurring, i.e., prophylactic treatment of a patient;
(b) ameliorating the disease or medical condition, i.e., eliminating or causing regression of the disease or medical condition in a patient;
(c) suppressing the disease or medical condition, i.e., slowing or arresting the development of the disease or medical condition in a patient; or
(d) alleviating the symptoms of the disease or medical condition in a patient.

All other terms used herein are intended to have their ordinary meaning as understood by those of ordinary skill in the art to which they pertain.

General Synthetic Procedures

Compounds of this invention, and intermediates thereof, can be prepared according to the following general methods and procedures using commercially-available or routinely-prepared starting materials and reagents. The substituents and variables (e.g., $R^1$, $R^2$, Y, a, b, etc.) used in the following schemes have the same meanings as those defined elsewhere herein unless otherwise indicated. Additionally, compounds having an acidic or basic atom or functional group may be used or may be produced as a salt unless otherwise indicated (in some cases, the use of a salt in a particular reaction will require conversion of the salt to a non-salt form, e.g., a free base, using routine procedures before conducting the reaction).

Scheme 1 illustrates a typical procedure for preparing compounds of formula (where $R^6$ is hydrogen):

Scheme 1

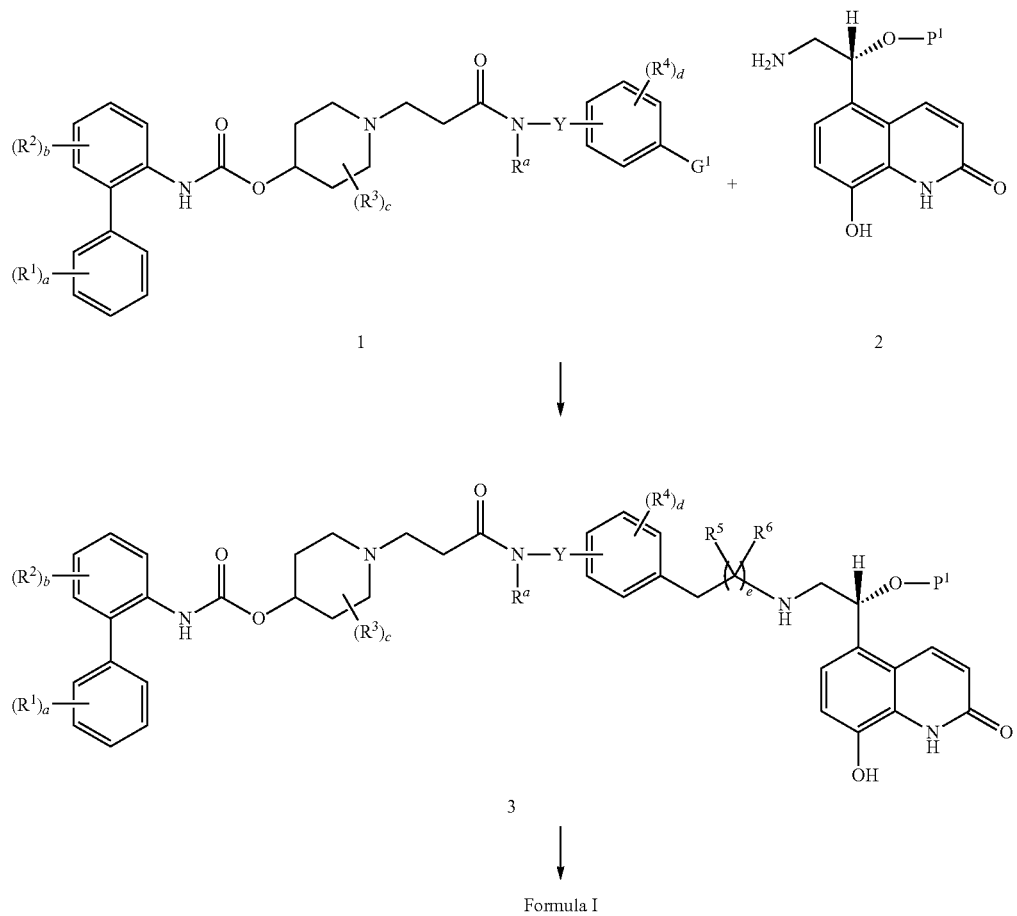

Formula I wherein
G¹ is —CHO or —CH₂C(O)R⁵; and
P¹ is a hydroxyl-protecting group, such as tert-butyldimethylsilyl.

In this procedure, compound 1 is reacted with about 0.95 to about 1.5 molar equivalents of compound 2 in the presence of a reducing agent to afford compound 3. Any suitable reducing agent may be used in this reaction including, by way of illustration, a metal hydride reagent, such as sodium borohydride, sodium triacetoxyborohydride, sodium cyanoborohydride and the like, or hydrogen and a metal catalyst, such as palladium on carbon, and the like. This reaction is typically conducted at a temperature ranging from about −20° C. to about 30° C. (e.g., about 0° C. to about 5° C.) for about 1 hour to about 6 hours or until the reaction is substantially complete. Typically, this reaction is conducted in a diluent, such as dichloromethane (DCM), dichloroethane and the like. Optionally, the diluent may contain a protic solvent, such as methanol and the like. Upon completion of the reaction, the product is typically isolated using conventional procedures, such as extraction, recrystallization, chromatography and the like. Alternatively, if desired, the reaction mixture containing compound 3 can be used directly in the next step of the synthesis without further isolation or purification.

Compound 3 is then deprotected to provide a compound of formula I. The particular conditions used to deprotect compound 3 will depend on the protecting group employed. For example, when P¹ is a silyl protecting group, such as tert-butyldimethylsilyl, tert-butyldiphenylsilyl, diphenylmethylsilyl, di-tert-butylmethylsilyl, tert-butoxydiphenylsilyl, and the like (i.e., a compound of formula 3a as defined herein), this deprotection reaction is typically conducted by contacting compound 3 with a source of fluoride ion. In a particular embodiment, the source of fluoride ion is triethylamine trihydrofluoride. Other suitable sources of fluoride ion include tetrabutylammonium fluoride, potassium fluoride with 18-crown-6, hydrogen fluoride, pyridine hydrofluoride, and the like. This reaction is typically conducted at a temperature ranging from about 0° C. to about 50° C., (e.g., about 10° C. to about 25° C.) for about 24 to about 72 hours or until the reaction is substantially complete. Typically, this reaction is conducted in a diluent, such as DCM, dichloroethane and the like. Upon completion of the reaction, the product is typically isolated using conventional procedures, such as extraction, recrystallization, chromatography and the like.

Compounds of formula 1 are typically prepared by deprotecting the corresponding acetal or ketal intermediate. For example, when G¹ is —CHO, compounds of formula 1 are typically prepared by deprotecting an intermediate of formula 4a:

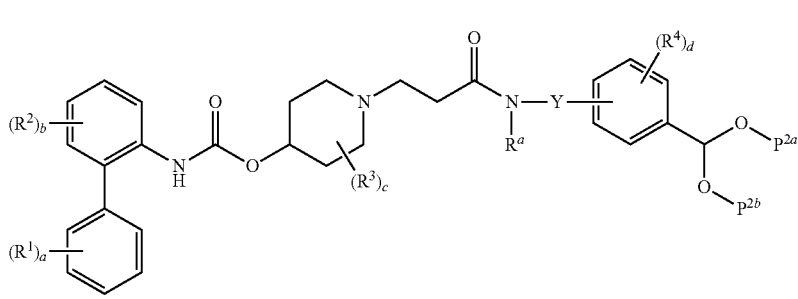

4a wherein $P^{2a}$ and $P^{2b}$ are selected independently from $C_{1-6}$ alkyl, or $P^{2a}$ and $P^{2b}$ are joined to form $C_{2-6}$ alkylene, typically $C_{2-4}$ alkylene.

Similarly, when $G^1$ is —$CH_2C(O)R^5$, compounds of formula 1 are typically prepared by deprotecting an intermediate of formula 4b:

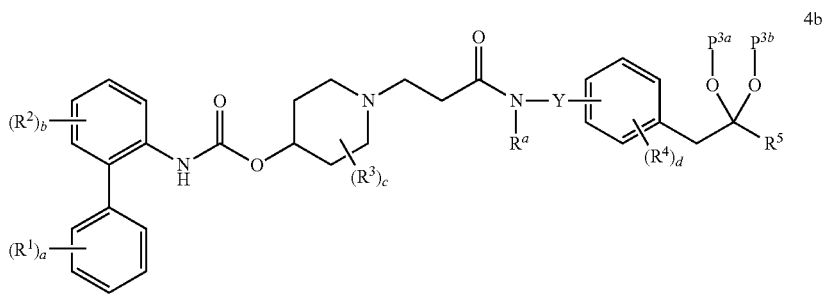

4b wherein $P^{3a}$ and $P^{3b}$ are selected independently from $C_{1-6}$ alkyl, or $P^{3a}$ and $P^{3b}$ are joined to form $C_{2-6}$ alkylene, typically $C_{2-4}$ alkylene.

Deprotection of compound 4a or 4b is typically conducted by reacting 4a or 4b with aqueous acid to hydrolyze the acetal or ketal group and provide the corresponding aldehyde or ketone compound 1. Any suitable acid can be employed in this reaction including, by way of example, hydrochloric acid, sulfuric acid, methanesulfonic acid, p-toluenesulfonic acid and the like. The hydrolysis reaction is typically conducted at a temperature ranging from about 0° C. to about 30° C. (e.g., about 20° C. to about 25° C.) for about 1 to about 6 hours or until the reaction is substantially complete. Typically, this reaction is conducted in a diluent, such as methanol, ethanol, isopropanol, dichloromethane/ethanol, acetonitrile and the like. Upon completion of the reaction, the product is typically isolated using conventional procedures, such as extraction, recrystallization, chromatography and the like. Alternatively, the reaction mixture containing compound 1 can be used directly in the next step of the synthesis.

Compounds of formula 4a or 4b are typically prepared by coupling a compound of formula 5:

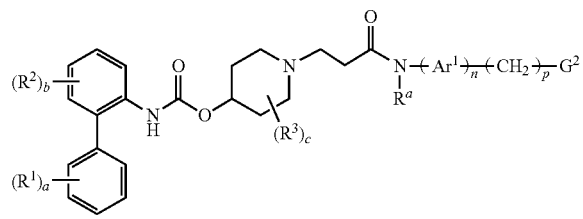

5 with a compound of formula 6a or 6b:

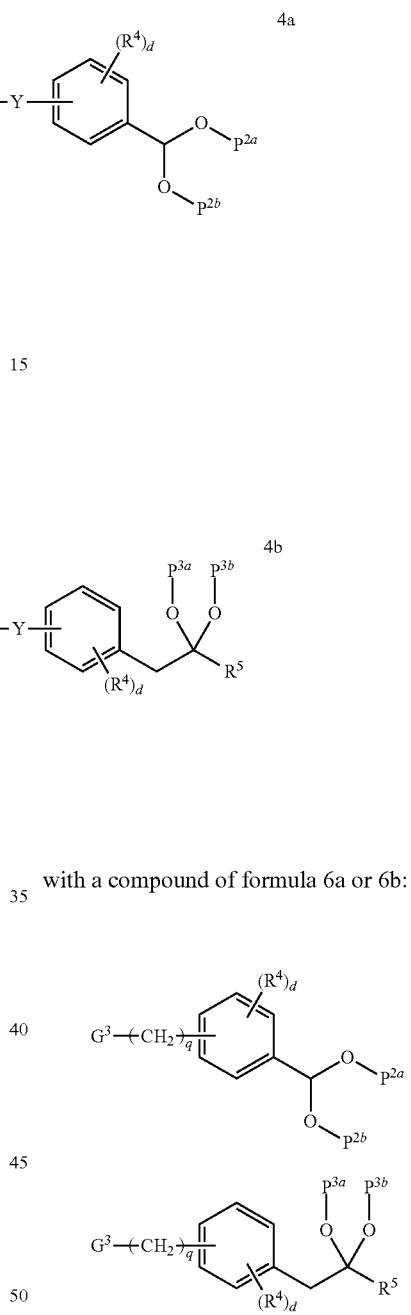

6a

6b wherein
$G^2$ is —$NH_2$ and $G^3$ is —COOH; or $G^2$ is —COOH and $G^3$ is —$NH_2$.

The coupling reaction between compound 5 and compound 6a or 6b to form compound 4a or 4b is typically conducted using a carboxylic acid-amine coupling reagent. Any suitable carboxylic acid-amine coupling reagent may be used in this reaction including, by way of illustration, benzotriazole-1-yl-oxy-tris-(dimethylamino)phosphonium hexafluorophosphate (BOP); N,N-carbonyldiimidazole (CDI); dicyclohexylcarbodiimide (DCC); 3-(diethoxyphosphoryloxy)-1,2,3-benzotriazin-4(3H)-one (DEPBT); 1-ethyl-3-(3-dimethyllaminopropyl)carbodiimide hydrochloride (EDC HCl); 2-(7-aza-1H-benzotriazole-1-yl)-1,1,3,3-tetramethyluronium hexafluorophosphate (HATU); 2-(1H- benzotriazole-1-yl)-1,1,3,3-tetramethyluronium hexafluorophosphate (HBTU); 2-(6-chloro-1H-benzotriazole-1-yl)-1,1,3,3-tetramethylaminium hexafluorophosphate (HCTU); 1-hydroxy-7-azabenzotriazole (HOAt); N-hydroxybenzotriazole (HOBt); benzotriazole-1-yl-oxy-tris-pyrrolidinophosphonium hexafluorophosphate (PyBOP); bromo-tris-pyrrolidinophosphonium hexafluorophosphate (PyBrOP); O-(7-azabenzotriazole-1-yl)-N,N,N',N'-tetramethyluronium tetrafluoroborate (TATU); 2-(1H-benzotriazole-1-yl)-1,1,3,3-tetramethyluronium tetrafluoroborate (TBTU); N,N,N',N'-tetramethyl-O-(3,4-dihydro-4-oxo-1,2,3-benzotriazin-3-yl)uranium tetrafluoroborate (TDBTU); O—(N-succinimidyl)-1,1,3,3-tetramethyl uranium tetrafluoroborate (TSTU); and combinations thereof, such as EDC and HOBt.

The coupling reaction is typically conducted by reacting about 0.95 to about 1.5 molar equivalents of the amine compound (5, when $G^2$ is —NH$_2$; or 6a or 6b when $G^3$ is —NH$_2$) with the carboxylic acid (5, when $G^2$ is —COOH; or 6a or 6b when $G^3$ is —COOH) in the presence of the coupling reagent. The coupling reagent is typically used in an amount ranging from about 1.0 to about 1.5 molar equivalents relative to the carboxylic acid. Generally, this reaction is conducted in the presence of a hindered amine, such as diisopropylethylamine (DIEA), N-methylmorpholine (NMM), collidine, 2,3,5,6-tetramethylpyridine (TEMP), 2,6-di-tert-butyl-4-dimethylaminopyridine (DBDMAP) and the like, in a diluent, such as dichloromethane, tetrahydrofuran, 1,4-dioxane, acetonitrile, dimethylformamide, dimethyl acetamide, N-methylpyrrolidone or mixtures thereof. The reaction is typically conducted at a temperature ranging from about −20° C. to about 50° C. (e.g., about 20° C. to about 25° C.) for about 1 to about 30 hours or until the reaction is substantially complete. Upon completion of the reaction, the product is typically isolated using conventional procedures, such as extraction, recrystallization, chromatography, and the like.

Compounds of formula 5 are typically prepared by coupling a compound of formula 7:

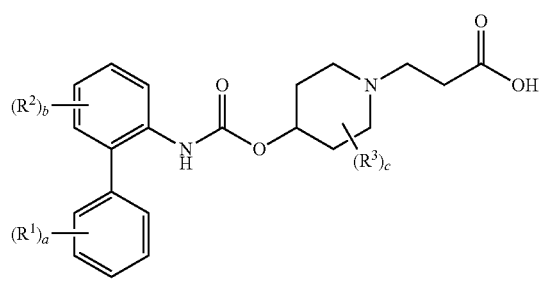

7 with a compound of formula 8a, 8b or 8c:

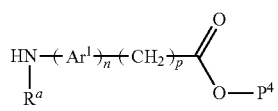

8a

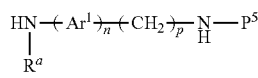

8b

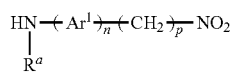

8c wherein $P^4$ is a carboxyl-protecting group (such as $C_{1-6}$ alkyl, including methyl, ethyl, n-propyl and the like; or benzyl); and $P^5$ is an amino-protecting group (such as BOC, Fmoc, Cbz and the like). When a compound of formula 8c is used, the nitro group is subsequently reduced to an amino group using standard reagents and procedures, such as zinc, tin or iron metal and acid (such as acetic acid, hydrochloric acid and the like), or catalytic hydrogenation. In this embodiment, p is typically 0.

Compounds of formula 8a, 8b and 8c are commercially available, known in the art or can be prepared using routine variations of procedures known in the art.

Representative compounds of formula 8a include, by way of example, methyl 4-(methylamino)butyrate, methyl 5-(methylamino)pentanoate, methyl 3-(methylamino)benzoate, methyl 4-(methylamino)benzoate, methyl 3-(methylamino)-4-methylbenzoate, methyl[3-(methylamino)phenyl]acetate and the like.

Representative compounds of formula 8b include, by way of example, (3-methylaminopropyl)carbamic acid tert-butyl ester, (3-methylaminopropyl)carbamic acid 9H-fluoren-9-ylmethyl ester, (4-methylaminobutyl)carbamic acid tert-butyl ester, (4-methylaminobutyl)carbamic acid 9H-fluoren-9-ylmethyl ester, (3-methylaminophenyl)carbamic acid tert-butyl ester, (3-methylaminophenyl)carbamic acid 9H-fluoren-9-ylmethyl ester, (4-methylaminophenyl)carbamic acid tert-butyl ester, (4-methylaminophenyl)carbamic acid 9H-fluoren-9-ylmethyl ester, (3-methylaminobenzyl)carbamic acid tert-butyl ester, (3-methylaminobenzyl)carbamic acid 9H-fluoren-9-ylmethyl ester, (4-methylaminobenzyl)carbamic acid tert-butyl ester, (4-methylaminobenzyl)carbamic acid 9H-fluoren-9-ylmethyl ester, and the like.

Representative compounds of formula 8c include, by way of example, N-methyl-3-nitroaniline, N-methyl-4-nitroaniline, N-ethyl-3-nitroaniline, N-ethyl-4-nitroaniline, and the like.

The carboxylic acid-amine coupling reaction between compound 7 and compound 8a or 8b to form compound 5 is typically conducted using the reagents and reaction conditions described herein for coupling a carboxylic acid and an amine (e.g., compound 5 and compound 6a or 6b). Upon completion of the reaction, the product is typically isolated using conventional procedures, such as extraction, recrystallization, chromatography, and the like.

Compounds of formula 7 are typically prepared by reacting a compound of formula 9:

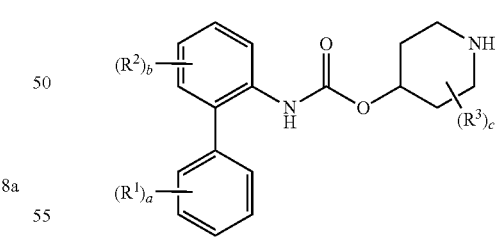

9 with about 0.95 to about 1.5 molar equivalents of acrylic acid. This reaction is typically conducted in a diluent, such as dichloromethane, at a temperature ranging from about 20° C. to about 70° C. (e.g., about 50° C.) for about 6 to about 30 hours or until the reaction is substantially complete. Upon completion of the reaction, the product is typically isolated using conventional procedures, such as extraction, recrystallization, chromatography, and the like.

Compounds of formula 9 are known in the art or can be prepared using routine variations of procedures known in the art. For example, procedures for preparing such compounds are found in U.S. Patent Application Publication No. U.S. 2004/0167167 A1 and R. Naito et al., *Chem. Pharm. Bull.*, 46(8) 1286-1294 (1998). By way of illustration, compounds of formula 9 are typically prepared by reacting a compound of formula 10:

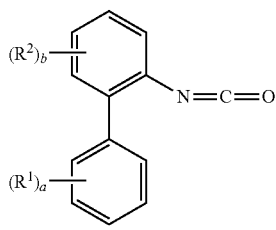

with an alcohol of formula 11:

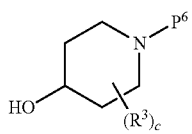

wherein $P^6$ is an amino-protecting group, such as benzyl, BOC, Fmoc, Cbz and the like.

Representative compounds of formula 10 include, by way of example, 2-(phenyl)phenyl isocyanate, 2-(phenyl)-5-methylphenyl isocyanate, 2-(3-chlorophenyl)-4,6-difluorophenyl isocyanate, 2-(phenyl)-6-fluorophenyl isocyanate, 2-(phenyl)-5-bromophenyl isocyanate, 2-(4-bromophenyl)-5-bromophenyl isocyanate, 2-(phenyl)-4-methoxyphenyl isocyanate, 2-(4-methoxyphenyl)phenyl isocyanate, 2-(phenyl)-5-methoxyphenyl isocyanate, and the like.

Representative compounds of formula 11 include, by way of example, 4-hydroxy-1-benzylpiperidine, 4-hydroxypiperidine-1-carboxylic acid tert-butyl ester, 4-hydroxypiperidine-1-carboxylic acid 9H-fluoren-9-ylmethyl ester, 4-hydroxy-4-methyl-1-benzylpiperidine, 2-benzyl-2-azabicyclo[2.2.1]heptan-5-ol, 2-benzyl-2-azabicyclo[2.2.2]octan-5-ol, 8-benzyl-8-azabicyclo[3.2.1]oct-6-en-3-ol, 3-benzyl-3-azabicyclo[3.2.1]octan-8-ol, 8-benzyl-8-azabicyclo[3.2.1]octan-3-ol, 3-benzyl-3-azabicyclo[3.3.1]nonan-9-ol, 9-benzyl-9-azabicyclo[3.3.1]nonan-3-ol, 8-benzylnortropine, 8-benzylnorpseudotropine, and the like.

This reaction is typically conducted by reacting 10 with about 0.95 to about 1.2 molar equivalents of 11 at a temperature ranging from about 20° C. to about 100° C. (e.g., about 60° C. to about 80° C.) for about 6 to about 24 hours or until the reaction is substantially complete. If desired, this reaction can be conducted in a diluent, such as dichloromethane, toluene and the like. Alternatively, this reaction can be conducted in the absence of a diluent. Upon completion of the reaction, the product is typically isolated using conventional procedures, such as extraction, recrystallization, chromatography and the like. Alternatively, the reaction mixture is used directly in the next step of the synthesis without isolation of the product.

The amino-protecting group, $P^6$, is then removed using conventional procedures to afford compound 9. For example, when $P^6$ is a benzyl group, the deprotection reaction is typically conducted using hydrogen or ammonium formate, in the presence of a catalyst, such as a palladium catalyst. Representative catalysts include, by way of illustration, palladium on carbon, palladium hydroxide on carbon and the like. This reaction is typically conducted at a temperature ranging from about 20° C. to about 50° C. (e.g., about 40° C.) for about 6 to about 24 hours or until the reaction is substantially complete. Typically, this reaction is conducted in a diluent, such as methanol, ethanol, isopropanol and the like. Upon completion of the reaction, compound 9 is typically isolated using conventional procedures, such as extraction, recrystallization, chromatography and the like.

Compounds of formula 2 are known in the art or can be prepared from commercially available starting materials and reagents using known procedures. For example, the preparation of a compound of formula 2, where $P^1$ is tert-butyldimethylsilyl, is described in U.S. Patent Application Publication No. 2006/0035931, published Feb. 16, 2006. Other protecting groups that can be employed for $P^1$ include, for example, dimethylisopropylsilyl, diethylisopropylsilyl, dimethylhexylsilyl, tert-butyldiphenylsilyl, diphenylmethylsilyl and the like.

Additionally, if desired, the hydroxyl group of 2 can also be protected, i.e., a compound of formula 2a can be used:

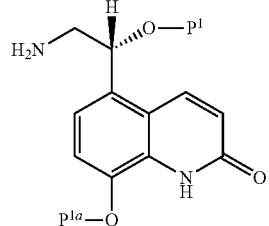

where $P^{1a}$ is a hydroxyl protecting group, such as benzyl group or 4-methoxybenzyl. For example, the preparation of a compound of formula 2a, where $P^1$ is tert-butyldimethylsilyl and the hydroxyl group is protected as a 4-methoxybenzyl group is described in WO 2008/096129. When 2a is used, intermediates such as 3, 12 and the like, will typically contain the $P^{1a}$ group. The $P^{1a}$ is subsequently removed using conventional procedures and reagents. For example, when $P^{1a}$ is a benzyl group, the deprotection reaction is typically conducted using hydrogen or ammonium formate, in the presence of a catalyst, such as a palladium catalyst. When $P^{1a}$ is 4-methoxybenzyl, this group can be removed under acidic hydrolysis conditions, such as 30% TFA in DCM.

Alternatively, compounds of formula I are prepared by coupling a compound of formula 5 with a compound of formula 12:

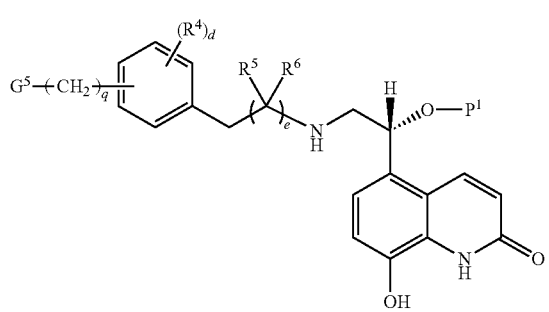

wherein $G^5$ is —COOH (when $G^2$ is —NH$_2$); or $G^5$ is —NH$_2$ (when $G^2$ is —COOH).

The carboxylic acid-amine coupling reaction between compound 5 and compound 12 is typically conducted using the reagents and reaction conditions described herein for coupling a carboxylic acid and an amine (e.g., compound 5 and compound 6a or 6b). Upon completion of the reaction, the product is typically isolated using conventional procedures, such as extraction, recrystallization, chromatography, and the like. Deprotection of the resulting product (e.g., removal of P¹) using standard reagents and conditions then provides a compound of formula I.

Compounds of formula 12 are prepared by reacting a compound of formula 2 with a compound of formula 13a or 13b:

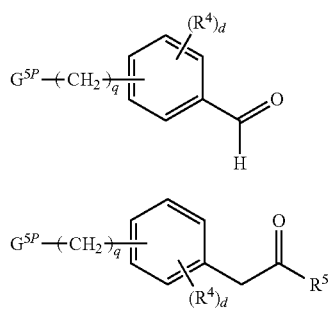

in the presence of a reducing agent; wherein $G^{5P}$ is selected from:

—COOP⁷, where P⁷ is a carboxyl-protecting group (such as $C_{1-6}$ alkyl, including methyl, ethyl, n-propyl and the like; or benzyl); and —NHP⁸, where P⁸ is an amino-protecting group (such as BOC, Fmoc, Cbz and the like). Alternatively, $G^{5P}$ is a nitro group, or $G^{5P}$-$(CH_2)_q$— is NC—$(CH_2)_{q-1}$—, wherein the nitro group or the cyano group is subsequently reduced to an amino group using standard reagents and procedures.

The reaction of compound 2 with compound 13a or 13b is typically conducted using the reagents and reaction conditions described herein for the reductive alkylation of an amine with an aldehyde or ketone (e.g., compound 1 and compound 2). Upon completion of the reaction, the product is typically isolated using conventional procedures, such as extraction, recrystallization, chromatography, and the like.

Compounds of formula 13a and 13b are commercially available, known in the art or can be prepared using routine variations of procedures known in the art.

Representative compounds of formula 13a include, by way of example, methyl 3-formylbenzoate, methyl 4-formylbenzoate, methyl (3-formylphenyl)acetate, methyl (4-formylphenyl)acetate, methyl 3-(3-formylphenyl)propionate, methyl 3-(4-formylphenyl)propionate, (3-formylphenyl)carbamic acid tert-butyl ester, (4-formylphenyl)carbamic acid tert-butyl ester, (3-formylbenzyl)carbamic acid tert-butyl ester, (4-formylbenzyl)carbamic acid tert-butyl ester, [2-(3-formylphenyl)ethyl]carbamic acid tert-butyl ester, [2-(4-formylphenyl)ethyl]carbamic acid tert-butyl ester, and the like.

Representative compounds of formula 13b include, by way of example, methyl 3-(2-oxoethyl)benzoate, methyl 4-(2-oxoethyl)benzoate, methyl 3-[3-(2-oxoethyl)phenyl]acetate, methyl 3-[4-(2-oxoethyl)phenyl]acetate, methyl 3-[3-(2-oxoethyl)phenyl]propionate, methyl 3-[4-(2-oxoethyl)phenyl]propionate, 2-(3-tert-butoxycarbonylaminophenyl)acetaldehyde, 2-(4-tert-butoxycarbonylaminophenyl)acetaldehyde, 2-[3-(tert-butoxycarbonylaminomethyl)phenyl]acetaldehyde, 2-[4-(tert-butoxycarbonylaminomethyl)phenyl]acetaldehyde, 2-{3-[2-(tert-butoxycarbonylamino)-ethyl]phenyl}acetaldehyde, 2-{4-[2-(tert-butoxycarbonylamino)ethyl]phenyl}acetaldehyde, and the like.

Intermediate compounds of formula 12 can also be prepared by reacting a compound of formula 14:

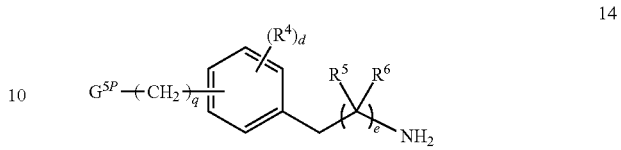

with a compound of formula 15:

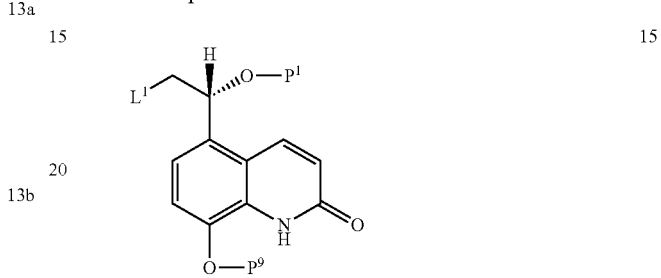

wherein L¹ is a leaving group, such as chloro, bromo, iodo, tosyl, nosyl and the like; and P⁹ is a hydroxyl-protecting group, such as benzyl and the like. The resulting product is then partially deprotected (by removal of P⁷ or P⁸, and P⁹) to provide a compound of formula 12.

The reaction of compound 14 with compound 15 is typically conducted by reacting compound 14 with about 0.95 to about 1.1 molar equivalents of compound 15 in the presence of an excess amount of a base. Representative bases include, for example, sodium bicarbonate, sodium carbonate, potassium bicarbonate, potassium carbonate, trialkyamines (such as triethylamine, diisopropylethylamine, etc.) and the like. This reaction is typically conducted at a temperature ranging from about 20° C. to about 120° C., (e.g., about 100° C.) for about 2 to about 24 hours or until the reaction is substantially complete. Typically, this reaction is conducted in a diluent, such as N-methyl-pyrrolidinone, acetonitrile and the like. If desired, this reaction can be facilitated by subjecting the reaction mixture to microwave radiation (e.g., 300 watts). The reaction can also be conducted neat, i.e., in the absence of a diluent. Additionally, if desired, an excess of amine 14 can be used instead of another base. Upon completion of the reaction, the product is typically isolated using conventional procedures, such as extraction, recrystallization, chromatography and the like.

The resulting product is then partially deprotected (i.e., P⁷ or P⁸ is removed; and P⁹ is removed, if desired) to provide a compound of formula 12. The particular conditions used to remove the protecting groups will depend on the particular groups employed. For example, when P⁷ is $C_{1-6}$ alkyl, such groups are typically removed by hydrolysis of the ester moiety with a base, such as, lithium hydroxide, sodium hydroxide, potassium hydroxide and the like, in a diluent, such as a mixture of methanol and water and the like. This reaction is typically conducted at ambient temperature for about 30 minutes to about 24 hours or until the reaction is substantially complete. When P⁸ is a tert-butoxycarbonyl group, this group is typically removed under acidic hydrolysis conditions, such as 20% trifluoroacetic acid in DCM at ambient temperature. When P⁹ is a benzyl group, this group is readily removed by hydrogenolysis. Typically, this reaction is conducted by contacting the compound with hydrogen in the presence of a catalyst, such as a palladium catalyst. Representative catalysts include palladium hydroxide on carbon, palladium on carbon, and the like. Generally, this debenzylation reaction is conducted in the presence of an acid, such as acetic acid, formic acid and the like. This reaction is typically conducted at a temperature ranging from about 10° C. to about 50° C. (e.g. about 25° C.) for about 6 to about 24 hours or until the reaction is substantially complete. Typically, this reaction is conducted in a diluent, such as methanol, ethanol and the like. Upon completion of the reaction, the product can be isolated using conventional procedures, such as extraction, recrystallization, chromatography and the like, or used directly in the next reaction.

Compounds of formula 14 are known in the art or can be prepared from commercially available starting materials and reagents using known procedures. For example, compounds of formula 14 can be prepared by reacting 13a or 13b with a benzyl amine under reductive alkylation conditions and then removing the benzyl group by hydrogenolysis to afford the compound of formula 14. Representative benzyl amines that may be used include, benzyl amine, (S)-1-phenylethylamine, (R)-1-phenylethylamine, and the like. In particular, chiral benzyl amines are useful for preparing intermediates of formula 14 where $R^5$ is present (i.e., e=1) and the carbon atom to which $R^5$ is attached has a particular stereochemistry (i.e., R or S).

Additionally, compounds of formula 14 where $R^5$ and $R^6$ are independently methyl or ethyl (i.e., not hydrogen) are known in the art or can be prepared using routine procedures as exemplified by the teachings in U.S. Patent Application Publication 2005/0171147 A1, published Aug. 4, 2005; U.S. Patent Application Publication 2005/0277632 A1, published Dec. 15, 2005; WO 2005/092861 A1, published Oct. 6, 2005; and the like.

Compounds of formula 15 are also known in the art or can be prepared from commercially available starting materials and reagents using known procedures. For example, the preparation of a compound of formula 15, where $L^1$ is bromo; $P^1$ is ten-butyldimethylsilyl, and $P^9$ is benzyl is described in U.S. Patent Application Publication No. 2006/0035931, published Feb. 16, 2006.

Alternatively, compounds of formula 12 are prepared by reacting a compound of formula 16:

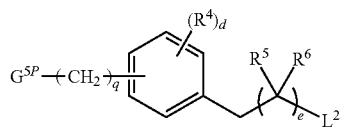

16 with a compound of formula 17:

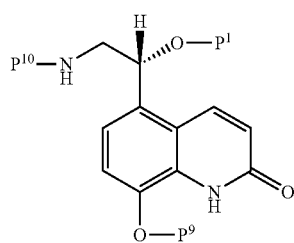

17 wherein $L^2$ is a leaving group, such as chloro, bromo, iodo, tosyl, nosyl and the like; and $P^{10}$ is an amino-protecting group, such as benzyl and the like. In this embodiment, $R^5$ and $R^6$ when present, are typically hydrogen. This reaction is conducted under conditions similar to those described for the reaction of 14 and 15. Compounds of formula 16 and 17 are known in the art or can be prepared from commercially available starting materials and reagents using known procedures. For example, the preparation of a compound of formula 17, where $P^1$ is tert-butyldimethylsilyl, $P^9$ is benzyl, and $P^{10}$ is benzyl is described in U.S. Patent Application Publication No. 2006/0035931, published Feb. 16, 2006.

If desired, a pharmaceutically acceptable salt of a compound of formula I is prepared by contacting the free base form of the compound of formula 1 with a pharmaceutically acceptable acid.

Further details regarding specific reaction conditions and other procedures for preparing representative compounds of this invention or intermediates thereof are described in the Examples set forth herein.

Pharmaceutical Compositions, Combinations and Formulations

Compounds of formula I can be formulated with a carrier or excipient to form a pharmaceutical composition or formulation. Such pharmaceutical compositions will typically contain a therapeutically effective amount of a compound of formula I. In some cases, however, the pharmaceutical composition may contain more than a therapeutically effective amount, e.g., a concentrated bulk composition; or less than a therapeutically effective amount, e.g., individual unit doses designed for multiple administrations to achieve a therapeutically effective amount.

The pharmaceutical composition will typically contain from about 0.01 to about 95 percent by weight of a compound of formula I including, for example, from about 0.01 to about 30 percent by weight; or from about 0.01 to about 10 percent by weight; or from about 0.01 to about 1 percent by weight.

Such pharmaceutical compositions are typically prepared using conventional carriers or excipients. The choice of a particular carrier or excipient, or combinations of carriers or excipients, will depend on various factors such as the mode of administration for the composition, or the medical condition or disease state being treated. Many suitable carriers and excipients for preparing pharmaceutical compositions are commercially available. For example, such materials can be purchased from Sigma (St. Louis, Mo.). Procedures and materials for preparing pharmaceutical compositions suitable for a particular mode of administration are described in the pharmaceutical arts including, for example, *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) compressed propellant gases, such as chlorofluorocarbons and hydrofluorocarbons; and (22) other non-toxic compatible substances employed in pharmaceutical compositions.

The pharmaceutical composition is typically prepared by thoroughly and intimately mixing or blending a compound of formula I with a pharmaceutically acceptable carrier and any optional ingredients. If necessary or desired, the resulting uniformly blended mixture can then be shaped or loaded into tablets, capsules, pills, canisters, cartridges, dispensers and the like using conventional procedures and equipment.

In one embodiment, the pharmaceutical composition is suitable for inhaled administration. Pharmaceutical compositions for inhaled administration will typically be in the form of an aerosol or a powder. Such compositions are generally administered using well-known delivery devices, such as a nebulizer inhaler, a metered-dose inhaler (MDI), a dry powder inhaler (DPI) or a similar delivery device.

In a particular embodiment, the pharmaceutical composition comprising the therapeutic agent is administered by inhalation using a nebulizer inhaler. Such nebulizer devices typically produce a stream of high velocity air that causes the pharmaceutical composition comprising the therapeutic agent to spray as a mist that is carried into the patient's respiratory tract. Accordingly, when formulated for use in a nebulizer inhaler, the therapeutic agent is typically dissolved in a suitable carrier to form a solution. Alternatively, the therapeutic agent can be micronized and combined with a suitable carrier to form a suspension of micronized particles. Nebulizer devices suitable for administering therapeutic agents by inhalation are described in the art or such devices are commercially available. For example, representative nebulizer devices or products include the Respimat Softmist Inhalaler (Boehringer Ingelheim); the AERx Pulmonary Delivery System (Aradigm Corp.); the PAM LC Plus Reusable Nebulizer (Pari GmbH); and the like.

A representative pharmaceutical composition for use in a nebulizer inhaler comprises an isotonic aqueous solution comprising from about 0.05 μg/mL to about 10 mg/mL of a compound of formula I. In one embodiment, the solution has a pH of about 4 to about 6.

In another particular embodiment, the pharmaceutical composition comprising the therapeutic agent is administered by inhalation using a dry powder inhaler. Such dry powder inhalers typically administer the therapeutic agent as a free-flowing powder that is dispersed in a patient's airstream during inspiration. In order to achieve a free-flowing powder, the therapeutic agent is typically formulated with a suitable excipient such as lactose, starch, mannitol, dextrose, polylactic acid (PLA), polylactide-co-glycolide (PLGA) or combinations thereof. Typically, the therapeutic agent is micronized and combined with a suitable carrier to form a blend suitable for inhalation. Accordingly, in one embodiment, the compound of formula I is in micronized form.

A representative pharmaceutical composition for use in a dry powder inhaler comprises dry milled lactose and micronized particles of a compound of formula I.

Such a dry powder formulation can be made, for example, by combining the lactose with the therapeutic agent and then dry blending the components. Alternatively, if desired, the therapeutic agent can be formulated without an excipient. The pharmaceutical composition is then typically loaded into a dry powder dispenser, or into inhalation cartridges or capsules for use with a dry powder delivery device.

Dry powder inhaler delivery devices suitable for administering therapeutic agents by inhalation are described in the art or such devices are commercially available. For example, representative dry powder inhaler delivery devices or products include Aeolizer (Novartis); Airmax (IVAX); ClickHaler (Innovata Biomed); Diskhaler (GlaxoSmithKline); Diskus/Accuhaler (GlaxoSmithKline); Easyhaler (Orion Pharma); Eclipse (Aventis); FlowCaps (Hovione); Handihaler (Boehringer Ingelheim); Pulvinal (Chiesi); Rotahaler (GlaxoSmithKline); SkyeHaler/Certihaler (SkyePharma); Twisthaler (Schering-Plough); Turbuhaler (AstraZeneca); Ultrahaler (Aventis); and the like.

In yet another particular embodiment, the pharmaceutical composition comprising the therapeutic agent is administered by inhalation using a metered-dose inhaler. Such metered-dose inhalers typically discharge a measured amount of the therapeutic agent using a compressed propellant gas. Accordingly, pharmaceutical compositions administered using a metered-dose inhaler typically comprise a solution or suspension of the therapeutic agent in a liquefied propellant. Any suitable liquefied propellant may be employed including hydrofluoroalkanes (HFAs), such as 1,1,1,2-tetrafluoroethane (HFA 134a) and 1,1,1,2,3,3,3-heptafluoro-n-propane, (HFA 227); and chlorofluorocarbons, such as $CCl_3F$. In a particular embodiment, the propellant is hydrofluoroalkanes. In some embodiments, the hydrofluoroalkane formulation contains a co-solvent, such as ethanol or pentane, and/or a surfactant, such as sorbitan trioleate, oleic acid, lecithin, and glycerin.

A representative pharmaceutical composition for use in a metered-dose inhaler comprises from about 0.01% to about 5% by weight of a compound of formula I; from about 0% to about 20% by weight ethanol; and from about 0% to about 5% by weight surfactant; with the remainder being an HFA propellant.

Such compositions are typically prepared by adding chilled or pressurized hydrofluoroalkane to a suitable container containing the therapeutic agent, ethanol (if present) and the surfactant (if present). To prepare a suspension, the therapeutic agent is micronized and then combined with the propellant. The formulation is then loaded into an aerosol canister, which typically forms a portion of a metered-dose inhaler device.

Metered-dose inhaler devices suitable for administering therapeutic agents by inhalation are described in the art or such devices are commercially available. For example, representative metered-dose inhaler devices or products include AeroBid Inhaler System (Forest Pharmaceuticals); Atrovent Inhalation Aerosol (Boehringer Ingelheim); Flovent (GlaxoSmithKline); Maxair Inhaler (3M); Proventil Inhaler (Schering); Serevent Inhalation Aerosol (GlaxoSmithKline); and the like.

In another embodiment, the pharmaceutical composition is suitable for oral administration. Pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the embodiments as an active ingredient.

When intended for oral administration in a solid dosage form (i.e., as capsules, tablets, pills and the like), the pharmaceutical composition will typically comprise a compound of formula I and one or more pharmaceutically acceptable carriers, such as sodium citrate or dicalcium phosphate. Optionally or alternatively, such solid dosage forms may also comprise: (1) fillers or extenders, such as starches, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and/or sodium carbonate; (5) solution retarding agents, such as paraffin; (6) absorption accelerators, such as quaternary ammonium compounds; (7) wetting agents, such as cetyl alcohol and/or glycerol monostearate; (8) absorbents, such as kaolin and/or bentonite clay; (9) lubricants, such as talc, calcium stearate, magnesium stearate, solid polyethylene glycols, sodium lauryl sulfate, and/or mixtures thereof; (10) coloring agents; and (11) buffering agents.

Release agents, wetting agents, coating agents, sweetening, flavoring and perfuming agents, preservatives and antioxidants can also be present in the pharmaceutical composition. Examples of pharmaceutically acceptable antioxidants include: (1) water-soluble antioxidants, such as ascorbic acid, cysteine hydrochloride, sodium bisulfate, sodium metabisulfate sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like. Coating agents for tablets, capsules, pills and like, include those used for enteric coatings, such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical composition may also be formulated to provide slow or controlled release of the active ingredient using, by way of example, hydroxypropyl methyl cellulose in varying proportions; or other polymer matrices, liposomes and/or microspheres.

Additionally, the pharmaceutical composition may optionally contain an opacifying agent and may be formulated so that the active ingredient released primarily in a certain portion of the gastrointestinal tract or in a delayed manner. Examples of embedding compositions which can be used include polymeric substances and waxes. The active ingredient or a pharmaceutical composition containing the active ingredients can also be in micro-encapsulated form.

Suitable liquid dosage forms for oral administration include, by way of illustration, pharmaceutically acceptable emulsions, microemulsions, solutions, suspensions, syrups and elixirs. Such liquid dosage forms typically comprise the active ingredient and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

When intended for oral administration, the pharmaceutical composition may be packaged in a unit dosage form. The term "unit dosage form" means a physically discrete unit suitable for dosing a patient, i.e., each unit containing a predetermined quantity of active agent calculated to produce the desired therapeutic effect either alone or in combination with one or more additional units. For example, such a unit dosage form may be a capsule, tablet, pill, and the like.

The compounds of formula I can also be administered transdermally using known transdermal delivery systems and excipients. For example, a compound of the embodiments can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

Additionally, a compound of formula I can be administered parenterally, i.e., intravenously, subcutaneously or intramuscularly. For parenteral administration, a compound of formula I is typically dissolved in a carrier acceptable for parenteral administration, such as sterile water, saline, vegetable oil and the like. By way of illustration, an intravenous composition typically comprises a sterile aqueous solution of a compound of formula I, wherein the solution has a pH in the range of about 4 to about 7.

If desired, a compound of formula I may be administered in combination with one or more other therapeutic agents. In this aspect of the invention, a compound of formula I is either physically mixed with the other therapeutic agent to form a composition containing both agents; or each agent is present in separate and distinct compositions which are administered to the patient simultaneously or sequentially.

For example, a compound of formula I can be combined with second therapeutic agent using conventional procedures and equipment to form a composition comprising a compound of formula I and a second therapeutic agent. Additionally, the therapeutic agents may be combined with a pharmaceutically acceptable carrier to form a pharmaceutical composition comprising a compound of formula I, a second therapeutic agent and a pharmaceutically acceptable carrier. In this embodiment, the components of the composition are typically mixed or blended to create a physical mixture. The physical mixture is then administered in a therapeutically effective amount using any of the routes described herein.

Alternatively, the therapeutic agents may remain separate and distinct before administration to the patient. In this embodiment, the therapeutic agents are not physically mixed together before administration but are administered simultaneously or sequentially as separate compositions. For example, a compound of formula I can be administered by inhalation simultaneously or sequentially with another therapeutic agent using an inhalation delivery device that employs separate compartments (e.g. blister packs) for each therapeutic agent. Alternatively, the combination may be administered using separate delivery devices, i.e., one delivery device for each therapeutic agent. Additionally, the therapeutic agents can be delivered by different routes of administration, i.e., one by inhalation and the other by oral administration.

Any therapeutic agent compatible with the compounds of formula I may be used in combination with such compounds. In a particular embodiment, the second therapeutic agent is one that is effectively administered by inhalation. By way of illustration, representative types of therapeutic agents that may be used with the compounds of the embodiments include, but are not limited to, anti-inflammatory agents, such as steroidal anti-inflammatory agents (including corticosteroids and glucocorticoids), non-steroidal anti-inflammatory agents (NSAIDs), and $PDE_4$ inhibitors; bronchodilators, such as $PDE_3$ inhibitors, adenosine 2b modulators and $\beta_2$ adrenergic receptor agonists; antiinfective agents, such as Gram-positive antibiotics, Gram-negative antibiotics, and antiviral agents; antihistamines; protease inhibitors; afferent blockers, such as D₂ agonists and neurokinin modulators; and muscarinic receptor antagonists (antichlolinergic agents). Numerous examples of such therapeutic agents are well known in the art. Suitable doses for the other therapeutic agents administered in combination with a compound of the embodiments are typically in the range of about 0.05 µg/day to about 500 mg/day.

In a particular embodiment, a compound of formula I is administered in combination with a steroidal anti-inflammatory agent. Representative examples of steroidal anti-inflammatory agents that can be used in combination with the compounds of the embodiments include, but are not limited to, beclomethasone dipropionate; budesonide; butixocort propionate; 20R-16α,17α-[butylidenebis(oxy)]-6α,9α-difluoro-11β-hydroxy-17β-(methylthio)androsta-4-en-3-one (RPR-106541); ciclesonide; dexamethasone; 6α,9α-difluoro-17α-[(2-furanylcarbonyl)oxy]-11β-hydroxy-16α-methyl-3-oxoandrosta-1,4-diene-17β-carbothioic acid S-fluoromethyl ester; 6α,9α-difluoro-11β-hydroxy-16α-methyl-17α-[(4-methyl-1,3-thiazole-5-carbonyl)oxy]-3-oxoandrosta-1,4-diene-17β-carbothioic acid S-fluoromethyl ester; 6α,9α-difluoro-11β-hydroxy-16α-methyl-3-oxo-17α-propionyloxyandrosta-1,4-diene-17β-carbothioic acid (S)-(2-oxotetrahydrofuran-3S-yl) ester; flunisolide; fluticasone furoate; fluticasone propionate; methyl prednisolone; mometasone furoate; prednisolone; prednisone; rofleponide; ST-126; triamcinolone acetonide; and the like, or pharmaceutically acceptable salts or solvates thereof. Such steroidal anti-inflammatory agents are commercially available or can be prepared using conventional procedures and reagents. For example, the preparation and use of steroidal anti-inflammatory agents is described in U.S. Pat. No. 6,537,983, issued Mar. 25, 2003; U.S. Pat. No. 6,750,210 B2, issued Jun. 15, 2004; U.S. Pat. No. 6,759,398 B2, issued Jul. 6, 2004; U.S. Pat. No. 6,858,596 B2, issued Feb. 22, 2005; U.S. Pat. No. 7,101,866 B2, issued Sep. 5, 2006; and the references cited therein.

When employed, the steroidal anti-inflammatory agent is typically administered in an amount that produces a therapeutically beneficial effect when co-administered with a compound of the embodiments. Typically, the steroidal anti-inflammatory agent will be administered in an amount sufficient to provide from about 0.05 µg to about 500 µg per dose.

The following examples illustrate representative pharmaceutical compositions:

A. Dry Powder Composition

A micronized compound of formula I (100 mg) is blended with milled lactose (25 g) (e.g., lactose in which not greater than about 85% of the particles have a MMD of about 60 µm to about 90 µm and not less than 15% of the particles have a MMD of less then 15 µm). This blended mixture is then loaded into individual blisters of a peelable blister pack in an amount sufficient to provide about 10 µg to about 500 µg of the compound of formula I per dose. The contents of the blisters are administered using a dry powder inhaler.

B. Dry Powder Composition

A micronized compound of formula I (1 g) is blended with milled lactose (200 g) to form a bulk composition having a weight ratio of compound to milled lactose of 1:200. The blended composition is packed into a dry powder inhalation device capable of delivering between about 10 µg to about 500 µg of the compound of formula I per dose.

C. Dry Powder Composition

A micronized compound of formula I (100 mg) and a micronized steroidal anti-inflammatory agent (500 mg) are blended with milled lactose (30 g). This blended mixture is then loaded into individual blisters of a peelable blister pack in an amount sufficient to provide about 10 µg to about 500 µg of the compound of formula I per dose. The contents of the blisters are administered using a dry powder inhaler.

D. Metered-Dose Inhaler Composition

A micronized compound of formula I (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 µm. The micronized composition is then loaded into metered-dose inhaler cartridges containing pressurized 1,1,1,2-tetrafluoroethane in an amount sufficient to provide about 10 µg to about 500 µg of the compound of formula I per dose when administered by the metered dose inhaler.

E. Nebulizer Composition

A compound of formula I (25 mg) is dissolved in citrate buffered (pH 5) isotonic saline (125 mL). The mixture is stirred and sonicated until the compound is dissolved. The pH of the solution is checked and adjusted, if necessary, to pH 5 by slowly adding aqueous 1N sodium hydroxide. The solution is administered using a nebulizer device that provides about 10 µg to about 500 µg of the compound of formula I per dose.

F. Hard Gelatin Capsules

A compound of formula I (50 g), spray-dried lactose (440 g) and magnesium stearate (10 g) are thoroughly blended. The resulting composition is loaded into a hard gelatin capsule (500 mg of composition per capsule) that is administered orally.

G. Injectable Composition

A compound of formula I (0.2 g) is blended with 0.4 M sodium acetate buffer solution (2.0 mL). The pH of the resulting solution is adjusted to pH 4 using 0.5 N aqueous hydrochloric acid or 0.5 N aqueous sodium hydroxide, as necessary, and then sufficient water for injection is added to provide a total volume of 20 mL. The mixture is then filtered through a sterile filter (0.22 micron) to provide a sterile solution suitable for administration by injection.

Utility

The compounds of formula I possess both muscarinic receptor antagonist activity and β₂ adrenergic receptor agonist and therefore, such compounds are expected to be useful as therapeutic agents for treating medical conditions mediated by muscarinic receptors and/or β₂ adrenergic receptors, i.e., medical conditions that are ameliorated or moderated by treatment with a muscarinic receptor antagonist or a β₂ adrenergic receptor agonist. Such medical conditions are well known to those of ordinary skill in the art as exemplified by the teachings of Eglen et al., *Muscarinic Receptor Subtypes: Pharmacology and Therapeutic Potential, DN&P* 10(8), 462-469 (1997); Emilien et al., *Current Therapeutic Uses and Potential of beta-Adrenoceptor Agonists and Antagonists, European I Clinical Pharm.*, 53(6), 389-404 (1998); and the references cited therein. Such medical conditions include, by way of example, pulmonary disorders or diseases associated with reversible airway obstruction, such as chronic obstructive pulmonary disease (e.g., chronic and wheezy bronchitis and emphysema), asthma, pulmonary fibrosis, adult/acute respiratory distress syndrome (ARDS), chronic respiratory obstruction, bronchial hyperactivity, allergic rhinitis, pneumoconiosis (such as aluminosis, anthracosis, asbestosis, chalicosis, ptilosis, siderosis, silicosis, tabacosis and byssinosis), and other pulmonary disorders of unknown origin which benefit from therapeutic agent-induced bronchodilation. Additionally, other conditions known to be treatable, at least in part, with a muscarinic receptor antagonist or a β₂ adrenergic receptor agonist include premature labor, depression, congestive heart failure, skin diseases (e.g., inflammatory, allergic, psoriatic and proliferative skin diseases), conditions where lowering peptic acidity is desirable (e.g., peptic and gastric ulceration) and muscle wasting disease.

Accordingly, one embodiment of this invention relates to a method for treating a pulmonary disorder, the method comprising administering to a patient in need of treatment a therapeutically effective amount of a compound of formula I. When used to treat a pulmonary disorder, the compounds of formula I will typically be administered by inhalation in multiple doses per day, in a single dose per day or a single dose per week. Generally, the dose for treating a pulmonary disorder is expected to range from about 10 µg/day to about 1500 µg/day; such as about 25 µg/day to about 1000 µg/day; including about 50 µg/day to about 500 µg/day.

In one of its method aspects, this invention relates to a method of treating chronic obstructive pulmonary disease or asthma, the method comprising administering to a patient a therapeutically effective amount of a compound of formula I. Generally, the dose for treating COPD or asthma is expected to range from about 10 µg/day to about 1500 µg/day. In particular, this method includes alleviating the symptoms of COPD or asthma. The term "COPD" is understood by those of ordinary skill in the art to include a variety of respiratory conditions, including chronic obstructive bronchitis and emphysema, as exemplified by the teachings of Barnes, *Chronic Obstructive Pulmonary Disease, N. Engl. J. Med.,* 2000: 343:269-78, and the references cited therein.

When administered by inhalation, the compounds of formula I typically have the effect of producing bronchodilation. Accordingly, in another of its method aspects, the invention relates to a method of producing bronchodilation in a mammal, the method comprising administering to the mammal a bronchodilation-producing amount of a compound of formula I. Generally, the dose for producing bronchodilation will range from about 10 µg/day to about 1500 µg/day.

When used as a therapeutic agent, the compounds of formula I are optionally administered in combination with another therapeutic agent or agents. In particular, by administering the compounds of formula I with a steroidal anti-inflammatory agent, triple therapy, i.e., muscarinic receptor antagonist activity, $\beta_2$ adrenergic receptor agonist activity, and anti-inflammatory activity, is expected using only two therapeutic agents. Since pharmaceutical compositions (and combinations) containing two therapeutic agents are typically easier to formulate and/or administer compared to compositions containing three therapeutic agents, such two component compositions provide a significant advantage over compositions containing three therapeutic agents. Accordingly, in particular embodiments, the pharmaceutical compositions, combinations and methods of this invention further comprise a steroidal anti-inflammatory agent.

Since compounds of formula I possess both muscarinic receptor antagonist and activity $\beta_2$ adrenergic agonist activity, such compounds are also useful as research tools for investigating or studying biological systems or samples having muscarinic receptors or $\beta_2$ adrenergic receptors. Additionally, such compounds are useful in screening assays to discover, for example, new compounds having both muscarinic receptor antagonist activity and adrenergic agonist activity. The biological systems or samples employed may comprise muscarinic receptors or $\beta_2$ adrenergic receptors or both. Any suitable biological system or sample having muscarinic receptors and/or $\beta_2$ adrenergic receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.), and the like.

When used as a research tool, a biological system or sample comprising a muscarinic receptor and/or a $\beta_2$ adrenergic receptor is typically contacted with a muscarinic receptor-antagonizing or $\beta_2$ adrenergic receptor-agonizing amount of a compound of formula I. The effects on the biological system or sample produced by the compound are then determined or measured using conventional procedures and equipment, such as by measuring binding in a radioligand binding assays or ligand-mediated changes in a functional assay or by determining the amount of bronchoprotection provided by the compound in a bronchoprotection assay in a mammal. Representative functional assays include ligand-mediated changes in intracellular cyclic adenosine monophosphate (cAMP); ligand-mediated changes in activity of the enzyme adenylyl cyclase (which synthesizes cAMP); ligand-mediated changes in incorporation of guanosine 5'-O-(thio)triphosphate ([$^{35}$S]GTP S) into isolated membranes via receptor catalyzed exchange of [$^{35}$S]GTP S for GDP; ligand-mediated changes in free intracellular calcium ions (measured, for example, with a fluorescence-linked imaging plate reader or FLIPR® from Molecular Devices, Inc.); and the like. Compounds of formula I are expected to antagonize or decrease the activation of a muscarinic receptor or agonize or cause activation of a $\beta_2$ adrenergic receptor and in the functional assays listed herein or in assays of a similar nature. The compounds of formula I will typically be used in these studies at a concentration ranging from about 0.1 nanomolar to about 100 nanomolar.

Additionally, the compounds of formula I can be used as research tools for evaluating other chemical compounds. In this aspect, a compound of formula I is used as a standard in an assay to allow comparison of the results obtained with a test compound and the compound of formula I. For example, muscarinic receptor and/or $\beta_2$ adrenergic receptor binding data (as determined, for example, by in vitro radioligand displacement assays) for a test compound or a group of test compounds is compared to the muscarinic receptor and/or $\beta_2$ adrenergic receptor binding data for a compound of formula I to identify those test compounds that have desirable binding, i.e. test compounds having binding about equal or superior to a compound of formula I, if any. Alternatively, for example, bronchoprotective effects can be determined for test compounds and a compound of formula I in a bronchoprotection assay in a mammal and this data compared to identify test compounds providing about equal or superior bronchoprotective effects or duration of action. This aspect includes, as separate embodiments, both (i) the generation of comparison data (using the appropriate assays) and (ii) the analysis of the test data to identify test compounds of interest.

The properties and utility of the compounds of formula I can be demonstrated using various in vitro and in vivo assays known to those of ordinary skill in the art. For example, representative assays are described in further detail in the following Examples.

EXAMPLES

The following examples are provided to illustrate various representative embodiments and aspects of this invention and are not intended to limit the scope of this invention in any way unless specifically indicated.

All reagents, starting materials and solvents used in the following examples were purchased from commercial suppliers (such as Aldrich Chemical Company, Milwaukee, Wis.) and were used without further purification unless otherwise indicated.

¹H NMR spectra were recorded on a 400 MHz Varian AS400 spectrometer, unless otherwise indicated. Chemical shifts are reported as δ values in ppm relative to tetramethylsilane (TMS) as an internal standard. Coupling constants (J values) are given in hertz (Hz) and multiplicities are reported using the following abbreviations: s=singlet, d=doublet, t=triplet, q=quartet, m=multiplet, br=broad, nd=not determined.

Liquid Chromatography Mass Spectroscopy (LC-MS) Conditions

LC-MS data were obtained using an Agilent 1100 Liquid Chromatography System—G1312A Binary Pump (Agilent Technologies), a ZORBAX Rapid Resolution 3.5 µm Rx, Bonus-RP column (3.5 µm particle size; 2.1 mm×50 mm) (Agilent Technologies) and API 150EX Single Quadrupole LC/MS Mass Spectrometer (Perkin-Elmer Sciex Instruments). The solvent systems used were:

Solvent A: 98% water and 2% acetonitrile (v/v)+1 mL/L TFA

Solvent B: 90% acetonitrile and 10% water (v/v)+1 mL/L TFA

Flow Rate: 500 µL/min

Gradient: (Method 10-90): 10% B to 90% B over 3 min
(Method 2-90): 2% B to 90% B over 3 min
(Method 10-70): 10% B to 70% B over 3 min.

HPLC Conditions

HPLC was conducted using an HP 1100 Series HPLC System (Agilent Technologies) and a ZORBAX Rapid Resolution 3.5 µm Rx, Bonus-RP column (3.5 µm particle size; 2.1 mm×50 mm) (Agilent Technologies) or an Ascentis Express C18 HPLC column (2.7 µm particle size, 3.0 mm×3 cm). The solvent systems used were:

Solvent A: 98% water and 2% acetonitrile (v/v)+1 mL/L TFA

Solvent B: 90% acetonitrile and 10% water (v/v)+1 mL/L TFA

Flow Rate: 500 µL/min

Gradient: (Method 10-50): 10% B to 50% B over 6 min
(Method 10-70): 10% B to 70% B over 6 min
(Method 2-90): 2% B to 90% B over 6 min.

Example 1

Preparation of 3-[4-(Biphenyl-2-ylcarbamoyloxy) piperidin-1-yl]propionic Acid

A stirred solution of biphenyl-2-ylcarbamic acid piperidin-4-yl ester (50.0 g, 168.7 mmol) (see, e.g., U.S. Patent Publication No. 2006/0035931 A1, published Feb. 16, 2006) and acrylic acid (15.1 mL, 219.3 mmol) in DCM (500 mL) was heated at 50° C. overnight. The reaction mixture was concentrated under reduced pressure and the residue was dissolved in MeOH (600 mL). The resulting solution was heated at 75° C. for 2 h and then allowed to stand at room temperature for about 48 h. The resulting solid was collected by filtration, washed with MeOH, and dried to give the title compound (61.5 g, 99% yield).

Example 2

Preparation of 4-({3-[4-(Biphenyl-2-ylcarbamoyloxy)piperidin-1-yl]propionyl}methyl-amino)butyric Acid Methyl Ester To a stirred mixture of 4-methylaminobutyric acid methyl ester hydrochloride (546 mg, 3.26 mmol) and 3-[4-(biphenyl-2-ylcarbamoyloxy)piperidin-1-yl]propionic acid (1.20 g, 3.26 mmol) in DCM (15 mL) was added N,N,N',N'-tetramethyl-O-(7-azabenzotriazol-1-yl)uronium hexafluorophosphate (1.36 g, 3.58 mmol) followed by N,N-diisopropylethylamine (1.42 mL, 8.15 mmol). LC-MS (Method 2-90) showed product was present (Rt 3.11 min; m/z 482.4 [M+H]⁺). Water and DCM were added and the layers were separated. The organic layer was washed with water (2×) and brine, dried over sodium sulfate, filtered and concentrated under reduced pressure to give the title compound (2.0 g, 100% yield) as a light yellow oil.

Example 3

Preparation of 4-({3-[4-(Biphenyl-2-ylcarbamoyloxy)piperidin-1-yl]propionyl}methylamino)butyric Acid To a stirred solution of 4-({3-[4-(biphenyl-2-ylcarbamoyloxy)piperidin-1-yl]-propionyl}methylamino)butyric acid methyl ester (1.00 g, 2.08 mmol) in THF (10 mL) was added dropwise aqueous sodium hydroxide (1.0 M, 10.4 mL, 10.4 mmol) and the reaction mixture was stirred overnight at room temperature. LC-MS (Method 10-90) showed product was present (Rt 3.34 min; m/z 468.2 [M+H]⁺). The pH of the mixture was adjusted to pH 5 with aqueous hydrochloric acid (6 M) and the mixture was concentrated under reduced pressure. Aqueous ammonium chloride solution was added to the residue and this mixture was washed with EtOAc. The pH of the aqueous layer was adjusted to pH 4 with phosphate buffer solution and the aqueous layer was then extracted with a 1:3 mixture of isopropyl acetate/chloroform (4×). The combined organic layers were dried over sodium sulfate, filtered and concentrated under reduced pressure to give the title compound as a colorless oil, which was used without further purification.

Example 4

Preparation of Biphenyl-2-ylcarbamic Acid 1-(2-{[3-(4-(1,3-Dioxolan-2-yl)-phenylcarbamoyl)propyl] methylcarbamoyl}ethyl)piperidin-4-yl Ester To a solution of 4-({3-[4-(biphenyl-2-ylcarbamoyloxy)piperidin-1-yl]-propionyl}methylamino)butyric acid (75 mg, 0.16 mmol) and 4-(1,3-dioxolan-2-yl)phenylamine (26 mg, 0.16 mmol) in DCM (3 mL) was added N,N,N',N'-tetramethyl-O-(7-azabenzotriazol-1-yl)uronium hexafluorophosphate (73.2 mg, 0.192 mmol) followed by N,N-diisopropylethylamine (55.9 µL, 0.321 mmol). The reaction mixture was stirred at room temperature for about 48 h. LC-MS (Method 2-90) showed product was present (Rt 3.87 min; m/z 615.4 [M+H]⁺). Water and DCM were added and the layers were separated. The organic layer was washed with water (2×) and brine, dried over sodium sulfate, filtered and concentrated under reduced pressure to give the title compound as a yellow oil, which was used without further purification. In subsequent experiments, this compound was also isolated as a filterable solid.

Example 5

Preparation of Biphenyl-2-ylcarbamic Acid 1-(2-{[3-(4-Formylphenylcarbamoyl)-propyl] methylcarbamoyl}ethyl)piperidin-4-yl Ester To a stirred solution of biphenyl-2-ylcarbamic acid 1-(2-{[3-(4-(1,3-dioxolan-2-yl)phenylcarbamoyl)propyl] methylcarbamoyl}ethyl)piperidin-4-yl ester (98 mg, 0.16 mmol) in acetonitrile (2 mL) was added aqueous hydrochloric acid (3 M, 1.07 mL). The resulting dark orange solution was stirred at room temperature. Water was added and the resulting mixture was extracted with DCM (2×). The combined organic layers were dried over sodium sulfate, filtered and concentrated under reduced pressure to give the title compound, which was used without further purification.

Example 6

Preparation of Biphenyl-2-ylcarbamic Acid 1-(2-{[3-(4-{[(R)-2-(tert-Butyldimethyl-silanyloxy)-2-(8-hydroxy-2-oxo-1,2-dihydroquinolin-5-yl)ethylamino]methyl}-phenylcarbamoyl)propyl]methylcarbamoyl}ethyl)piperidin-4-yl Ester To a stirred solution of biphenyl-2-ylcarbamic acid 1-(2-{[3-(4-formyl-phenylcarbamoyl)propyl]methylcarbamoyl}ethyl)piperidin-4-yl ester (91 mg, 0.16 mmol) in DCM (2 mL) was added 5-[(R)-2-amino-1-(tert-butyldimethylsilanyloxy)ethyl]-8-hydroxy-1H-quinolin-2-one acetic acid salt (101 mg, 0.256 mmol) (see, e.g., U.S. Patent Publication No. 2006/0035931 A1, published Feb. 16, 2006) followed by MeOH (1 mL). The resulting yellow solution was stirred at room temperature for 10 min and then sodium triacetoxyborohydride (89 mg, 0.40 mmol) was added and this mixture was stirred overnight. LC-MS (Method 2-90) showed product was present (Rt 3.25 min; m/z 889.8 [M+H]$^+$). Water and DCM were added and the layers were separated. The organic layer was washed with water (2×) and brine, dried over sodium sulfate, filtered and concentrated under reduced pressure to give the title compound, which was used without further purification.

Example 7

Preparation of Biphenyl-2-ylcarbamic Acid 1-(2-{[3-(4-{[(R)-2-Hydroxy-2-(8-hydroxy-2-oxo-1,2-dihydroquinolin-5-yl)ethylamino]methyl}-phenylcarbamoyl)propyl]methylcarbamoyl}ethyl)piperidin-4-yl Ester Ditrifluoroacetic Acid Salt (Compound I-1)

LC-MS (Method 2-90) showed product was present (Rt 3.00 min; m/z 775.4 [M+H]$^+$). The reaction mixture was concentrated under reduced pressure and the residue was purified by HPLC to give the title compound (27.8 mg, 39% yield, 94% purity).

Example 8

Preparation of [3-(Tritylamino)phenyl]acetic Acid

To a stirred solution of (3-aminophenyl)acetic acid (30.20 g, 199.8 mmol) in pyridine (200 mL) under nitrogen at 0° C. was added dropwise a solution of trityl bromide (77.5 g, 240 mmol) in DCM (120 mL) over a period of 5 min. The reaction mixture was stirred at room temperature for 14 h and then concentrated under reduced pressure. To the residue was added DCM (~800 mL) and water (=800 mL) and the layers were separated. The organic layer was washed with water (3×~500 mL), dried over sodium sulfate, filtered, and concentrated under reduced pressure to afford a brownish off-white solid (100.1 g). The solid was suspended in EtOH (500 mL) and this mixture was heated at 60° C. for 1 h and then cooled to room temperature. The solid was collected by filtration, washed with EtOH and dried under high vacuum to give the title compound (67.2 g, 85% yield) as a white solid.
$^1$H NMR (DMSO-d$_6$) δ 7.25 (m); 7.13 (m); 6.70 (s); 6.63 (t); 6.55 (d); 6.27 (d); 6.09 (m); 3.29 (br s); 3.16 (s).

Example 9

Preparation of 2-[3-(Tritylamino)phenyl]ethanol

To a stirred suspension of [3-(tritylamino)phenyl]acetic acid (30.00 g, 76.24 mmol) in THF (126 mL) under nitrogen at 0° C. was added dropwise a solution of borane dimethyl sulfide complex in THF (2 M, 76.2 mL, 152 mmol) over a period of 45 min while maintaining the temperature at ≤1.8° C. The resulting slightly yellow homogeneous solution was stirred at room temperature for 18 h. Saturated aqueous sodium bicarbonate solution (~300 mL) was added slowly (strongly effervescent upon initial addition) and the resulting

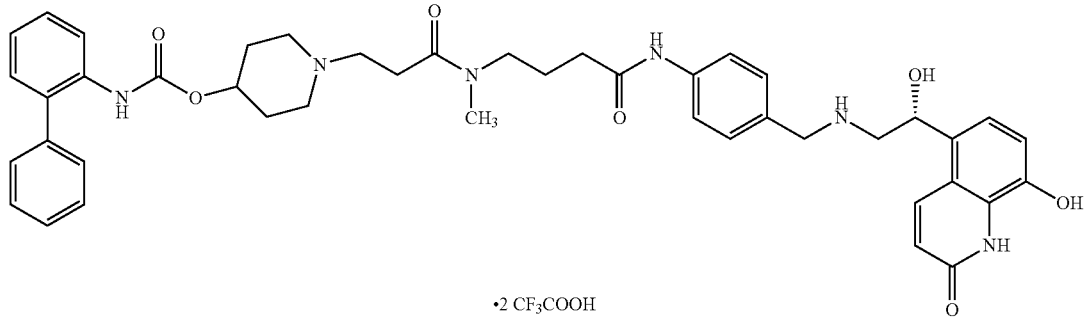 [SMILES: CN(CCCC(=O)Nc1ccc(CNC[C@H](O)c2ccc(O)c3[nH]c(=O)ccc23)cc1)C(=O)CCN1CCC(OC(=O)Nc2ccccc2-c2ccccc2)CC1]

•2 CF$_3$COOH

To a solution of biphenyl-2-ylcarbamic acid 1-(2-{[3-(4-{[(R)-2-(tert-butyldimethylsilanyloxy)-2-(8-hydroxy-2-oxo-1,2-dihydroquinolin-5-yl)ethylamino]methyl}phenylcarbamoyl)propyl]methylcarbamoyl}ethyl)piperidin-4-yl ester (~0.16 mmol) in DCM (3 mL) was added triethylamine trihydrofluoride (260 μL, 1.60 mmol). The reaction mixture was stirred at room temperature overnight.

mixture was stirred at room temperature overnight. The mixture was extracted with EtOAc (2×~330 mL) and the combined organic layers were dried over sodium sulfate, filtered, and concentrated under reduced pressure to give the title compound (25.6 g, 86% yield) as a white solid.
$^1$H NMR (CDCl$_3$) δ 7.25 (m); 6.9 (t); 6.4 (m); 6.3 (m); 6.1 (s); 5.0 (s); 3.5 (m); 2.5 (t).

Example 10

Preparation of 4-Nitrobenzenesulfonic Acid 2-[3-(Tritylamino)phenyl]ethyl Ester To a stirred solution of 2-[3-(tritylamino)phenyl]ethanol (5.00 g, 13.2 mmol) and triethylenediamine (2.22 g, 19.8 mmol) in DCM (52.7 mL) under nitrogen at 0° C. was added portion-wise p-nitrobenzenesulfonyl chloride (3.50 g, 15.8 mmol) over a period of 5 min. The resulting mixture stirred at 0° C. for 40 min and then saturated aqueous sodium bicarbonate solution (~50 mL) was added. The mixture was stirred at room temperature for 10 min and then the layers were separated. The aqueous layer was extracted with DCM (2×~50 mL) and the combined organic layers were dried over sodium sulfate, filtered, and concentrated under reduced pressure to give the title compound (7.44 g, 100% yield) as an orange-yellow foamy solid.

$^1$H NMR (CDCl$_3$) δ 8.20 (m); 7.70 (m); 7.30 (m); 6.70 (m); 6.30 (m); 6.10 (m); 5.30 (s); 5.00 (s); 4.00 (t); 3.20 (m); 2.60 (m).

Example 11

Preparation of 5-[(R)-2-{[2-(3-Aminophenyl)ethyl]benzylamino}-1-(tert-butyl-dimethylsilanyloxy)ethyl]-8-benzyloxy-1H-quinolin-2-one A stirred mixture of 4-nitrobenzenesulfonic acid 2-[3-(tritylamino)phenyl]ethyl ester (7.44 g, 13.2 mmol); 5-[(R)-2-benzylamino-1-(tert-butyldimethylsilanyloxy)ethyl]-8-benzyloxy-1H-quinolin-2-one (5.42 g, 10.5 mmol) (see, e.g., U.S. Patent Publication No. 2006/0035931 A1, published Feb. 16, 2006) and sodium bicarbonate (3.32 g, 39.5 mmol) in acetonitrile (26.4 mL) was heated at 75° C. under nitrogen for 18 h. The mixture was cooled to room temperature and the pH was adjusted to pH <2 with aqueous hydrochloric acid (1 N, ~40 mL). The mixture was stirred at room temperature for 1 h and then the pH of the mixture was adjusted to pH 7-8 with saturated aqueous sodium bicarbonate solution (~30 mL). Water (~50 mL) and EtOAc (~50 mL) were added and the layers were separated (a small amount of dilute aqueous sodium chloride solution was added to improve separation). The aqueous layer was extracted with EtOAc (2×30 mL) and the combined organic layers were dried over sodium sulfate, filtered, and concentrated under reduced pressure. The residue was purified by silica gel flash chromatography (30-60% of EtOAc in hexanes) to give the title compound (5.7 g, 68% yield) as a light yellow foamy solid.

$^1$H NMR (CDCl$_3$) δ 9.10 (s); 7.90 (br s); 7.40 (m); 7.20 (m); 7.10 (m); 7.00 (t); 6.90 (s); 6.50 (m); 6.30 (s); 5.20 (s); 4.80 (m); 3.60 (m); 2.80 (m); 2.60 (m); 0.80 (s); −0.2 (s).

Example 12

Preparation of 4-(tert-Butoxycarbonylmethylamino)butyric Acid

To a stirred mixture of 4-(methylamino)butyric acid hydrochloride (1.00 g, 6.51 mmol) and triethylamine (2.72 mL, 19.5 mmol) in DCM (60 mL) at room temperature was added di-tert-butyldicarbonate (1.56 g, 7.16 mmol). The resulting mixture was stirred for about 72 h. LC-MS showed product was present (Rt 4.11 min; m/z 216.2 [M+H]$^+$). DCM and water were added and the pH of the aqueous layer was adjusted to pH 4.5 to 6 with aqueous hydrochloric acid (1 M). The layers were separated and the organic layer was dried over sodium sulfate, filtered and concentrated under reduced pressure to give the title compound (1.5 g, 100% yield) as light yellow thick oil.

$^1$H NMR (CDCl$_3$) δ 3.28 (br s); 2.85 (s); 2.35 (t); 1.84 (t); 1.46 (s).

Example 13

Preparation of {3-[3-(2-{Benzyl-[(R)-2-(8-benzyloxy-2-oxo-1,2-dihydroquinolin-5-yl)-2-(tert-butyldimethylsilanyloxy)ethyl]amino}ethyl)phenylcarbamoyl]-propyl}methylcarbamic Acid tert-Butyl Ester To a stirred solution of 4-(tert-butoxycarbonylmethylamino)butyric acid (72.0 mg, 0.331 mmol); 5-[(R)-2-{[2-(3-aminophenyl)ethyl]benzylamino}-1-(tert-butyl-dimethylsilanyloxy)ethyl]-8-benzyloxy-1H-quinolin-2-one (210 mg, 0.331 mmol); 2,6-lutidine (46.5 μL, 0.398 mmol); and N-(3-dimethylaminopropyl)-N'-ethylcarbodiimide hydrochloride (69.8 mg, 0.364 mmol) in DMF (3 mL) at room temperature was added a solution of 1-hydroxy-7-azabenzotriazole in DMF (0.5 M, 0.729 mL, 0.364 mmol). The resulting mixture was stirred at room temperature overnight. LC-MS (Method 2-90) showed product was present (Rt 4.56 min; m/z 833.6 [M+H]$^+$). Water was added and this mixture was diluted with aqueous 10% lithium chloride solution and DCM. The layers were separated and the organic layer was washed with aqueous 10% lithium chloride solution (2×), dried over sodium sulfate, filtered and concentrated under reduced pressure. The residue was further concentrated under high vacuum to give the title compound (containing a minor amount of DMF), which was used in the next reaction without further purification.

Example 14

Preparation of N-[3-(2-{Benzyl-[(R)-2-(8-benzyloxy-2-oxo-1,2-dihydroquinolin-5-yl)-2-(tert-butyldimethylsilanyloxy)ethyl]amino}ethyl)phenyl]-4-methylaminobutyramide To a stirred solution of {3-[3-(2-{benzyl-[(R)-2-(8-benzyloxy-2-oxo-1,2-dihydroquinolin-5-yl)-2-(tert-butyldimethylsilanyloxy)ethyl]amino}ethyl)-phenylcarbamoyl]propyl}methylcarbamic acid tert-butyl ester (276 mg, 0.331 mmol) in DCM (3 mL) at room temperature was added trifluoroacetic acid (2 mL, 20 mmol) and the resulting mixture was stirred at room temperature overnight. LC-MS (Method 2-90) showed product was present (Rt 2.69 min; m/z 7.33.4 [M+H]$^+$). The reaction mixture was concentrated under reduced pressure and the residue was dissolved in DCM. This solution was washed with aqueous saturated sodium bicarbonate solution (2×), dried over sodium sulfate, filtered and concentrated under reduced pressure to give the title compound (249 mg, 100% yield) as a yellow-brown oil, which was used in the next reaction without further purification.

Example 15

Preparation of Biphenyl-2-ylcarbamic Acid 1-[2-({3-[3-(2-{Benzyl-[(R)-2-(8-benzyloxy-2-oxo-1,2-dihydroquinolin-5-yl)-2-(tert-butyldimethylsilanyloxy)ethyl]-amino}ethyl)phenylcarbamoyl]propyl}methylcarbamoyl)ethyl]piperidin-4-yl Ester To a stirred solution of 3-[4-(biphenyl-2-ylcarbamoyloxy)piperidin-1-yl]-propionic acid (127 mg, 0.344 mmol) and N-(3-dimethylaminopropyl)-N-ethylcarbodiimide hydrochloride (69.0 mg, 0.360 mmol) in DMF (5 mL) at room temperature was added a solution of 1-hydroxy-7-azabenzotriazole in DMF (0.5 M, 0.720 mL, 0.360 mmol). N-[3-(2-{Benzyl-[(R)-2-(8-benzyloxy-2-oxo-1,2-dihydroquinolin-5-yl)-2-(tert-butyldimethylsilanyloxy)ethyl]amino}ethyl)phenyl]-4-methylaminobutyramide (240 mg, 0.327 mmol) and 2,6-lutidine (114 μL, 0.982 mmol) were added and the resulting mixture was stirred overnight. LC-MS (Method 2-90) showed product was present (Rt 4.13 min; m/z 1083.7 [M+]). Water was added and this mixture was diluted with DCM. The layers were separated and the organic layer was washed with aqueous 10% lithium chloride solution (2×), dried over sodium sulfate, filtered and concentrated under reduced pressure. The residue was purified by silica gel flash chromatography (0-20% MeOH in DCM with 1% TEA) to give the title compound (258 mg, 72% yield) as a yellow oil.

Example 16

Preparation of Biphenyl-2-ylcarbamic Acid 1-(2-{[3-(3-{2-[(R)-2-(tert-Butyldimethylsilanyloxy)-2-(8-hydroxy-2-oxo-1,2-dihydroquinolin-5-yl)ethylamino]-ethyl}phenylcarbamoyl)propyl]methylcarbamoyl}ethyl)piperidin-4-yl Ester To a stirred solution of biphenyl-2-ylcarbamic acid 1-[2-({3-[3-(2-{benzyl-[(R)-2-(8-benzyloxy-2-oxo-1,2-dihydroquinolin-5-yl)-2-(tert-butyldimethylsilanyloxy)ethyl]-amino}ethyl)phenylcarbamoyl]propyl}methylcarbamoyl)ethyl]piperidin-4-yl ester (258 mg, 0.238 mmol) in MeOH (3 mL) at room temperature was added a solution of acetic acid in water (17.4 M, 41.4 μL, 0.720 mmol). The resulting solution was purged with nitrogen (3 cycles of vacuum following by dry nitrogen) and then palladium hydroxide (47 mg, 0.34 mmol) was added. This mixture was again purged with nitrogen and then with hydrogen (5×) and then stirred at room temperature under hydrogen (balloon with submerged needle) for 6 h. LC-MS (Method 2-90) showed product was present (Rt 3.71 min; m/z 903.6 [M+H]+). The reaction mixture was filtered through a membrane filter and the filtrate was concentrated under reduced pressure to give the title compound, which was used in the next reaction without further purification.

Example 17

Preparation of Biphenyl-2-ylcarbamic Acid 1-(2-{[3-(3-{2-[(R)-2-Hydroxy-2-(8-hydroxy-2-oxo-1,2-dihydroquinolin-5-yl)ethylamino]ethyl}phenylcarbamoyl)-propyl]methylcarbamoyl}ethyl)piperidin-4-yl Ester Ditrifluoroacetic Acid Salt (Compound I-7)

To a stirred solution of biphenyl-2-ylcarbamic acid 1-(2-{[3-(3-{2-[(R)-2-(tert-butyldimethylsilanyloxy)-2-(8-hydroxy-2-oxo-1,2-dihydroquinolin-5-yl)ethylamino]-ethyl}phenylcarbamoyl)propyl]methylcarbamoyl}ethyl)piperidin-4-yl ester (202 mg, 0.224 mmol in DCM (4 mL) at room temperature was added triethylamine trihydrofluoride (364 μL, 2.24 mmol) and the resulting mixture was stirred overnight. LC-MS (Method 2-90) showed product was present (Rt 2.77 min; m/z 789.6 [M+H]+). The reaction mixture was concentrated under reduced pressure and the residue was purified by HPLC to give the title compound (101.6 mg, 47% yield, 100% purity).

Example 18

Preparation of Methyl (3-Bromophenyl)acetate

A stirred solution of (3-bromophenyl)acetic acid (10.0 g, 0.0465 mol) and concentrated sulfuric acid (4.5 mL) in MeOH (230 mL) was heated at 40° C. for 16 h. The reaction mixture was concentrated under reduced pressure and the residue was mixed with water (50 mL) and DCM (100 mL). The layers were separated and the organic layer was concentrated under reduced pressure. The residue was purified by silica gel flash chromatography (0-10% EtOAc/hexanes) to give the title compound (19.8 g, 91% yield) as a colorless oil.

LC-MS (Method 10-90): Rt 3.36 min; m/z 300.4 [M+H]+; 229.6 [M+]. $^1$H NMR (CD$_3$OD) δ 7.48 (s, 1H); 7.44 (d, 1H); 7.26-7.25 (m, 2H); 3.71 (s, 3H); 3.66 (s, 2H).

Example 19

Preparation of Methyl [3-(2-Oxopropyl)phenyl]acetate

A stirred mixture of methyl (3-bromophenyl)acetate (19.7 g, 86.0 mmol), tributyltin methoxide (37.1 mL, 129 mmol), isopropenyl acetate (14.2 mL, 129 mmol), palladium acetate (961 mg, 4.28 mmol), and tri-o-tolylphosphine (2.63 g, 8.64 mmol) in toluene (70 mL) was heated at 100° C. for 6 h. Aqueous potassium fluoride solution (4 M, 120 mL) and EtOAc (200 mL) were added and the resulting mixture was stirred overnight. The mixture was then filtered through Celite and the layers were separated. The organic layer was washed with water and then concentrated under reduced pressure. The residue was purified by silica gel flash chromatography (0-8% MeOH in DCM) to give the title compound (11.8 g, 66% yield).

LC-MS (Method 10-90): Rt 4.24 min; m/z 207.3 [M+H]+.

Example 20

Preparation of Methyl {3-[(S)-2-((S)-1-Phenylethylamino)propyl]phenyl}acetate Hydrochloride Salt A mixture of methyl [3-(2-oxopropyl)phenyl]acetate (2.31 g, 11.2 mmol), (S)-1-phenylethylamine (3.4 mL, 27.0 mmol),

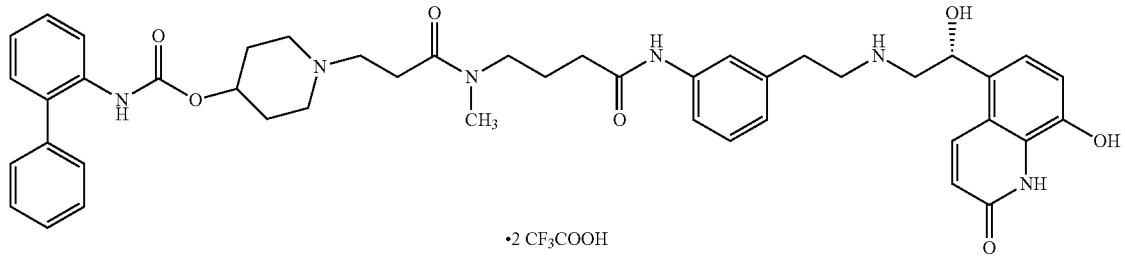 [SMILES: CN(CCCC(=O)Nc1cccc(CCNC[C@H](O)c2ccc(O)c3[nH]c(=O)ccc23)c1)C(=O)CCN1CCC(OC(=O)Nc2ccccc2-c2ccccc2)CC1]

·2 CF$_3$COOH sodium triacetoxyborohydride (14 g, 68.0 mmol), and magnesium sulfate (3.2 g, 27.0 mmol) in DCM (69 mL) was stirred overnight. The reaction mixture was cooled to 0° C. and saturated aqueous sodium bicarbonate solution (150 mL) was added until effervescence stopped. The layers were separated and the aqueous layer was extracted with DCM (70 mL). The combined organic layers were dried over sodium sulfate, filtered and concentrated under reduced pressure. The residue was purified by silica gel flash chromatography (0-10% MeOH in DCM). Aqueous hydrochloric acid (6 N, 2 mL) was added to the product to form the hydrochloride salt. MeOH (50 mL) was added and the resulting mixture was concentrated under reduced pressure. This procedure was repeated and then a minimum amount of MeOH (5 mL) was added to completely dissolve the solid. Diisopropyl ether (9 mL) was added and the resulting mixture was left standing at room temperature for 2 h. The resulting precipitate was collected by filtration and washed with ether to give the title compound (2.85 g; 81% yield; 10:1 de of S,S) as a white solid.

LC-MS (Method 2-90): Rt 2.28 min; m/z 312.2 [M+H]$^+$.
$^1$H NMR (CD$_3$OD) δ 7.71-7.69 (m, 4H); 7.45 (t, 1H); 7.35 (t, 1H); 7.20-7.17 (m, 3H); 4.80-4.76 (m, 1H); 3.85 (s, 3H); 3.81 (s, 2H); 3.42-3.40 (m, 1H); 2.80 (t, 2H); 1.86 (d, 3H); 1.37 (d, 3H).

Example 21

Preparation of Methyl [3-((S)-2-Aminopropyl)phenyl]acetate

A stirred solution of methyl {3-((S)-2-[((S)-1-phenylethylamino)propyl]-phenyl}acetate hydrochloride salt (1.12 g, 3.60 mmol), ammonium formate (1.16 g, 257 mmol), and palladium hydroxide (0.30 g, 2.1 mmol) in EtOH (40 mL) was heated at 75° C. for 1 h. The reaction mixture was filtered through Celite and the filter cake was washed with EtOAc (2×50 mL). The filtrate was concentrated under reduced pressure and the residue was dissolved in DCM (50 mL) and 20% aqueous ammonia solution (50 mL). The layers were separated and the aqueous layer was extracted with DCM. The combined organic layers were dried over sodium sulfate, filtered and concentrated under reduced pressure to give the title compound (437 mg, 58% yield) as a colorless oil.

LC-MS (Method 2-90): Rt 1.18 min; m/z 208.4[M+H]$^+$.
$^1$H NMR (CD$_3$OD) δ 7.43 (t, 1H); 7.29-7.25 (m, 3H); 3.85 (s, 3H); 3.81 (s, 2H); 3.31-3.23 (m, 1H); 2.85-2.75 (m, 2H); 1.26 (d, 3H).

Example 22

Preparation of (3-{(S)-2-[(R)-2-(8-Benzyloxy-2-oxo-1,2-dihydroquinolin-5-yl)-2-(tert-butyldimethylsilanyloxy)ethylamino]propyl}phenyl)acetic Acid Methyl Ester A solution of [3-((S)-2-aminopropyl)phenyl]acetic acid methyl ester (632 mg, 3.05 mmol) and triethylamine (1.27 mL, 9.15 mmol) in N-methylpyrrolidinone (3.4 mL, 35 mmol) was added to 8-benzyloxy-5-[(R)-2-bromo-1-(tert-butyldimethylsilanyloxy)-ethyl]-1H-quinolin-2-one (1.5 g, 3.0 mmol) (see, e.g., U.S. Patent Publication No. 2006/0035931 A1, published Feb. 16, 2006). The resulting mixture was microwaved (300 watts) at 100° C. for 1.5 h. The mixture was then diluted with EtOAc (20 mL) and this solution was washed repeatedly with brine (100 mL), dried over sodium sulfate, filtered and concentrated under reduced pressure. The residue was purified by silica gel flash chromatography (0-10% MeOH in DCM) to give the title compound (400 mg, 20% yield) as a yellow oil.

LC-MS (Method 2-90): Rt 2.79 min; m/z 615.4[M+H]$^+$.

Example 23

Preparation of (3-{(S)-2-[(R)-2-(8-Benzyloxy-2-oxo-1,2-dihydroquinolin-5-yl)-2-(tert-butyldimethylsilanyloxy)ethylamino]propyl}phenyl)acetic Acid To a solution of (3-{(S)-2-[(R)-2-(8-benzyloxy-2-oxo-1,2-dihydroquinolin-5-yl)-2-(tert-butyldimethylsilanyloxy)ethylamino]propyl}phenyl)acetic acid methyl ester (810 mg, 1.3 mmol) in a 3:2:1 mixture of THF/MeOH/water (4 mL) was added lithium hydroxide (158 mg, 6.59 mmol). The resulting mixture was stirred at room temperature for 3 hours and then acidified to pH 6 with concentrated aqueous hydrochloric acid. This mixture was concentrated under reduced pressure to give a yellow solid (307 mg, 39% yield), which was used in the next reaction without further purification.

LC-MS (Method 2-90): Rt 3.10 min; m/z 601.4[M+H]$^+$.

Example 24

Preparation of (3-{(S)-2-[(R)-2-(tert-Butyldimethylsilanyloxy)-2-(8-hydroxy-2-oxo-1,2-dihydroquinolin-5-yl)ethylamino]propyl}phenyl)acetic Acid A solution of (3-{(S)-2-[(R)-2-(8-benzyloxy-2-oxo-1,2-dihydroquinolin-5-yl)-2-(tert-butyldimethylsilanyloxy)ethylamino]propyl}phenyl)acetic acid (~1.3 mmol) in EtOH (8 mL) was purged with dry nitrogen and then palladium on carbon (10%, ~50% water, Degussa type, 300 mg) was added. This mixture was purged with hydrogen and then stirred under an atmosphere of hydrogen (balloon) for 1 h. The mixture was then filtered through Celite and the filter bed washed with MeOH (20 mL) and EtOAc (20 mL). The filtrate was concentrated under reduced pressure and the residue was purified by silica gel flash chromatography (0-20% MeOH in DCM) to give the title compound (300 mg, 40% yield) as a yellow solid.

LC-MS (Method 2-90): Rt 2.67 min; m/z 511.6 [M+H]$^+$.

Example 25

Preparation of [3-(9H-Fluoren-9-ylmethoxycarbonylamino)propyl]methylcarbamic Acid tert-Butyl Ester To a stirred solution of N-(3-aminopropyl)-N-methylcarbamic acid tert-butyl ester (2.00 g, 10.6 mmol) and sodium carbonate (2.81 g, 26.6 mmol) in water (7 mL) at 0° C. was added a solution of 9-fluorenylmethyl chloroformate (2.75 g, 10.6 mmol) in 1,4-dioxane (5 mL). The resulting mixture was stirred at room temperature for 2 h and then poured into water (10 mL). This mixture was extracted with diethyl ether (2×50 mL) and the combined organic layers were dried over sodium sulfate, filtered and concentrated under reduced pressure to afford a clear oil. The oil was purified by silica gel flash chromatography (0-70% EtOAc in hexanes) to give the title compound (4.24 g, 77% yield) as a clear oil (product contained a minor impurity, but was used without further purification).

LC-MS (Method 2-90): Rt 4.05 min; m/z 411.2[M+H]$^+$.
$^1$H NMR (CD$_3$OD) δ 7.96 (d, 2H); 7.81 (d, 2H), 7.56 (t, 2H);

7.48 (t, 2H); 4.55 (d, 2H); 4.37 (t, 1H); 3.41 (t, 2H); 3.27 (t, 2H); 3.01 (s, 3H); 1.89-1.85 (m, 2H); 1.61 (s, 9H).

Example 26

Preparation of (3-Methylaminopropyl)carbamic Acid 9H-Fluoren-9-ylmethyl Ester Hydrochloride Salt To a stirred solution of [3-(9H-fluoren-9-ylmethoxycarbonylamino)propyl]-methylcarbamic acid tert-butyl ester (4.24 g, 10.3 mmol) in EtOAc (8 mL) was slowly added concentrated hydrochloric acid (2 mL, 60 mmol) and the resulting mixture was stirred at room temperature overnight. The mixture was concentrated under reduced pressure to give the title compound (3.21 g, 78% yield) as a white solid.

LC-MS (Method 2-90): Rt 2.32 min; m/z 311.4[M+H]$^+$.
$^1$H NMR (CD$_3$OD) δ 7.82 (d, 2H); 7.66 (d, 2H), 7.42 (t, 2H); 7.34 (t, 2H); 4.45 (d, 2H); 4.12 (t, 1H); 3.23 (t, 2H); 2.99 (t, 2H); 2.71 (s, 3H); 1.88-1.83 (m, 2H).

Example 27

Preparation of Biphenyl-2-ylcarbamic Acid 1-(2-{[3-(9H-Fluoren-9-ylmethoxycarbonylamino)propyl] methylcarbamoyl}ethyl)piperidin-4-yl Ester To a stirred mixture of 3-[4-(biphenyl-2-ylcarbamoyloxy) piperidin-1-yl]-propionic acid (2.8 g, 7.6 mmol) and N,N-diisopropylethylamine (2.6 mL, 15 mmol) in DMF (31 mL) was added 2-chloro-1-methylpyridinium iodide (3.9 g, 15 mmol). Once the solids had dissolved, (3-methylaminopropyl)carbamic acid 9H-fluoren-9-ylmethyl ester hydrochloride salt (2.63 g, 7.58 mmol) was added and the resulting mixture was stirred at room temperature until essentially complete by HPLC and LCMS. The mixture was then concentrated under reduced pressure to remove most of the DMF and the residue was dissolved in DCM (30 mL). This mixture was washed with water (3×20 mL) and brine (3×20 mL), dried over sodium sulfate, filtered and concentrated under reduced pressure. The residue was purified by silica gel flash chromatography (0-20% MeOH in DCM) to give the title compound (5.0 g, 97% yield) as a white solid.

LC-MS (Method 2-90): Rt 3.24 min; m/z 661.4 [M+H]$^+$.

Example 28

Preparation of Biphenyl-2-ylcarbamic Acid 1-{2-[(3-Aminopropyl)-methylcarbamoyl]ethyl}piperidin-4-yl Ester To biphenyl-2-ylcarbamic acid 1-(2-{[3-(9H-fluoren-9-ylmethoxycarbonyl-amino)propyl]methylcarbamoyl}ethyl)piperidin-4-yl ester (2.2 g, 3.3 mmol) was added a 10% solution of piperidine (0.31 g, 3.3 mmol) in DCM (3.2 mL) and the resulting mixture was shaken at room temperature for 1 h. The mixture was concentrated under reduced pressure and the residue was dissolved in DCM (100 mL). This mixture was washed with water (2×20 mL) and then extracted with ammonium chloride (1 N, 2×20 mL). The layers were separated and DCM was added to the aqueous layer. The aqueous layer was made basic by addition of aqueous potassium hydroxide (1 N) and the layers were separated. The organic layer was washed with aqueous potassium hydroxide (1 N, 2×20 mL) and brine (1×20 mL), dried over sodium sulfate, filtered and concentrated under reduced pressure to give the title compound (1.0 g, 66% yield) as a clear oil.

LC-MS (Method 2-90): Rt 1.85 min; m/z 439.4 [M+H]$^+$.

Example 29

Preparation of Biphenyl-2-ylcarbamic Acid 1-[2-({3-[2-(3-{(S)-2-[(R)-2-(tert-Butyldimethylsilanyloxy)-2-(8-hydroxy-2-oxo-1,2-dihydroquinolin-5-yl)ethylamino]propyl}phenyl)acetylamino] propyl}methylcarbamoyl)ethyl]piperidin-4-yl Ester A mixture of (3-{(S)-2-[(R)-2-(tert-butyldimethylsilanyloxy)-2-(8-hydroxy-2-oxo-1,2-dihydroquinolin-5-yl)ethylamino]propyl}phenyl)acetic acid (135 mg, 0.264 mmol); 2-chloropyridium triflate on Wang resin (polymer-supported Mukaiyama reagent) (1.19 mmol/g loading; 635 mg, 0.775 mmol) and N,N-diisopropylethylamine (132 μL, 0.755 mmol) in DMF (4.78 mL) was stirred at room temperature for 30 min. Biphenyl-2-ylcarbamic acid 1-{2-[(3-aminopropyl)methylcarbamoyl]ethyl}piperidin-4-yl ester (122 mg, 0.278 mmol) was added and this mixture was stirred at room temperature overnight. The mixture was filtered and the resin was washed with DCM (4 mL), MeOH (4 mL) and THF (4 mL). The filtrate was concentrated under reduced pressure and the residue was dissolved in DCM. This solution was washed with water (2×10 mL), saturated aqueous sodium bicarbonate (2×10 mL) and brine (1×10 mL); and then dried over sodium sulfate, filtered and concentrated under reduced pressure. The residue was purified by silica gel flash chromatography (0-20% MeOH in DCM) to give the title compound (59 mg, 24% yield) as a white solid.

LC-MS (Method 2-90): Rt 4.35 min; m/z 931.7 [M+H]$^+$.

Alternatively, this reaction can be conducted using a combination of EDC and HOBt as the coupling reagents.

Example 30

Preparation of Biphenyl-2-ylcarbamic Acid 1-[2-({3-[2-(3-{(S)-2-[(R)-2-Hydroxy-2-(8-hydroxy-2-oxo-1, 2-dihydroquinolin-5-yl)ethylamino]propyl}phenyl) acetylamino]-propyl}methylcarbamoyl)ethyl] piperidin-4-yl Ester Ditrifluoroacetic Acid Salt (Compound I-13)

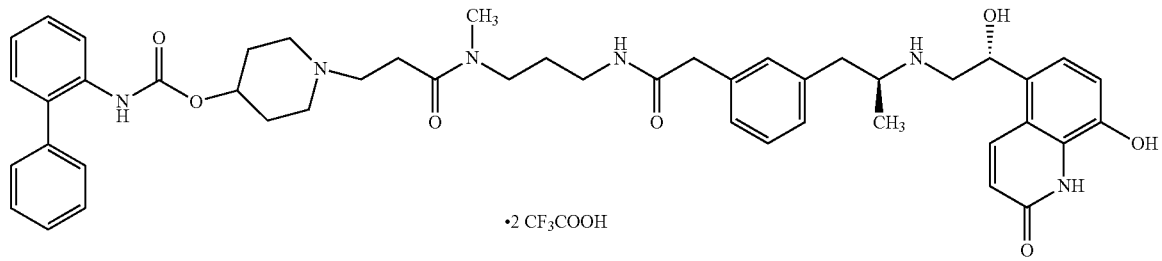 [SMILES: C[C@@H](Cc1cccc(CC(=O)NCCCN(C)C(=O)CCN2CCC(OC(=O)Nc3ccccc3-c3ccccc3)CC2)c1)NC[C@H](O)c1ccc(O)c2[nH]c(=O)ccc12]

A solution of biphenyl-2-ylcarbamic acid 1-[2-({3-[2-(3-{(S)-2-[(R)-2-(tert-butyl-dimethylsilanyloxy)-2-(8-hydroxy-2-oxo-1,2-dihydroquinolin-5-yl)ethylamino]propyl}-phenyl)acetylamino]propyl}methylcarbamoyl)ethyl]piperidin-4-yl ester (59 mg, 0.063 mmol) and triethylamine trihydrofluoride (10.3 µL, 0.0634 mmol) in DCM (1 mL) was microwaved (300 watts) at 80° C. for 20 min. The reaction mixture was then concentrated under reduced pressure and the residue was purified by HPLC (Method 10-50) to give the title compound (35.2 mg, 52% yield).

LC-MS (Method 2-90): Rt 2.16 min; m/z 817.6[M+H]$^+$.

Example 31

Preparation of Methyl 5-Methylaminopentanoate Hydrochloride

A stirred solution of 1-methyl-2-piperidinone (4.40 mL, 40.0 mmol) in aqueous sodium hydroxide (4 M, 11.0 mL, 44.0 mmol) was heated at 100° C. for 15 h. The reaction mixture was cooled to room temperature and then acidified to pH 2 with concentrated hydrochloric acid. The mixture was then concentrated under reduced pressure to give crude 5-methylaminopentanoic acid as a pinkish white solid. To the crude 5-methylaminopentanoic acid was added MeOH (40.0 mL, 987 mmol) and concentrated hydrochloric acid (0.33 mL, 4.0 mmol). The resulting cloudy solution was heated at 60° C. for 39 h at which time LC-MS showed remaining starting material. Additional concentrated hydrochloric acid (0.33 mL, 4.0 mmol) was added and the resulting mixture was heated at 60° C. for 33 h and then at 65° C. for an additional 24 h. LC-MS showed remaining starting material. The reaction mixture was concentrated under reduced pressure and a solution of hydrogen chloride in MeOH (1.25 M) was added to the residue. The resulting mixture was heated at 60° C. for 72 h at which time no remaining starting material was observed by LC-MS. The reaction mixture was partially concentrated under reduced pressure and the solid material that formed was removed by filtration, washing with MeOH. The filtrate was then concentrated under reduced pressure to provide methyl 5-methylaminopentanoate hydrochloride (7.57 g, 100% yield) as a light yellow solid.

LC-MS (Method 2-90): Rt 1.10 min; m/z 146.4 [M+H]$^+$.
$^1$H NMR (CD$_3$OD) δ 4.86 (s), 3.66 (s), 3.30 (t), 3.00 (t), 2.69 (s), 2.41 (t), 1.71 (m).

Example 32

Preparation of 5-({3-[4-(Biphenyl-2-ylcarbamoyloxy)piperidin-1-yl]propionyl}methylamino)pentanoic Acid Methyl Ester A mixture of methyl 5-methylaminopentanoate hydrochloride (7.27 g, 40.0 mmol), 3-[4-(biphenyl-2-ylcarbamoyloxy)piperidin-1-yl]propionic acid (13.3 g, 36.0 mmol) and 1-hydroxy-7-azabenzotriazole (5.14 g, 37.8 mmol) in DCM (160 mL) and 2,6-lutidine (12.5 mL, 108 mmol) was stirred at room temperature for 3 h. N-(3-Dimethylaminopropyl)-N-ethylcarbodiimide hydrochloride (10.4 g, 54.0 mmol) was added and the resulting mixture was stirred at room temperature for 2 h. A saturated aqueous sodium bicarbonate solution (~100 mL) was added and the layers were separated. The aqueous layer was extracted with DCM (50 mL) and the organic layers were combined, dried over sodium sulfate, filtered and concentrated under reduced pressure. The residue was purified by silica gel flash chromatography (30-100% EtOAc in hexanes; then 2-10% MeOH in DCM) to give the title compound (12.38 g, 69% yield) as a light yellow thick oil/white solid.

LC-MS (Method 2-90): Rt 2.43 min; m/z 496.6 [M+H]$^+$.
$^1$H NMR (CDCl$_3$) δ 8.10 (d, 1H), 7.40 (m, 6H), 7.20 (m, 2H), 6.58 (s, 1H), 4.74 (m, 1H), 3.66 (d, 3H), 3.37 (t, 1H), 3.29 (m, 1H), 2.97 (s, 2H), 2.91 (s, 1H), 2.70 (m, 4H), 2.49 (m, 2H), 2.34 (m, 4H), 1.92 (m, 2H), 1.60 (m, 5H).

Example 33

Preparation of 5-({3-[4-(Biphenyl-2-ylcarbamoyloxy)piperidin-1-yl]propionyl}methylamino)pentanoic Acid To a mixture of 5-({3-[4-(biphenyl-2-ylcarbamoyloxy)piperidin-1-yl]propionyl}-methylamino)pentanoic acid methyl ester (10.21 g, 20.60 mmol), tert-butyl alcohol (20 mL) and water (20 mL) was added a 1:1 mixture of LiOH:water (1.97 g, 41.2 mmol). The resulting mixture was stirred at room temperature for 4 h and then the pH of the mixture was adjusted to about pH 2 using aqueous hydrochloric acid (1 N). The aqueous layer was extracted with DCM (2×~80 mL) and the organic layers were combined, dried over sodium sulfate, filtered, and concentrated under reduced pressure to give the title compound (12.23 g, quantitative) as an off-white foamy solid (containing residual tert-butyl alcohol).

LC-MS (Method 2-90): Rt 2.32 min; m/z 482.4 [M+H]$^+$.

Example 34

Preparation of 2-(4-Nitrophenyl)-1,3-dioxolane

A stirred solution of p-nitrobenzaldehyde (101.5 g, 672 mmol), ethylene glycol (112 mL) and p-toluenesulfonic acid (12.8 g, 67.2 mmol) in toluene (800 mL) was heated in flask equipped with a Dean-Stark trap at 120° C. for 4 h. After cooling to room temperature, the reaction mixture was concentrated under reduced pressure. To the residue was added saturated aqueous sodium bicarbonate (800 mL) and this mixture was stirred at room temperature for 15 min. The resulting solid was isolated by filtration and dried under vacuum to give the title compound (121.8 g, 92% yield) as a yellow solid.

$^1$H NMR (DMSO-d$_6$): δ=8.12 (d, 2H), 7.59 (d, 2H), 5.78 (s, 1H), 3.8-4.0 (m, 4H).

Example 35

Preparation of 4-(1,3-Dioxolan-2-yl)phenylamine

To a mixture of platinum dioxide (227 mg, 1.00 mmol) and sodium bicarbonate (420 mg, 5.00 mmol) under dry nitrogen was added a solution of 2-(4-nitrophenyl)-1,3-dioxolane (976 mg, 5.00 mmol) in EtOH (30.0 mL). The reaction mixture was bubbled with hydrogen for 15 min and then stirred under a hydrogen atmosphere (balloon) for 2 h. The reaction mixture was then filtered through a pad of Celite washing with MeOH. The filtrate was concentrated under reduced pressure to give the title compound (0.80 g, 96% yield).

Example 36

Preparation of Biphenyl-2-ylcarbamic Acid 1-(2-{[4-(4-(1,3-Dioxolan-2-yl)-phenylcarbamoyl)butyl]methylcarbamoyl}ethyl)piperidin-4-yl Ester To a stirred solution of 5-({3-[4-(biphenyl-2-ylcarbamoyloxy)piperidin-1-yl]-propionyl}methylamino)pentanoic acid (2.33 g, 4.84 mmol), 4-(1,3-dioxolan-2-yl)phenylamine (800 mg, 5 mmol) and N,N-diisopropylethylamine (1.26 mL, 7.26 mmol) in DCM (48.4 mL) was added 1-hydroxy-7-azabenzotriazole (692 mg, 5.08 mmol) and N-(3-dimethylaminopropyl)-N-ethylcarbodiimide hydrochloride (1.39 g, 7.26 mmol). The resulting mixture was stirred at room temperature overnight. The reaction mixture was then washed with saturated aqueous sodium bicarbonate solution, dried over sodium sulfate, filtered and concentrated under reduced pressure to give the title compound (3.04 g, 100% yield) as a yellow solid.

LC-MS (Method 10-70): Rt 2.67 min; m/z 629.6 [M+H]$^+$.

The solid was purified by silica gel flash chromatography (0-30% MeOH in DCM+0.5% NH$_4$OH) to give the title compound (3.60 g, 82% yield) as a yellow solid.

LC-MS (Method 10-70): Rt 2.72 min; m/z 903.8 [M+H]$^+$.

Example 39

Preparation of Biphenyl-2-ylcarbamic Acid 1-(2-{[4-(4-{[(R)-2-hydroxy-2-(8-hydroxy-2-oxo-1,2-dihydroquinolin-5-yl)ethylamino]methyl}phenylcarbamoyl)-butyl]methylcarbamoyl}ethyl)piperidin-4-yl Ester Ditrifluoroacetic Acid Salt (Compound I-14)

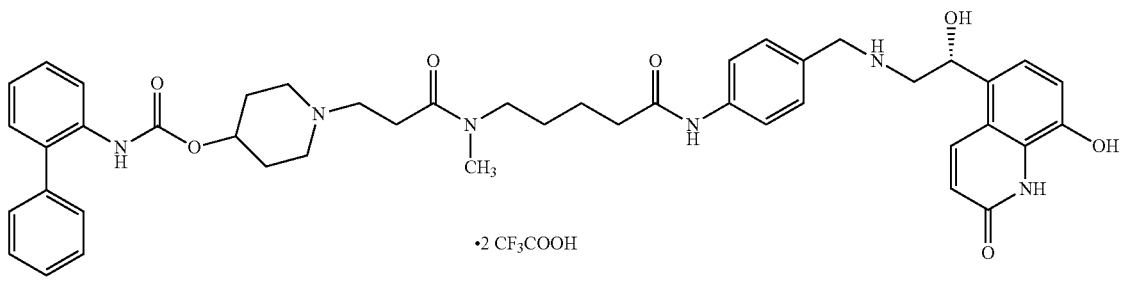 [SMILES: CN(CCCCC(=O)Nc1ccc(CNC[C@H](O)c2ccc(O)c3[nH]c(=O)ccc23)cc1)C(=O)CCN1CCC(OC(=O)Nc2ccccc2-c2ccccc2)CC1]

Example 37

Preparation of Biphenyl-2-ylcarbamic Acid 1-(2-{[4-(4-Formylphenylcarbamoyl)butyl]methylcarbamoyl}ethyl)piperidin-4-yl Ester A stirred mixture of biphenyl-2-ylcarbamic acid 1-(2-{[4-(4-(1,3-dioxolan-2-yl)phenylcarbamoyl)butyl]methylcarbamoyl}ethyl)piperidin-4-yl ester (3.04 g, 4.84 mmol) in aqueous hydrochloric acid (1 M, 10 mL) and acetonitrile (10 mL) was heated at 50° C. for 2 h. The reaction mixture was concentrated under reduced pressure and saturated aqueous sodium bicarbonate solution and DCM were added to the residue. The layers were separated and the organic layer was dried over sodium sulfate, filtered and concentrated under reduced pressure to give the title compound (2.83 g, 100% yield).

LC-MS (Method 10-70): Rt 2.67 min; m/z 585.4 [M+H]$^+$.

Example 38

Preparation of Biphenyl-2-ylcarbamic Acid 1-(2-{[4-(4-{[(R)-2-(tert-butyldimethyl-silanyloxy)-2-(8-hydroxy-2-oxo-1,2-dihydroquinolin-5-yl)ethylamino]methyl}-phenylcarbamoyl)butyl]methylcarbamoyl}ethyl)piperidin-4-yl Ester To a stirred solution of biphenyl-2-ylcarbamic acid 1-(2-{[4-(4-formyl-phenylcarbamoyl)butyl]methylcarbamoyl}ethyl)piperidin-4-yl ester (2.83 g, 4.84 mmol) and 5-[(R)-2-amino-1-(tert-butyldimethylsilanyloxy)ethyl]-8-hydroxy-1H-quinolin-2-one acetic acid salt (1.91 g, 4.84 mmol) in a 1:1 mixture of MeOH:DCM (40.0 mL, 312 mmol) was added sodium triacetoxyborohydride (3.08 g, 14.5 mmol). The reaction mixture was stirred at room temperature for 2 h and then the layers were separated. The organic layer was washed with saturated aqueous sodium bicarbonate solution, dried over sodium sulfate, filtered and concentrated under reduced pressure to give a yellow solid.

To a stirred solution of biphenyl-2-ylcarbamic acid 1-(2-{[4-(4-{[(R)-2-(tert-butyldimethylsilanyloxy)-2-(8-hydroxy-2-oxo-1,2-dihydroquinolin-5-yl)ethylamino]methyl}phenylcarbamoyl)butyl]methylcarbamoyl}ethyl)piperidin-4-yl ester (3.60 g, 3.98 mmol) in a 9:1 mixture of DCM:DMF (32.9 mL) was added triethylamine trihydrofluoride (1.95 mL, 12.0 mmol). The resulting mixture was stirred at room temperature overnight and then concentrated under reduced pressure. The residue was purified by HPLC (Method 10-70) to give the title compound (1.90 g, 46% yield) as a white solid.

LC-MS (Method 10-70): Rt 2.12 min; m/z 789.6 [M+H]$^+$.

Example 40

Preparation of Dibenzyl-(4-iodo-2,5-dimethylphenyl)amine

A mixture of 2,5-dimethyl-4-iodoaniline (6.44 g, 26.1 mmol), benzyl bromide (11.50 g, 67.24 mmol) and potassium carbonate (8.20 g, 59.3 mmol) in EtOH (100 mL) was stirred at 50° C. for 12 h. The reaction mixture was then concentrated under reduced pressure. The residue (a purple solid) was mixed with DCM and this mixture was filtered using vacuum. The filtrate was purified by silica gel flash chromatography (0-5% MeOH in DCM) to give the title compound (9.35 g, 83% yield) as an oil.

LC-MS (Method 10-90): Rt 3.99 min; m/z 428.4 [M+H]$^+$.

Example 41

Preparation of 4-Dibenzylamino-2,5-dimethylbenzaldehyde

To a stirred solution of dibenzyl-(4-iodo-2,5-dimethylphenyl)amine (9.35 g, 21.9 mmol) in toluene (100 mL) under nitrogen at −15° C. was added n-butyllithium in hexanes (1.6 M, 20.5 mL, 32.8 mmol) dropwise via syringe over a 30 min period. The resulting mixture was stirred at −15° C. for 15 min and then N,N-dimethylformamide (1.86 mL, 24.1 mmol) was added dropwise over a 10 min period. After 2 h, aqueous hydrochloric acid (1 M, 46.6 mL) and brine (30 mL) were added and the resulting mixture was stirred for 15 min. The layers were separated and the organic layer was extracted with brine, dried over magnesium sulfate, filtered and concentrated under reduced pressure. The residue was purified by silica gel flash chromatography (0-50% DCM in hexanes) to give the title compound (3.60 g, 49% yield) as a clear oil.

LC-MS (Method 10-90): Rt 3.76 min; m/z 330.4 [M+H]$^+$.

Example 42

Preparation of Dibenzyl-[4-(1,3-dioxolan-2-yl)-2,5-dimethylphenyl]amine

To a stirred solution of 4-dibenzylamino-2,5-dimethylbenzaldehyde (3.60 g, 10.9 mmol) in toluene (35.0 mL) under nitrogen was added 1,2-ethanediol (1.83 mL, 32.8 mmol) and p-toluenesulfonic acid (451 mg, 2.62 mmol). The reaction mixture was heated at 80° C. overnight. TLC (3:1 hexanes: EtOAc) showed a ~50:50 mixture of product and starting material. Magnesium sulfate (1.32 g, 10.9 mmol) was added and stirring was continued for 6 h. The reaction mixture was then filtered and concentrated under reduced pressure to give title compound (3.19 g, 78% yield) as an oil.

Example 43

Preparation of (4-Amino-2,5-dimethylphenyl)methanol

A stirred solution of dibenzyl-[4-(1,3-dioxolan-2-yl)-2,5-dimethylphenyl]amine (2.00 g, 5.35 mmol) in EtOH (14.0 mL) and EtOAc (7.00 mL) was flushed with nitrogen for 3 min and then sodium bicarbonate (0.200 g, 2.38 mmol) and palladium on activated carbon (10 wt. %, ~50% water; 0.800 g, 0.360 mmol) were added. The reaction mixture was flushed with hydrogen gas for 3 min and then stirred under a hydrogen atmosphere (balloon) for 3 h. The mixture was then filtered through a pad of Celite and the pad washed with MeOH (10 mL). The filtrate was concentrated under reduced pressure to give the title compound, which was used without any further purification.

Example 44

Preparation of Biphenyl-2-ylcarbamic Acid 1-(2-{[3-(4-Hydroxymethyl-2,5-dimethylphenylcarbamoyl) propyl]methylcarbamoyl}ethyl)piperidin-4-yl Ester A solution of 5-({3-[4-(biphenyl-2-ylcarbamoyloxy)piperidin-1-yl]propionyl}-methylamino)pentanoic acid (1.19 g, 2.46 mmol); (4-amino-2,5-dimethylphenyl)-methanol (372 mg, 2.46 mmol) and N,N-diisopropylethylamine (858 µL, 4.93 mmol) in DCM (18.5 mL) was stirred at room temperature for 30 min. N-(3-Dimethylaminopropyl)-N-ethylcarbodiimide hydrochloride (708 mg, 3.69 mmol) was added and the resulting mixture was stirred at room temperature for 3 h. Saturated aqueous sodium bicarbonate solution (5 mL) was added and this mixture was extracted with DCM (2×2 mL). The combined organic layers were dried over sodium sulfate, filtered and concentrated under reduced pressure. The residue was purified by silica gel flash chromatography (0-10% MeOH in DCM) to give the title compound (460 mg, 31% yield) as a yellow oil.

LC-MS (Method 10-90): Rt 2.53 min; m/z 599.4 [M+H]$^+$.

Example 45

Preparation of Biphenyl-2-ylcarbamic Acid 1-(2-{[4-(4-Formyl-2,5-dimethyl-phenylcarbamoyl)butyl] methylcarbamoyl}ethyl)piperidin-4-yl Ester To a stirred solution of biphenyl-2-ylcarbamic acid 1-(2-{ [4-(4-hydroxymethyl-2,5-dimethylphenylcarbamoyl)butyl] methylcarbamoyl}ethyl)piperidin-4-yl ester (0.460 g, 0.748 mmol) and dimethyl sulfoxide (0.531 mL, 7.48 mmol) in DCM (2.58 mL) at 0° C. was added N,N-diisopropylethylamine (0.65 mL, 3.7 mmol). Sulfur trioxide pyridine complex (0.357 g, 2.24 mmol) was added and the resulting mixture was stirred at 0° C. for 1 h. Water (3 mL) was added and the layers were separated. The organic layer was dried over sodium sulfate and filtered to give the title compound in a DCM solution, which was used immediately in the next reaction.

LC-MS (Method 10-90): Rt 2.44 min; m/z 613.4 [M+H]$^+$.

Example 46

Preparation of Biphenyl-2-ylcarbamic Acid 1-(2-{[4-(4-{[(R)-2-(tert-butyldimethyl-silanyloxy)-2-(8-hydroxy-2-oxo-1,2-dihydroquinolin-5-yl)-ethylamino] methyl}-2,5-dimethylphenylcarbamoyl)butyl] methylcarbamoyl}ethyl)piperidin-4-yl Ester To the stirred solution of biphenyl-2-ylcarbamic acid 1-(2-{[4-(4-formyl-2,5-dimethylphenyl carbamoyl)butyl] methylcarbamoyl}ethyl)piperidin-4-yl ester (~0.748 mmol) in DCM from the previous reaction was added 5-[(R)-2-amino-1-(tert-butyl-dimethylsilanyloxy)ethyl]-8-hydroxy-1H-quinolin-2-one acetic acid salt (0.295 g, 0.748 mmol) in 1:1 MeOH:DCM (3.0 mL). The resulting mixture was stirred at room temperature for 30 min and then sodium triacetoxyborohydride (0.476 g, 2.24 mmol) was added and stirring was continued at room temperature for 4 h. Aqueous NaOH (1 M, 3 mL) and DCM (3 mL) were added and the layers were separated. The organic layer was dried over sodium sulfate, filtered and concentrated under reduced pressure. The residue was purified by silica gel flash chromatography (0-15% MeOH in DCM) to give the title compound (420 mg, 60% yield) as a yellow solid.

LC-MS (Method 10-90): Rt 2.39 min; m/z 931.6 [M$^+$].

Example 47

Preparation of Biphenyl-2-ylcarbamic Acid 1-(2-{[4-(4-{[(R)-2-Hydroxy-2-(8-hydroxy-2-oxo-1,2-dihydroquinolin-5-yl)ethylamino]methyl}-2,5-dimethylphenylcarbamoyl)butyl]methylcarbamoyl}ethyl) piperidin-4-yl Ester Ditrifluoroacetic Acid Salt (Compound I-18)

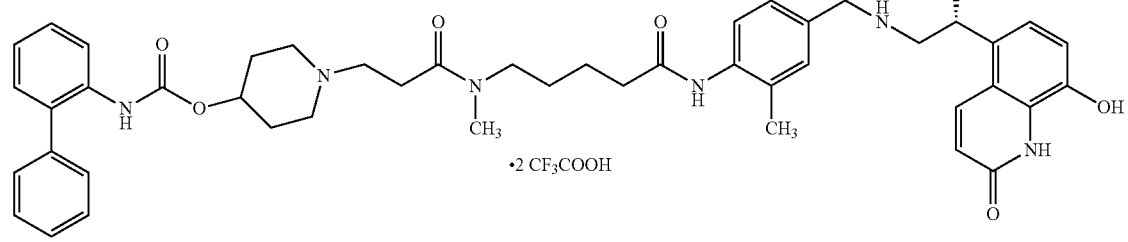

A solution of biphenyl-2-ylcarbamic acid 1-(2-{[4-(4-{[(R)-2-(tert-butyl-dimethylsilanyloxy)-2-(8-hydroxy-2-oxo-1,2-dihydroquinolin-5-yl)ethylamino]methyl}-2,5-dimethylphenylcarbamoyl)butyl]methylcarbamoyl}ethyl)piperidin-4-yl ester (0.420 g, 0.451 mmol) and triethylamine trihydrofluoride (0.220 mL, 1.35 mmol) in DCM (2.00 mL) was microwaved (300 watts) at 80° C. for 10 min. The reaction mixture was concentrated under reduced pressure and the residue was mixed with 1:1 AcOH:water and filtered. The filtrate was purified by HPLC (Method 2-90) to give the title compound (124 mg, 26% yield) as a white solid.

LC-MS (Method 10-90): Rt 1.75 min; m/z 817.8 [M+H]$^+$.
$^1$H NMR (CD$_3$OD) δ 8.30 (m), 7.56 (m), 7.40 (m), 7.06 (m), 6.68 (d), 5.46 (m), 4.35 (s), 3.51 (m), 3.30 (m), 3.16 (m), 2.94 (m), 2.42 (m), 2.27 (m), 1.97 (m), 1.72 (m).

Example 48

Preparation of Methyl 3-Methylaminobenzoate

A solution of formic acid (106 mL) and acetic anhydride (53.0 mL) was stirred at room temperature for 1 h. Methyl 3-aminobenzoate (8.50 g, 56.2 mmol) was added and the resulting mixture was stirred overnight. The reaction mixture was then concentrated under reduced pressure to give a solid. The solid was dissolved in THF (50.0 mL) and this solution was cooled to 0° C. Borane dimethylsulfide (10.7 mL, 112 mmol) was added slowly and the resulting mixture was stirred at room temperature overnight. The reaction mixture was then cooled to 0° C. and MeOH (10 mL) was added slowly. This mixture was stirred for 3 hours and then concentrated under reduced pressure to give the title compound, which was used without any further purification.

LC-MS (Method 10-90): Rt 1.25 min; m/z 166.4 [M+H]$^+$.

Example 49

Preparation of 3-(Acryloylmethylamino)benzoic Acid Methyl Ester

To a stirred mixture of 3-methylaminobenzoic acid methyl ester (3.11 g, 18.8 mmol) and sodium bicarbonate (3.16 g, 37.6 mmol) in DCM (20.0 mL) at 0° C. was added 2-propenoyl chloride (2.29 mL, 28.2 mmol). The reaction mixture was stirred overnight at room temperature. Saturated aqueous sodium bicarbonate solution was added and the layers were separated. The organic layer was dried over sodium sulfate, filtered and concentrated under reduced pressure to give the title compound (4.12 g, 100% yield), which was used in the next reaction without further purification.

Example 50

Preparation of 3-({3-[4-(Biphenyl-2-ylcarbamoyloxy)piperidin-1-yl]propionyl}methylamino)benzoic Acid Methyl Ester A stirred solution of 3-(acryloylmethylamino)benzoic acid methyl ester (estimated ~56 mmol) and biphenyl-2-ylcarbamic acid piperidin-4-yl ester (16.6 g, 56.0 mmol) in EtOH (20.0 mL) was heated at 90° C. overnight. The reaction mixture was concentrated under reduced pressure and the resulting residue was purified by silica gel flash chromatography (0-10% MeOH in DCM) to give the title compound (13.0 g, 45% yield) as an off-white solid.

LC-MS (Method 10-90): Rt 2.30 min; m/z 516.2 [M+H]$^+$.

Example 51

Preparation of 3-({3-[4-(Biphenyl-2-ylcarbamoyloxy)piperidin-1-yl]propionyl}methylamino)benzoic Acid A solution of 3-({3-[4-(biphenyl-2-ylcarbamoyloxy)piperidin-1-yl]-propionyl}methylamino)benzoic acid methyl ester (6.80 g, 13.2 mmol) and lithium hydroxide (1.58 g, 65.9 mmol) in a 1:1 mixture of acetonitrile:water (25.0 mL) was stirred at room temperature overnight. The pH of the reaction mixture was adjusted to pH 5 with aqueous hydrochloric acid (1M) and this mixture was extracted with DCM (20 mL). The organic layer was dried over sodium sulfate, filtered and concentrated under reduced pressure. The residue was purified by silica gel flash chromatography (0-10% MeOH in DCM) to give the title compound (5.80 g, 87% yield) as an off-white powder.

LC-MS (Method 10-90): Rt 2.15 min; m/z 502.2 [M+H]$^+$.

Example 52

Preparation of Biphenyl-2-ylcarbamic Acid 1-{2-[(3-Chlorocarbonylphenyl)methyl-carbamoyl]ethyl}piperidin-4-yl Ester A mixture of 3-({3-[4-(biphenyl-2-ylcarbamoyloxy)piperidin-1-yl]propionyl}-methylamino)benzoic acid (1.00 g, 2.00 mmol) and thionyl chloride (1.50 mL, 20.6 mmol) was stirred at room temperature for 1 h. The reaction mixture was then concentrated under reduced pressure to give the title compound, which was used immediately in the next reaction without further purification.

Example 53

Preparation of Biphenyl-2-ylcarbamic Acid 1-(2-{[3-(4-(1,3-Dioxolan-2-yl)-phenylcarbamoyl)phenyl]methylcarbamoyl}ethyl)piperidin-4-yl Ester To a stirred solution of 4-(1,3-dioxolan-2-yl)phenylamine (0.0826 g, 0.500 mmol) and N,N-diisopropylethylamine (348 µL, 2.00 mmol) in DCM (2.0 mL) at room temperature was added a solution of biphenyl-2-ylcarbamic acid 1-{2-[(3-chlorocarbonylphenyl)methylcarbamoyl]ethyl}piperidin-4-yl ester (0.260 g, 0.500 mmol) in DCM (1.0 mL). The resulting mixture was stirred at room temperature for 1 h. LC-MS (Method 10-90) showed product was present (Rt 3.41 min; m/z 649.4 [M+H]$^+$. Saturated aqueous sodium bicarbonate solution was added and the layers were separated. The organic layer was dried over sodium sulfate, filtered and concentrated under reduced pressure. The residue was purified by silica gel flash chromatography (0-5% MeOH in DCM) to give the title compound (345 mg containing some solvent residue, ca. 100% yield) as a brown oil.

Example 54

Preparation of Biphenyl-2-ylcarbamic Acid 1-(2-{[3-(4-Formylphenylcarbamoyl)-phenyl]methylcarbamoyl}ethyl)piperidin-4-yl Ester To a stirred solution of biphenyl-2-ylcarbamic acid 1-(2-{[3-(4-(1,3-dioxolan-2-yl)phenylcarbamoyl)phenyl]methylcarbamoyl}ethyl)piperidin-4-yl ester (345 mg containing some solvent residue, ca. 0.500 mmol) in acetonitrile (2.00 mL) at room temperature was added aqueous hydrochloric acid (1 N, 2.00 mL). The reaction mixture was stirred at room temperature for 3 h. LC-MS (Method 10-90) showed product was present (Rt 3.45 min; m/z 605.0 [M+H]$^+$. Saturated aqueous sodium bicarbonate solution was added and the layers were separated. The organic layer was dried over sodium sulfate, filtered and concentrated under reduced pressure to give the title compound, which was used in the next reaction without further purification.

Example 55

Preparation of Biphenyl-2-ylcarbamic Acid 1-(2-{[3-(4-{[(R)-2-(tert-Butyldimethylsilanyloxy)-2-(8-hydroxy-2-oxo-1,2-dihydroquinolin-5-yl)ethylamino]-methyl}phenylcarbamoyl)phenyl]methylcarbamoyl}ethyl)piperidin-4-yl Ester A solution of biphenyl-2-ylcarbamic acid 1-(2-{[3-(4-formylphenylcarbamoyl)-phenyl]methylcarbamoyl}ethyl)piperidin-4-yl ester (151 mg, 0.250 mmol) and 5-[(R)-2-amino-1-(tert-butyldimethylsilanyloxy)ethyl]-8-hydroxy-1H-quinolin-2-one acetic acid salt (98.6 mg, 0.250 mmol) in 1:1 MeOH:DCM (2.0 mL) was stirred at room temperature for 3 h. Sodium triacetoxyborohydride (159 mg, 0.750 mmol) was added and the reaction mixture was stirred at room temperature for 3 h. LC-MS (Method 10-90) showed product was present (Rt 3.32 min; m/z 923.6 [M+H]$^+$. Saturated aqueous sodium bicarbonate solution was added and the layers were separated. The organic layer was dried over sodium sulfate, filtered and concentrated under reduced pressure to give the title compound, which was used in the next reaction without further purification.

Example 56

Preparation of Biphenyl-2-ylcarbamic Acid 1-{2-[(4-{[(R)-2-Hydroxy-2-(8-hydroxy-2-oxo-1,2-dihydroquinolin-5-yl)ethylamino]methyl}-3-methoxyphenyl)-methylcarbamoyl]ethyl}piperidin-4-yl Ester Ditrifluoroacetic Acid (Compound I-25)

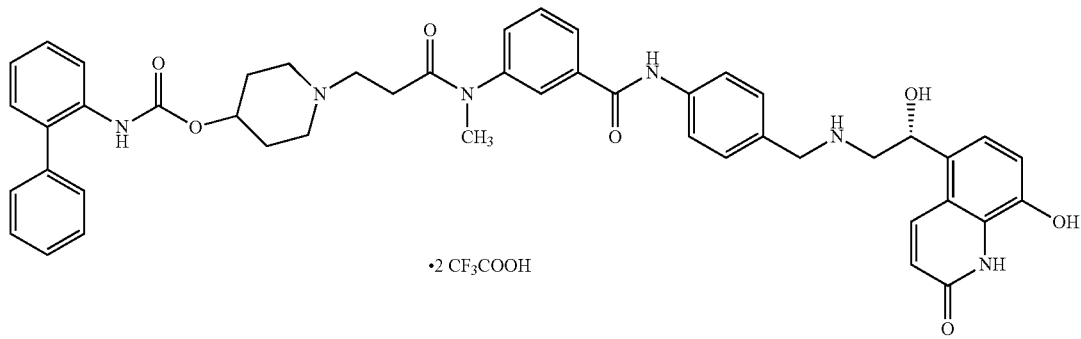 [SMILES: CN(C(=O)CCN1CCC(OC(=O)Nc2ccccc2-c2ccccc2)CC1)c1cccc(C(=O)Nc2ccc(CNC[C@H](O)c3ccc(O)c4[nH]c(=O)ccc34)cc2)c1]

A solution of biphenyl-2-ylcarbamic acid 1-{2-[(4-{[(R)-2-(tert-butyldimethyl-silanyloxy)-2-(8-hydroxy-2-oxo-1,2-dihydroquinolin-5-yl)ethylamino]methyl}-3-methoxyphenyl)methylcarbamoyl]ethyl}piperidin-4-yl ester (231 mg, 0.250 mmol) and triethylamine trihydrofluoride (204 µL, 1.25 mmol) in DCM (2.00 mL) was stirred at room temperature overnight. LC-MS (Method 10-90) showed product was present (Rt 2.73 min; m/z 809.6 [M+H]$^+$. The reaction mixture was concentrated under reduced pressure and the residue was purified by HPLC (Method 10-50) to give the title compound (47.3 mg, 23.4% yield, 99% purity) as a white solid.

Example 57

Preparation of 4-Nitrobenzenesulfonic Acid 2-(4-Nitrophenyl)ethyl Ester

To a stirred solution of 4-nitrobenzeneethanol (3.34 g, 20.0 mmol) and triethylenediamine (3.36 g, 30.0 mmol) in DCM (62.7 mL) at 0° C. was added 4-nitrobenzenesulfonyl chloride (4.97 g, 22.43 mmol) in portions over a 5 min period. The reaction mixture was then stirred at room temperature for 2 h. Water (50 mL) was added and the resulting mixture was stirred for 10 min. The organic layer was separated, dried over sodium sulfate, filtered and concentrated under reduced pressure to give the crude title compound (5.8 g, 82% yield) as a yellow solid.

HPLC (Method 2-90): Rt 4.23 min (214 nm).

Example 58

Preparation of 5-[(R)-2-{Benzyl-[2-(4-nitrophenyl)ethyl]amino}-1-(tert-butyldimethylsilanyloxy)ethyl]-8-benzyloxy-1H-quinolin-2-one A stirred solution of 4-nitrobenzenesulfonic acid 2-(4-nitrophenyl)ethyl ester (3.78 g, 10.7 mmol); 5-[(R)-2-benzylamino-1-(tert-butyldimethylsilanyloxy)ethyl]-8-benzyloxy-1H-quinolin-2-one (4.620 g, 8.975 mmol) and N,N-diisopropylethylamine (3.59 mL, 20.6 mmol) in acetonitrile (39.2 mL) was heated at 65° C. overnight. After cooling the reaction mixture to room temperature, EtOAc (20 mL) was added and this mixture was washed with brine (20 mL). The organic layer was dried over sodium sulfate, filtered and concentrated under reduced pressure. The residue was purified by silica gel chromatography (0-30% EtOAc in hexanes) to give the title compound (3.0 g, 50% yield) as a yellow oil.

LC-MS (Method 10-90): Rt 2.94 min; m/z 664.4 [M+H]$^+$.

Example 59

Preparation of 5-[(R)-2-{[2-(4-Aminophenyl)ethyl]benzylamino}-1-(tert-butyldimethylsilanyloxy)ethyl]-8-benzyloxy-1H-quinolin-2-one A mixture of 5-[(R)-2-{benzyl-[2-(4-nitrophenyl)ethyl]amino}-1-(tert-butyldimethylsilanyloxy)ethyl]-8-benzyloxy-1H-quinolin-2-one (3.00 g, 4.52 mmol); iron (2.52 g, 45.2 mmol) and iron(II) chloride tetrahydrate (0.18 g, 0.90 mmol) in EtOH (27.3 mL) and AcOH (9.09 mL) was stirred at 80° C. overnight. The reaction mixture was filtered through a pad of Celite, washing with EtOAc (20 mL). The organic layer was washed with brine (10 mL), dried over sodium sulfate, filtered and concentrated under reduced pressure to give the title compound, which was used without any further purification.

LC-MS (Method 10-90): Rt 2.43 min; m/z 634.4 [M+H]$^+$.

Example 60

Preparation of Biphenyl-2-ylcarbamic Acid 1-[2-({3-[4-(2-{Benzyl-[(R)-2-(8-benzyloxy-2-oxo-1,2-dihydroquinolin-5-yl)-2-(tert-butyldimethylsilanyloxy) ethyl]-amino}ethyl)phenylcarbamoyl] phenyl}methylcarbamoyl)ethyl]piperidin-4-yl Ester A mixture of 5-[(R)-2-{[2-(4-aminophenyl)ethyl]benzylamino}-1-(tert-butyldimethylsilanyloxy)ethyl]-8-benzyloxy-1H-quinolin-2-one (1.27 g, 2.00 mmol); 3-({3-[4-(biphenyl-2-ylcarbamoyloxy)piperidin-1-yl] propionyl}methylamino)benzoic acid (1.00 g, 2.00 mmol); 1-hydroxy-7-azabenzotriazole (0.286 g, 2.10 mmol) and N,N-diisopropylethylamine (0.697 mL, 4.00 mmol) in DCM (5.00 mL) was stirred for 30 min at room temperature. N-(3-Dimethylaminopropyl)-N-ethylcarbodiimide hydrochloride (0.575 g, 3.00 mmol) was added and the resulting mixture was stirred for 3 h. Saturated aqueous sodium bicarbonate solution (5 mL) was added and this mixture was extracted with DCM (2×5 mL). The combined organic layers were dried over sodium sulfate, filtered and concentrated under reduced pressure. The residue was purified by silica gel flash chromatography (0-10% MeOH in DCM) to give the title compound (1.74 g, 77% yield) as a yellow solid.

LC-MS (Method 10-90): Rt 2.73 min; m/z 1117.8 [M$^+$].

Example 61

Preparation of Biphenyl-2-ylcarbamic Acid 1-(2-{[3-(4-{2-[(R)-2-(tert-Butyldimethylsilanyloxy)-2-(8-hydroxy-2-oxo-1,2-dihydroquinolin-5-yl)ethylamino]-ethyl}phenylcarbamoyl)phenyl]methylcarbamoyl}ethyl)piperidin-4-yl Ester A solution of biphenyl-2-ylcarbamic acid 1-[2-({3-[4-(2-{benzyl-[(R)-2-(8-benzyloxy-2-oxo-1,2-dihydroquinolin-5-yl)-2-(tert-butyldimethylsilanyloxy)ethyl]-amino}ethyl) phenylcarbamoyl]phenyl}methylcarbamoyl)ethyl] piperidin-4-yl ester (1.74 g, 1.56 mmol) in EtOH (12.2 mL) and AcOH (0.122 mL) was flushed with nitrogen for 3 min. Palladium on carbon (10%, ~50% water, 0.18 g) was added and the reaction mixture was flushed with hydrogen for 4 min. The mixture was stirred under a hydrogen atmosphere (balloon) overnight and then filtered and concentrated under reduced pressure. The residue was purified by silica gel flash chromatography (0-15% MeOH in DCM) to give the title compound (1.11 g, 76% yield) as a thick brownish liquid.

LC-MS (Method 10-90): Rt 2.46 min; m/z 937.6 [M+H]$^+$.

Example 62

Preparation of Biphenyl-2-ylcarbamic Acid 1-(2-{[3-(4-{2-[(R)-2-Hydroxy-2-(8-hydroxy-2-oxo-1,2-dihydroquinolin-5-yl)ethylamino] ethyl}phenylcarbamoyl)-phenyl] methylcarbamoyl}ethyl)piperidin-4-yl Ester Ditrifluoroacetate (Compound I-34)

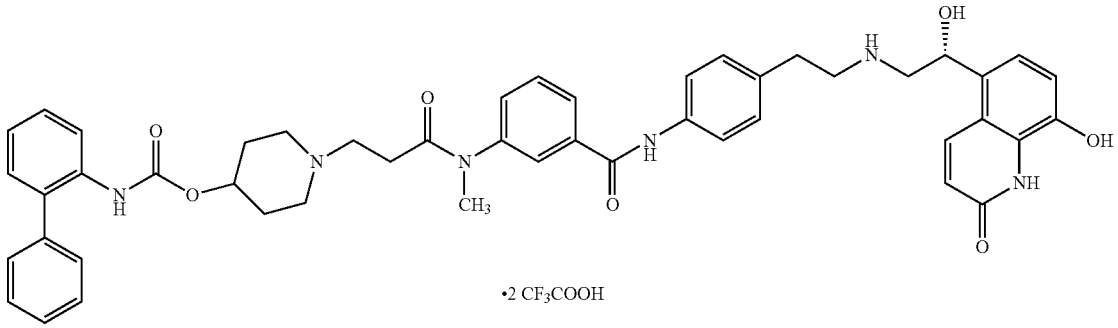 [SMILES: CN(C(=O)CCN1CCC(OC(=O)Nc2ccccc2-c2ccccc2)CC1)c1cccc(C(=O)Nc2ccc(CCNC[C@H](O)c3ccc(O)c4[nH]c(=O)ccc34)cc2)c1]

•2 CF$_3$COOH

A solution of biphenyl-2-ylcarbamic acid 1-(2-{[3-(4-{2-[(R)-2-(tert-butyldimethylsilanyloxy)-2-(8-hydroxy-2-oxo-1,2-dihydroquinolin-5-yl)ethylamino]-ethyl}phenylcarbamoyl)phenyl]methylcarbamoyl}ethyl) piperidin-4-yl ester (estimated ~1.56 mmol) and triethylamine trihydrofluoride (299 µL, 1.84 mmol) in DCM (3.06 mL) was microwaved (300 watts) at 80° C. for 10 min. The reaction mixture was concentrated under reduced pressure and the residue was purified by HPLC (Method 10-50) to give the title compound (280 mg, 17%) as a white solid.

LC-MS (Method 10-90): Rt 1.98 min; m/z 823.4 [M+H]$^+$.

Example 63

Preparation of [3-(2-Oxopropyl)phenyl]acetonitrile

A stirred solution of 3-bromophenylacetonitrile (10.0 g, 51.0 mmol), tributyltin methoxide (17.6 mL, 61.2 mmol), tris(dibenzylideneacetone)dipalladium(0) (500 mg, 0.5 mmol), isopropenyl acetate (6.74 mL, 61.2 mmol) and 2-dicyclohexylphosphino-2'-(N,N-dimethylamino)biphenyl (800 mg, 2 mmol) in toluene (100 mL, degassed) was heated at 100° C. under nitrogen for 6 h. The reaction mixture was cooled to room temperature and EtOAc (30 mL) was added. A solution of potassium fluoride (10 g, 200 mmol) in water (52 mL) was then added and the resulting mixture was stirred overnight. Brine was added and the mixture was filtered through a pad of Celite. The layers were separated and the organic layer was dried over sodium sulfate, filtered (cotton plug) and concentrated under reduced pressure. The residue was purified by silica gel chromatography (0-30% EtOAc in hexanes) to give the title compound (6.1 g, 69% yield) as a brown oil.

$^1$H NMR (CD$_3$OD) δ 7.32 (t, 1H); 7.24 (d, 1H); 7.19 (s, 1H); 7.16 (d, 1H); 3.85 (s, 2H); 3.77 (s, 2H); 2.14 (s, 3H).

Example 64

Preparation of {3-[(R)-2-((R)-1-Phenylethylamino)propyl]phenyl}acetonitrile Hydrochloride Salt To a stirred solution of [3-(2-oxopropyl)phenyl]acetonitrile (2.00 g, 11.5 mmol) and (R)-1-phenylethylamine (1.52 mL, 11.9 mmol) in DCM (50.0 mL) was added sodium triacetoxyborohydride (7.59 g, 35.8 mmol). The resulting mixture was stirred at room temperature overnight. Aqueous sodium hydroxide (1 M, 10 mL) and saturated aqueous sodium bicarbonate (20 mL) were added and the layers were separated. The organic layer was dried over sodium sulfate, filtered and concentrated under reduced pressure. The residue was partially purified by silica gel chromatography (0-5% MeOH in DCM). The resulting material was dissolved in MeOH and acetyl chloride (0.5 mL) was added. This mixture was concentrated under reduced pressure and the residue was dissolved in MeOH (15 mL). Diisopropyl ether (30 mL) was added slowly to form a second layer on top of the solution. After standing at room temperature, the titled compound (2.0 g, 55% yield) precipitated and was collected by filtration.

$^1$H NMR (CD$_3$OD) δ 7.53-7.51 (m, 5H); 7.32 (t, 1H); 7.24 (t, 1H); 7.10 (s, 1H); 7.05 (d, 1H); 4.64-4.59 (m, 1H); 3.21-3.16 (m, 2H); 1.70 (d, 3H); 1.17 (d, 3H).

Example 65

Preparation of {(R)-2-[3-(2-Aminoethyl)phenyl]-1-methylethyl}-((R)-1-phenylethyl)amine To a stirred solution of {3-[(R)-2-((R)-1-phenylethylamino)propyl]phenyl}-acetonitrile hydrochloride salt (2.00 g, 6.35 mmol) and cobalt(II) chloride hexahydrate (4.27 g, 18.0 mmol) in MeOH (40.0 mL) at 0° C. was added sodium tetrahydroborate (2.72 g, 71.8 mmol) portion-wise (reaction was exothermic). The reaction mixture was stirred for 1 h at room temperature and then concentrated aqueous hydrochloric acid was added and stirring was continued until the solid that had formed was broken-up. The mixture was then made basic by addition of aqueous sodium hydroxide (1 M). This mixture was filtered and the filtrate was extracted with DCM (50 mL). The organic layer was dried over sodium sulfate, filtered and concentrated under reduced pressure to give the title compound, which as used in the next reaction without further purification.

LC-MS (Method 10-90): Rt 0.938 min; m/z 283.6 [M+H]$^+$.

Alternatively, this reduction can be preformed using lithium aluminum hydride and cobalt(II) chloride hexahydrate in THF.

Example 66

Preparation of (2-{3-[(R)-2-((R)-1-Phenylethylamino)propyl]phenyl}ethyl)carbamic Acid tert-Butyl Ester A solution of {(R)-2-[3-(2-aminoethyl)phenyl]-1-methylethyl}-((R)-1-phenylethyl)amine (ca. 6.35 mmol), di-tert-butyldicarbonate (1.41 g, 6.46 mmol) and N,N-diisopropylethylamine (1.50 mL, 8.62 mmol) in DCM (20.0 mL) was stirred at room temperature for about 72 h. Saturated aqueous sodium bicarbonate (20 mL) was added and the resulting mixture was extracted with DCM (2×10 mL). The combined organic layers were dried over sodium sulfate, filtered and concentrated under reduced pressure. The residue was purified by silica gel chromatography (0-5% MeOH in DCM) to give the title compound (1.24 g, 51% yield, 2 steps) as a colorless oil.

LC-MS (Method 10-90): Rt 2.42 min; m/z 383.2 [M+H]$^+$.

Example 67

Preparation of {2-[3-((R)-2-Aminopropyl)phenyl]ethyl}carbamic Acid tert-Butyl Ester A stirred solution of (2-{3-[(R)-2-((R)-1-phenylethylamino)propyl]phenyl}ethyl)-carbamic acid tert-butyl ester (1.54 g, 4.02 mmol), palladium hydroxide on carbon (10 wt. %, ~50% water, 2.24 g, 0.805 mmol), and ammonium formate (1.27 g, 20.1 mmol) in EtOH (50.0 mL) was heated gradually to 50° C. and then stirred at 50° C. for 1.5 h. The reaction mixture was filtered through a pad of Celite and the filtrate was concentrated under reduced pressure to give the title compound, which was used without further purification.

LC-MS (Method 10-90): Rt 1.91 min; m/z 279.4 [M+H]$^+$.

Example 68

Preparation of [2-(3-{(R)-2-[(R)-2-(8-Benzyloxy-2-oxo-1,2-dihydroquinolin-5-yl)-2-(tert-butyldimethylsilanyloxy)ethylamino]propyl}phenyl)ethyl]carbamic Acid tert-Butyl Ester A stirred solution of 8-benzyloxy-5-[(R)-2-bromo-1-(tert-butyldimethyl-silanyloxy)ethyl]-1H-quinolin-2-one (3.14 g, 6.43 mmol); {2-[3-((R)-2-aminopropyl)-phenyl]ethyl}carbamic acid tert-butyl ester (1.79 g, 6.43 mmol) and triethylamine (1.08 mL, 7.72 mmol) in DMF (21.0 mL) was microwaved (300 watts) at 80° C. for 15 h. Saturated aqueous sodium bicarbonate (10 mL) was added and the resulting mixture was extracted with DCM (2×10 mL). The combined organic layers were dried over sodium sulfate, filtered and concentrated under reduced pressure. The residue was purified by silica gel chromatography (0-5% MeOH in DCM) to give the title compound (2.8 g, 63% yield) as an off-white solid.

LC-MS (Method 10-90): Rt 2.97 min; m/z 686.4 [M+H]$^+$.

Example 69

Preparation of 5-[(R)-2-{(R)-2-[3-(2-Aminoethyl)phenyl]-1-methylethylamino}-1-(tert-butyldimethylsilanyloxy)ethyl]-8-benzyloxy-1H-quinolin-2-one A solution of [2-(3-{(R)-2-[(R)-2-(8-benzyloxy-2-oxo-1,2-dihydroquinolin-5-yl)-2-(tert-butyldimethylsilanyloxy)ethylamino]propyl}phenyl)ethyl]carbamic acid tert-butyl ester (2.8 g) in 20% trifluoroacetic acid in DCM was stirred at room temperature for 3 h. Saturated aqueous sodium bicarbonate solution was added to neutralize the TFA and the layers were separated. The organic layer was dried over sodium sulfate, filtered and concentrated under reduced pressure to give the title compound, which was used without further purification.

LC-MS (Method 10-90): Rt 1.91 min; m/z 586.4 [M+H]$^+$.

Example 70

Preparation of Methyl (4-Formylaminophenyl)acetate

A solution of acetic anhydride (14.3 mL, 151 mmol) and formic acid (22.8 mL, 605 mmol) was stirred at room temperature for 1 h. Methyl (4-aminophenyl)acetate (5.00 g, 30.3 mmol) was added and the resulting mixture was stirred overnight. Saturated aqueous sodium bicarbonate (10 mL) was added and the resulting mixture was extracted with DCM (2×10 mL). The combined organic layers were dried over sodium sulfate, filtered and concentrated under reduced pressure to give the title compound (4.31 g) as a yellow oil, which was used in the next reaction without further purification.

LC-MS (Method 10-90): Rt 1.57 min; m/z 194.4 $[M+H]^+$.

Example 71

Preparation of Methyl (4-Methylaminophenyl)acetate

To a stirred solution of methyl (4-formylaminophenyl)acetate (4.31 g) in THF (20.0 mL) at 0° C. was slowly added borane dimethylsulfide (8.61 mL, 90.8 mmol). The reaction mixture was stirred at room temperature overnight and then cooled to 0° C. MeOH (15 mL) was added cautiously and the resulting mixture was stirred for 3 h. The mixture was then concentrated under reduced pressure to give the title compound (4.0 g, 73% yield, 2 steps) as a clear oil.

LC-MS (Method 10-90): Rt 0.67 min; m/z 180.2 $[M+H]^+$.

Example 72

Preparation of [4-(Acryloylmethylamino)phenyl]acetic Acid Methyl Ester

To a solution of methyl (4-methylaminophenyl)acetate (4.00 g, 22.3 mmol) and N,N-diisopropylethylamine (7.78 mL, 44.6 mmol) in DCM (20.0 mL) at 0° C. was slowly added 2-propenoyl chloride (2.18 mL, 26.8 mmol). The reaction mixture was stirred at room temperature for 2 h and then saturated aqueous sodium bicarbonate (20.0 mL) was added. This mixture was extracted with DCM (10 mL) and the organic layer was dried over sodium sulfate, filtered and concentrated under reduced pressure to give the title compound, which was used in the next reaction without further purification.

LC-MS (Method 10-90): Rt 2.20 min; m/z 234.0 $[M+H]^+$.

Example 73

Preparation of [4-({3-[4-(Biphenyl-2-ylcarbamoyloxy)piperidin-1-yl]propionyl}-methylamino)phenyl] acetic Acid Methyl Ester A stirred solution of [4-(acryloylmethylamino)phenyl] acetic acid methyl ester (~22.3 mmol) and biphenyl-2-ylcarbamic acid piperidin-4-yl ester (6.61 g, 22.3 mmol) in EtOH (15.0 mL) was heated at reflux overnight. The reaction mixture was concentrated under reduced pressure and the residue was purified by silica gel chromatography (0-5% MeOH in DCM) to give the title compound (8.41 g, 71% yield, 2 steps) as a brown sticky solid.

LC-MS (Method 10-90): Rt 2.36 min; m/z 530.6 $[M+H]^+$.

Example 74

Preparation of [4-({3-[4-(Biphenyl-2-ylcarbamoyloxy)piperidin-1-yl]propionyl}-methylamino)phenyl] acetic Acid A stirred solution of [4-({3-[4-(biphenyl-2-ylcarbamoyloxy)piperidin-1-yl]-propionyl}methylamino)phenyl]acetic acid methyl ester (8.00 g, 15.1 mmol) and lithium hydroxide (1.81 g, 75.5 mmol) in acetonitrile (20.0 mL) and water (20.0 mL) was heated at 60° C. for 3 h. The pH of the reaction mixture was adjusted to pH 5 with aqueous hydrochloric acid (1 M) and the mixture was extracted with DCM. The organic layer was dried over sodium sulfate, filtered and concentrated under reduced pressure. The residue was purified by silica gel chromatography (0-20% MeOH in DCM) to give the title compound (6.7 g, 86% yield) as an off-white solid.

LC-MS (Method 10-90): Rt 2.17 min; m/z 516.4 $[M+H]^+$.

Example 75

Preparation of Biphenyl-2-ylcarbamic Acid 1-{2-[(4-{[2-(3-{(R)-2-[(R)-2-(8-Benzyloxy-2-oxo-1,2-dihydroquinolin-5-yl)-2-(tert-butyldimethylsilanyloxy)-ethylamino]propyl}phenyl)ethylcarbamoyl] methyl}phenyl)-methylcarbamoyl]ethyl}piperidin-4-yl Ester A mixture of 5-[(R)-2-{(R)-2-[3-(2-aminoethyl)phenyl]-1-methylethylamino}-1-(tert-butyldimethylsilanyloxy) ethyl]-8-benzyloxy-1H-quinolin-2-one (0.586 g, 1.00 mmol); [4-({3-[4-(biphenyl-2-ylcarbamoyloxy)piperidin-1-yl]propionyl}methylamino)-phenyl]acetic acid (0.516 g, 1.00 mmol); 2-chloropyridium triflate on Wang resin (polymer-supported Mukaiyama reagent) (1.19 mmol/g loading; 1.68 g, 2.00 mmol); and N,N-diisopropylethylamine (522 µL, 3.00 mmol) in DCM (5.00 mL) was stirred at room temperature overnight. The reaction mixture was filtered and the filtrate was concentrated under reduced pressure. The residue was purified by silica gel chromatography (0-5% MeOH in DCM) to give the title compound (412 mg, 38% yield) as an off-white oil.

LC-MS (Method 10-90): Rt 2.65 min; m/z 1083.8 $[M+H]^+$.

Example 76

Preparation of Biphenyl-2-ylcarbamic Acid 1-{2-[(4-{[2-(3-{(R)-2-[(R)-2-(tert-Butyl-dimethylsilanyloxy)-2-(8-hydroxy-2-oxo-1,2-dihydroquinolin-5-yl) ethylamino]-propyl}phenyl)ethylcarbamoyl] methyl}-phenyl)methylcarbamoyl]ethyl}piperidin-4-yl Ester Dry nitrogen was bubbled into a stirred solution of biphenyl-2-ylcarbamic acid 1-{2-[(4-{[2-(3-{(R)-2-[(R)-2-(8-benzyloxy-2-oxo-1,2-dihydroquinolin-5-yl)-2-(tert-butyldimethylsilanyloxy)-ethylamino]propyl}phenyl) ethylcarbamoyl]-methyl}phenyl)methylcarbamoyl]ethyl}-piperidin-4-yl ester (0.704 g, 0.650 mmol) in EtOH (5.00 mL) for 3 min and then palladium on carbon (10 wt. %, ~50% water; 0.289 g, 0.130 mmol) was added. Hydrogen was bubbled into the reaction mixture for 3 min and then the mixture was stirred under an atmosphere of hydrogen (balloon) for 1 h. The reaction mixture was filtered and the filtrate was concentrated under reduced pressure to give the title compound, which was used without further purification in the next reaction.

LC-MS (Method 10-90): Rt 2.49 min; m/z 994.0 $[M+H]^+$.

Example 77

Preparation of Biphenyl-2-ylcarbamic Acid 1-{2-[(4-{[2-(3-{(R)-2-[(R)-2-Hydroxy-2-(8-hydroxy-2-oxo-1,2-dihydroquinolin-5-yl)ethylamino]propyl}phenyl)-ethylcarbamoyl]methyl}phenyl)methylcarbamoyl]ethyl}piperidin-4-yl Ester Ditrifluoroacetic Acid Salt (Compound I-86)

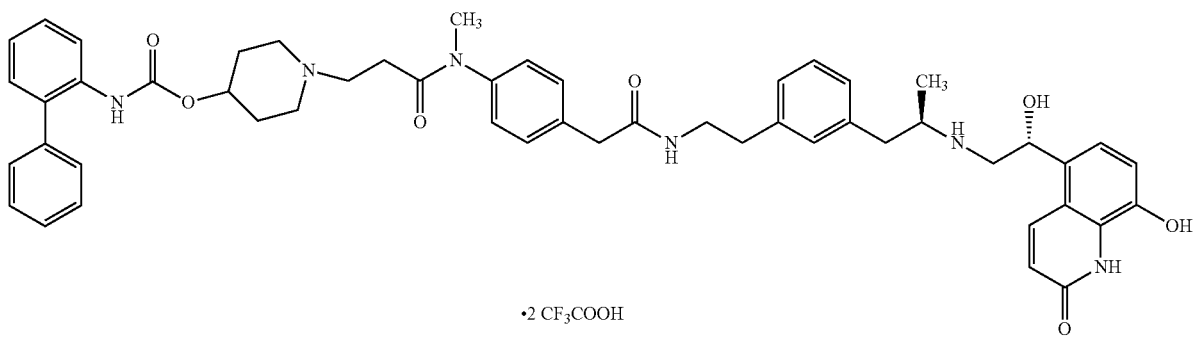 [SMILES: C[C@H](Cc1cccc(CCNC(=O)Cc2ccc(N(C)C(=O)CCN3CCC(OC(=O)Nc4ccccc4-c4ccccc4)CC3)cc2)c1)NC[C@H](O)c1ccc(O)c2[nH]c(=O)ccc12]

•2 CF₃COOH

A solution of biphenyl-2-ylcarbamic acid 1-{2-[(4-{[2-(3-{(R)-2-[(R)-2-(tert-butyldimethylsilanyloxy)-2-(8-hydroxy-2-oxo-1,2-dihydroquinolin-5-yl)ethylamino]-propyl}phenyl)ethylcarbamoyl]methyl}phenyl)methylcarbamoyl]ethyl}piperidin-4-yl ester (~0.65 mmol) and triethylamine trihydrofluoride (184 μL, 1.13 mmol) in DCM (3.00 mL) was microwaved (300 watts) at 80° C. for 10 min. The reaction mixture was concentrated under reduced pressure and the residue was purified by HPLC (Method 10-50) to give the title compound (24.7 mg, 4% yield, 2 steps) as a white solid.

LC-MS (Method 10-90): Rt 1.78 min; m/z 879.8 [M+H]⁺.

By modifying the starting materials employed in the previous examples or by using similar procedures, the compounds shown in Table II were prepared:

TABLE II

| Ex. No. | ID No. | Compound | Amount/LC-MS[1] |
|---|---|---|---|
| 78 | I-2 |  | 39 mg<br>Rt 2.94 min;<br>m/z 789.6 |

Biphenyl-2-ylcarbamic acid 1-(2-{[3-(4-{[(R)-2-hydroxy-2-(8-hydroxy-2-oxo-1,2-dihydroquinolin-5-yl)ethylamino]methyl}-2-methylphenylcarbamoyl)-propyl]methylcarbamoyl}ethyl)piperidin-4-yl ester ditrifluoroacetic acid salt TABLE II-continued

| Ex. No. | ID No. | Compound | Amount/ LC-MS[1] |
|---|---|---|---|
| 79 | I-3 | 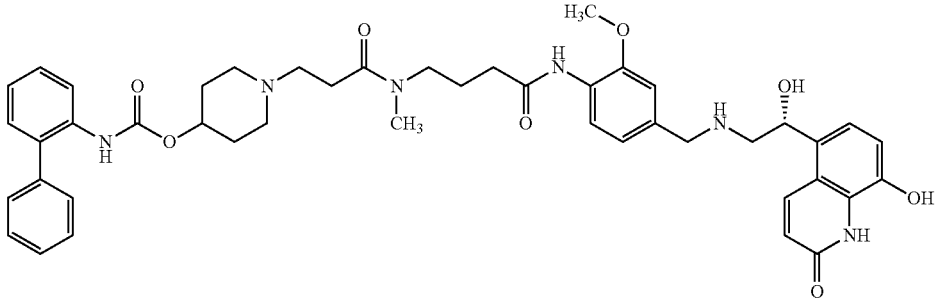<br>•2 CF$_3$COOH<br>Biphenyl-2-ylcarbamic acid 1-(2-{[3-(4-{[(R)-2-hydroxy-2-(8-hydroxy-2-oxo-1,2-dihydroquinolin-5-yl)ethylamino]methyl}-2-methoxyphenylcarbamoyl)-propyl]methylcarbamoyl}ethyl)piperidin-4-yl ester ditrifluoroacetic acid salt | 14 mg<br>Rt 2.90 min;<br>m/z 805.8 |
| 80 | I-4 | 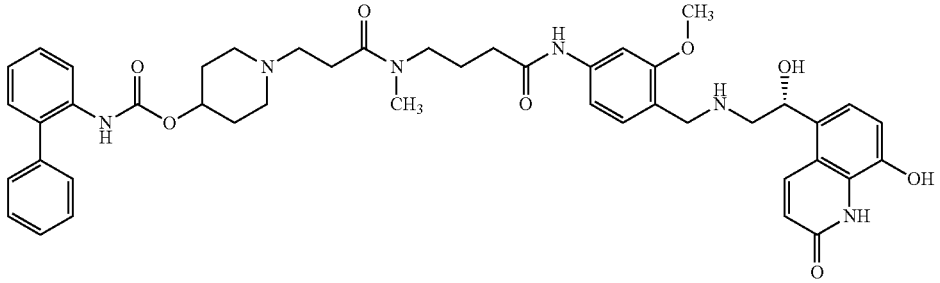<br>•2 CF$_3$COOH<br>Biphenyl-2-ylcarbamic acid 1-(2-{[3-(4-{[(R)-2-hydroxy-2-(8-hydroxy-2-oxo-1,2-dihydroquinolin-5-yl)ethylamino]methyl}-3-methoxyphenylcarbamoyl)-propyl]methylcarbamoyl}ethyl)piperidin-4-yl ester ditrifluoroacetic acid salt | 9 mg<br>Rt 3.18 min;<br>m/z 805.6 |
| 81 | I-5 | 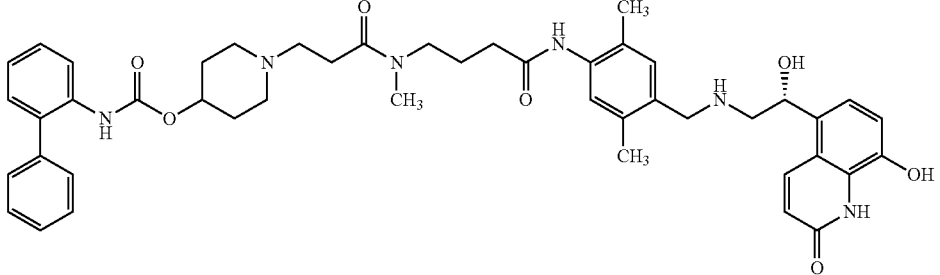<br>•2 CF$_3$COOH<br>Biphenyl-2-ylcarbamic acid 1-(2-{[3-(4-{[(R)-2-hydroxy-2-(8-hydroxy-2-oxo-1,2-dihydroquinolin-5-yl)ethylamino]methyl}-2,5-dimethylphenylcarbamoyl)-propyl]methylcarbamoyl}ethyl)piperidin-4-yl ester ditrifluoroacetic acid salt | 50 mg<br>Rt 2.20 min;<br>m/z 803.6 |

TABLE II-continued

| Ex. No. | ID No. | Compound | Amount/ LC-MS[1] |
|---|---|---|---|
| 82 | I-6 | Biphenyl-2-ylcarbamic acid 1-(2-{[3-(2-chloro-4-{[(R)-2-hydroxy-2-(8-hydroxy-2-oxo-1,2-dihydroquinolin-5-yl) ethylamino]ethyl}-5-methoxyphenylcarbamoyl)-propyl]methylcarbamoyl}ethyl)piperidin-4-yl ester ditrifluoroacetic acid salt • 2 CF$_3$COOH | 20 mg Rt 2.15 min; m/z 839.6 |
| 83 | I-8 | Biphenyl-2-ylcarbamic acid 1-(2-{[3-(4-{2-[(R)-2-hydroxy-2-(8-hydroxy-2-oxo-1,2-dihydroquinolin-5-yl)ethylamino] ethyl}-phenylcarbamoyl)propyl]methyl-carbamoyl}ethyl)piperidin-4-yl ester ditrifluoroacetic acid salt • 2 CF$_3$COOH | 144 mg Rt 2.77 min; m/z 789.6 |
| 84 | I-9 | Biphenyl-2-ylcarbamic acid 1-(2-{[3-(3-{2-[(R)-2-hydroxy-2-(8-hydroxy-2-oxo-1,2-dihydroquinolin-5-yl)ethylamino] ethyl}-4-methoxyphenylcarbamoyl)-propyl]methylcarbamoyl}ethyl)piperidin-4-yl ester ditrifluoroacetic acid salt • 2 CF$_3$COOH | 29 mg Rt 2.81 min; m/z 819.6 |

| Ex. No. | ID No. | Compound | Amount/ LC-MS[1] |
|---|---|---|---|
| 85 | I-10 | 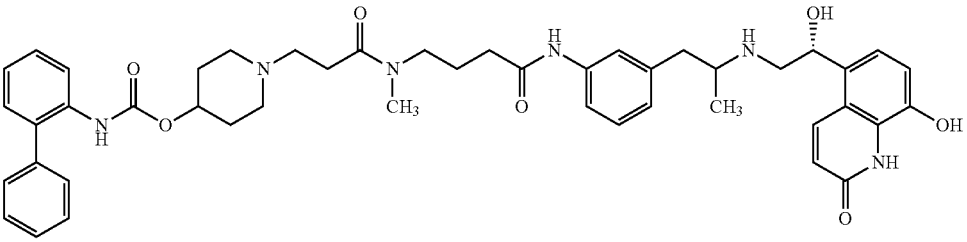<br><br>Biphenyl-2-ylcarbamic acid 1-(2-{[3-(3-{2-[(R)-2-hydroxy-2-(8-hydroxy-2-oxo-1,2-dihydroquinolin-5-yl)ethylamino]propyl}-phenylcarbamoyl)propyl]methyl-carbamoyl}ethyl)piperidin-4-yl ester ditrifluoroacetic acid salt | 38 mg<br>Rt 2.93 min;<br>m/z 803.6 |
| 86 | I-11 | 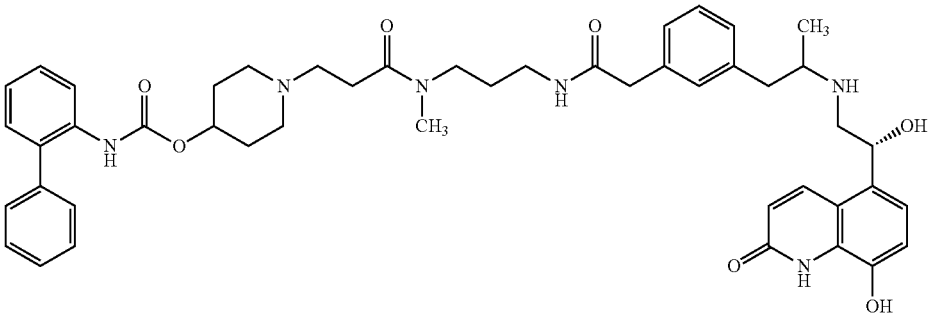<br><br>Biphenyl-2-ylcarbamic acid 1-[2-({3-[2-(3-{2-[(R)-2-hydroxy-2-(8-hydroxy-2-oxo-1,2-dihydroquinolin-5-yl)ethylamino]propyl}phenyl)acetylamino]propyl}-methylcarbamoyl)ethyl]piperidin-4-yl ester ditrifluoroacetic acid salt | 35 mg<br>Rt 2.95 min;<br>m/z 817.8 |
| 87 | I-12 | 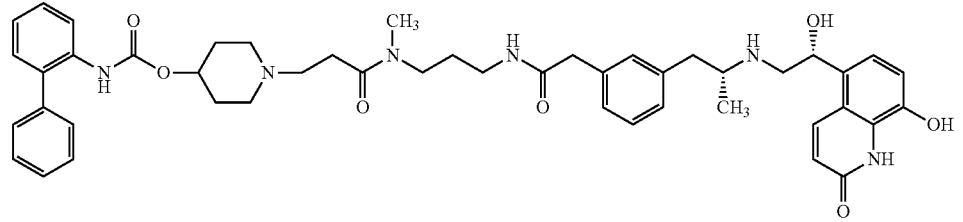<br><br>Biphenyl-2-ylcarbamic acid 1-[2-({3-[2-(3-{(R)-2-[(R)-2-hydroxy-2-(8-hydroxy-2-oxo-1,2-dihydroquinolin-5-yl)ethylamino]propyl}phenyl)acetylamino]propyl}-methylcarbamoyl)ethyl]piperidin-4-yl ester ditrifluoroacetic acid salt | 10 mg<br>Rt 2.23 min;<br>m/z 817.6 |
| 88 | I-15 | 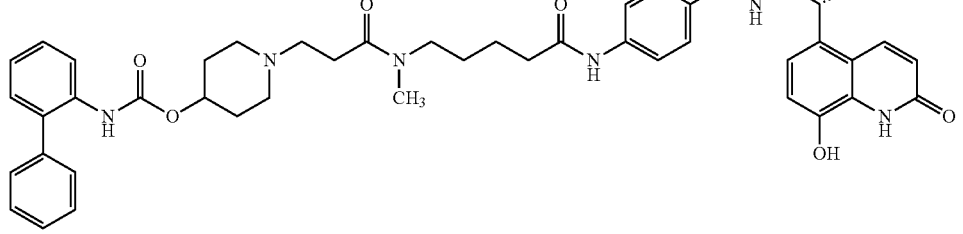<br><br>Biphenyl-2-ylcarbamic acid 1-(2-{[4-(4-{[(R)-2-hydroxy-2-(8-hydroxy-2-oxo-1,2-dihydroquinolin-5-yl)-ethylamino]methyl}-2-methylphenylcarbamoyl)butyl]-methylcarbamoyl}ethyl)piperidin-4-yl ester ditrifluoroacetic acid salt | 43 mg<br>Rt 2.81 min;<br>m/z 803.6 |

TABLE II-continued

| Ex. No. | ID No. | Compound | Amount/ LC-MS[1] |
|---|---|---|---|
| 89 | I-16 | 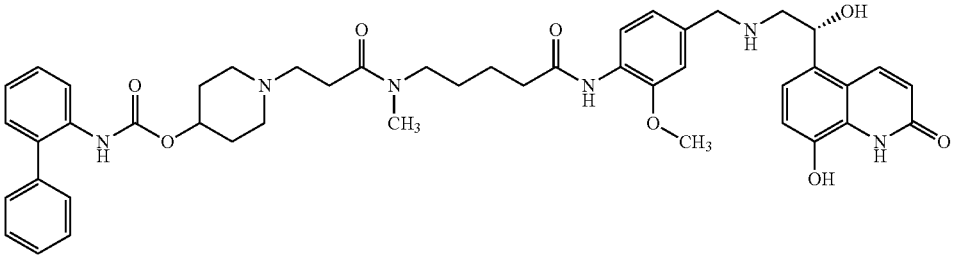 •2 CF$_3$COOH<br>Biphenyl-2-ylcarbamic acid 1-(2-{[4-(4-{[(R)-2-hydroxy-2-(8-hydroxy-2-oxo-1,2-dihydroquinolin-5-yl)-ethylamino]methyl}-2-methoxyphenylcarbamoyl)-butyl]methylcarbamoyl}ethyl)piperidin-4-yl ester ditrifluoroacetic acid salt | 10 mg<br>Rt 2.18 min;<br>m/z 819.8 |
| 90 | I-17 | 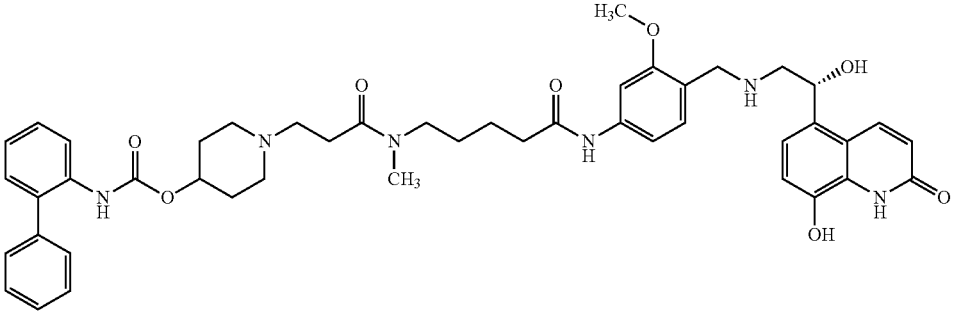 •2 CF$_3$COOH<br>Biphenyl-2-ylcarbamic acid 1-(2-{[4-(4-{[(R)-2-hydroxy-2-(8-hydroxy-2-oxo-1,2-dihydroquinolin-5-yl)-ethylamino]methyl}-3-methoxyphenylcarbamoyl)-butyl]methylcarbamoyl}ethyl)piperidin-4-yl ester ditrifluoroacetic acid salt | 85 mg<br>Rt 2.18 min;<br>m/z 819.8 |
| 91 | I-19 | 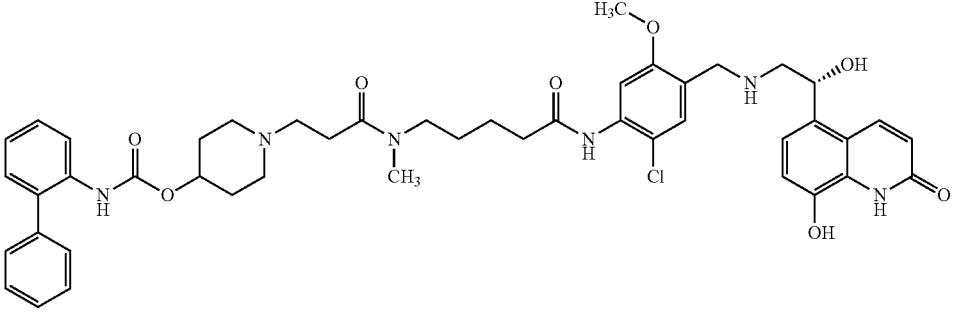 •2 CF$_3$COOH<br>Biphenyl-2-ylcarbamic acid 1-(2-{[4-(2-chloro-4-{[(R)-2-hydroxy-2-(8-hydroxy-2-oxo-1,2-dihydroquinolin-5-yl)ethylamino]methyl}-5-methoxyphenylcarbamoyl)-butyl]methylcarbamoyl}ethyl)piperidin-4-yl ester ditrifluoroacetic acid salt | 30 mg<br>Rt 3.52 min;<br>m/z 853.4 |

US 8,816,088 B2

TABLE II-continued

| Ex. No. | ID No. | Compound | Amount/ LC-MS[1] |
|---|---|---|---|

92  I-20  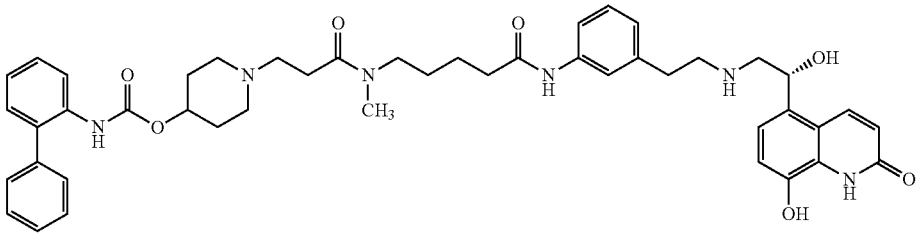  53 mg
Rt 2.84 min;
m/z 803.6

•2 CF$_3$COOH

Biphenyl-2-ylcarbamic acid 1-(2-{[4-(3-{2-[(R)-2-hydroxy-2-(8-hydroxy-2-oxo-1,2-dihydroquinolin-5-yl)-
ethylamino]ethyl}phenylcarbamoyl)butyl]methyl-carbamoyl}ethyl)piperidin-4-yl ester
ditrifluoroacetic acid salt 93  I-21  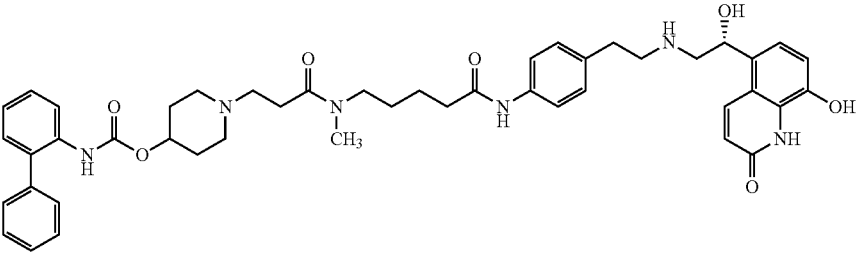  46 mg
Rt 2.82 min;
m/z 803.6

•2 CF$_3$COOH

Biphenyl-2-ylcarbamic acid 1-(2-{[4-(4-{2-[(R)-2-hydroxy-2-(8-hydroxy-2-oxo-1,2-dihydroquinolin-5-
yl)-ethylamino]ethyl}phenylcarbamoyl)butyl]methyl-carbamoyl}ethyl)piperidin-4-yl ester
ditrifluoroacetic acid salt 94  I-22  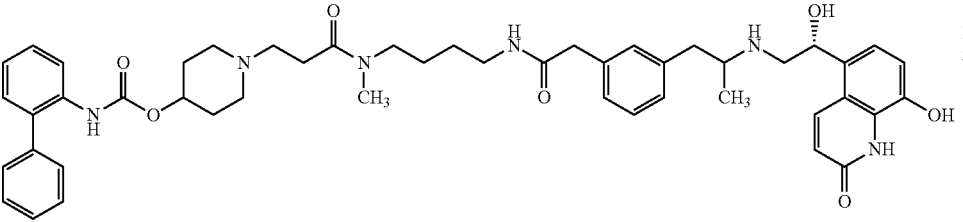  25 mg
Rt 2.95 min;
m/z 831.8

•2 CF$_3$COOH

Biphenyl-2-ylcarbamic acid 1-[2-({4-[2-(3-{2-[(R)-2-hydroxy-2-(8-hydroxy-2-oxo-1,2-dihydroquinolin-5-yl)
ethylamino]propyl}phenyl)acetylamino]butyl}-methylcarbamoyl)ethyl]piperidin-4-yl ester
ditrifluoroacetic acid salt TABLE II-continued

| Ex. No. | ID No. | Compound | Amount/ LC-MS[1] |
|---|---|---|---|
| 95 | I-23 | 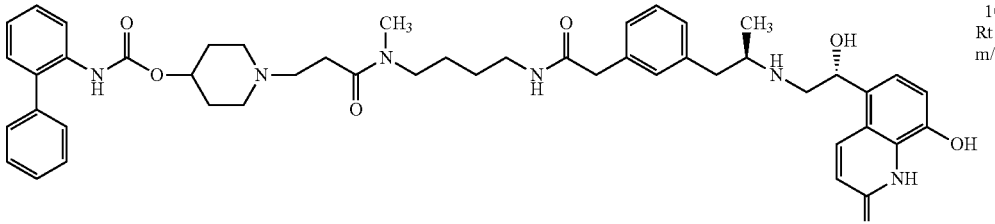 •2 CF₃COOH<br>Biphenyl-2-ylcarbamic acid 1-[2-({4-[2-(3-{(R)-2-[(R)-2-hydroxy-2-(8-hydroxy-2-oxo-1,2-dihydroquinolin-5-yl)ethylamino]propyl}phenyl)acetylamino]butyl}methyl-carbamoyl)ethyl]piperidin-4-yl ester ditrifluoroacetic acid salt | 10 mg Rt 2.26 min; m/z 831.6 |
| 96 | I-24 | 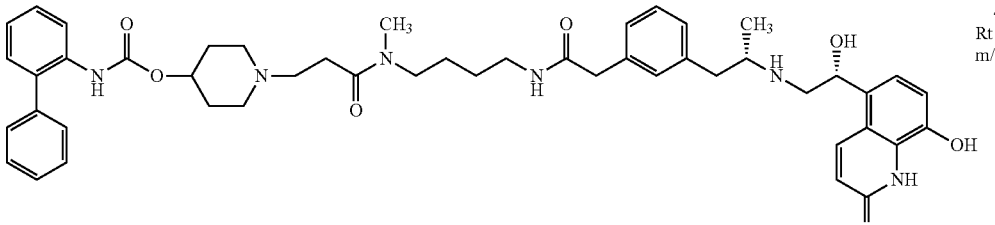 •2 CF₃COOH<br>Biphenyl-2-ylcarbamic acid 1-[2-({4-[2-(3-{(S)-2-[(R)-2-hydroxy-2-(8-hydroxy-2-oxo-1,2-dihydroquinolin-5-yl)-ethylamino]propyl}phenyl)acetylamino]butyl}methyl-carbamoyl)ethyl]piperidin-4-yl ester ditrifluoroacetic acid salt | 4 mg Rt 4.34 min; m/z 831.4 |
| 97 | I-26 | 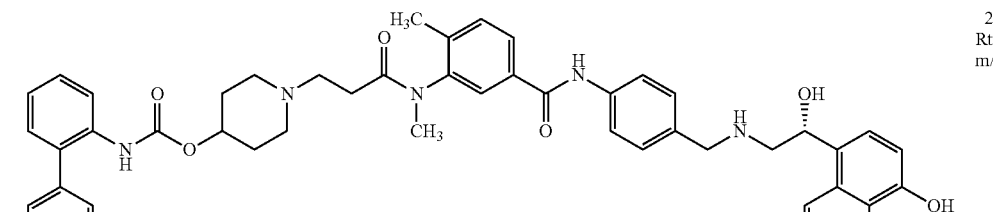 •2 CF₃COOH<br>Biphenyl-2-ylcarbamic acid 1-(2-{[5-(4-{[(R)-2-hydroxy-2-(8-hydroxy-2-oxo-1,2-dihydroquinolin-5-yl)-ethylamino]methyl}phenylcarbamoyl)-2-methylphenyl]-methylcarbamoyl}ethyl)piperidin-4-yl ester ditrifluoroacetic acid salt | 21 mg Rt 2.78 min; m/z na |
| 98 | I-27 |  •2 CF₃COOH<br>Biphenyl-2-ylcarbamic acid 1-(2-{[3-(4-{[(R)-2-hydroxy-2-(8-hydroxy-2-oxo-1,2-dihydroquinolin-5-yl)-ethylamino]methyl}-2-methylphenylcarbamoyl)phenyl]-methylcarbamoyl}ethyl)piperidin-4-yl ester ditrifluoroacetic acid salt | 92 mg Rt 2.66 min; m/z 823.6 |

| Ex. No. | ID No. | Compound | Amount/ LC-MS[1] |
|---|---|---|---|
| 99 | I-28 | 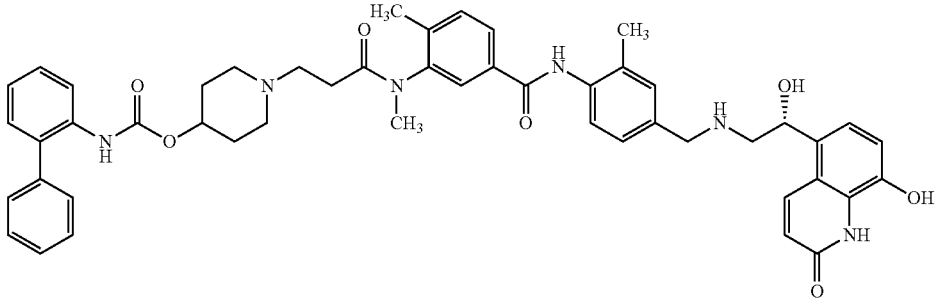<br>•2 CF₃COOH<br><br>Biphenyl-2-ylcarbamic acid 1-(2-{[5-(4-{[(R)-2-hydroxy-2-(8-hydroxy-2-oxo-1,2-dihydroquinolin-5-yl)-ethylamino]methyl}-2-methylphenylcarbamoyl)-2-methylphenyl]methylcarbamoyl}ethyl)piperidin-4-yl ester ditrifluoroacetic acid salt | 37 mg<br>Rt 3.07 min;<br>m/z 837.5 |
| 100 | I-29 | 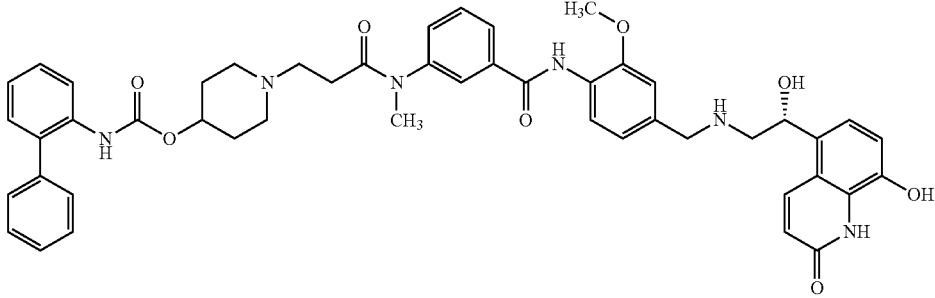<br>•2 CF₃COOH<br><br>Biphenyl-2-ylcarbamic acid 1-(2-{[3-(4-{[(R)-2-hydroxy-2-(8-hydroxy-2-oxo-1,2-dihydroquinolin-5-yl)-ethylamino]methyl}-2-methoxyphenylcarbamoyl)-phenyl]methylcarbamoyl}ethyl)piperidin-4-yl ester ditrifluoroacetic acid salt | 28 mg<br>Rt 2.76 min;<br>m/z 839.4 |
| 101 | I-30 | 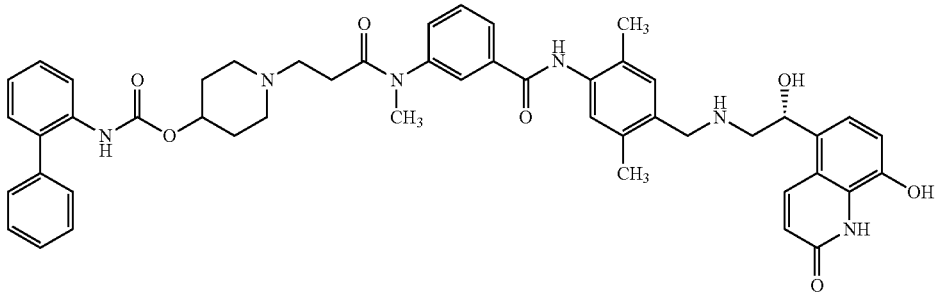<br>•2 CF₃COOH<br><br>Biphenyl-2-ylcarbamic acid 1-(2-{[3-(4-{[(R)-2-hydroxy-2-(8-hydroxy-2-oxo-1,2-dihydroquinolin-5-yl)-ethylamino]methyl}-2,5-dimethylphenylcarbamoyl)-phenyl]methylcarbamoyl}ethyl)piperidin-4-yl ester ditrifluoroacetic acid salt | 29 mg<br>Rt 3.51 min;<br>m/z 837.5 |

TABLE II-continued

| Ex.<br>No. | ID<br>No. | Compound | Amount/<br>LC-MS[1] |
|---|---|---|---|
| 102 | I-31 | | 45 mg<br>Rt 3.42 min;<br>m/z 873.6 |

•2 CF₃COOH

Biphenyl-2-ylcarbamic acid 1-(2-{[3-(2-chloro-4-{[(R)-2-hydroxy-2-(8-hydroxy-2-oxo-1,2-dihydroquinolin-5-yl)
ethylamino]methyl}-5-methoxyphenylcarbamoyl)-phenyl]methylcarbamoyl}ethyl)piperidin-4-yl ester
ditrifluoroacetic acid salt

| 103 | I-32 | | 31 mg<br>Rt 2.92 min;<br>m/z 823.5 |

•2 CF₃COOH

Biphenyl-2-ylcarbamic acid 1-(2-{[3-(3-{2-[(R)-2-hydroxy-2-(8-hydroxy-2-oxo-1,2-dihydroquinolin-5-yl)-ethylamino]
ethyl}phenylcarbamoyl)phenyl]methyl-carbamoyl}ethyl)piperidin-4-yl ester
ditrifluoroacetic acid salt

| 104 | I-33 | | 48 mg<br>Rt 3.21 min;<br>m/z 837.5 |

•2 CF₃COOH

Biphenyl-2-ylcarbamic acid 1-(2-{[5-(3-{2-[(R)-2-hydroxy-2-(8-hydroxy-2-oxo-1,2-dihydroquinolin-5-yl)-ethylamino]
ethyl}phenylcarbamoyl)-2-methylphenyl]-methylcarbamoyl}ethyl)piperidin-4-yl ester
ditrifluoroacetic acid salt

| 105 | I-34 | | 56 mg<br>Rt 3.15 min;<br>m/z 837.4 |

•2 CF₃COOH

Biphenyl-2-ylcarbamic acid 1-(2-{[5-(4-{2-[(R-2-hydroxy-2-(8-hydroxy-2-oxo-1,2-dihydroquinolin-5-yl)-ethylamino]
ethyl}phenylcarbamoyl)-2-methylphenyl]-methylcarbamoyl}ethyl)piperidin-4-yl ester
ditrifluoroacetic acid salt

TABLE II-continued

| Ex. No. | ID No. | Compound | Amount/LC-MS[1] |
|---|---|---|---|
| 106 | I-36 | 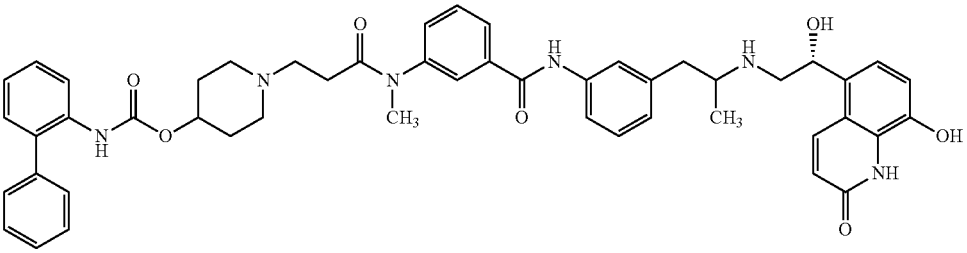 •2 CF$_3$COOH<br><br>Biphenyl-2-ylcarbamic acid 1-(2-{[3-(3-{2-[(R)-2-hydroxy-2-(8-hydroxy-2-oxo-1,2-dihydroquinolin-5-yl)-ethylamino]propyl}phenylcarbamoyl)phenyl]methyl-carbamoyl}ethyl)piperidin-4-yl ester ditrifluoroacetic acid salt | 20 mg<br>Rt 3.16 min;<br>m/z 837.4 |
| 107 | I-37 | 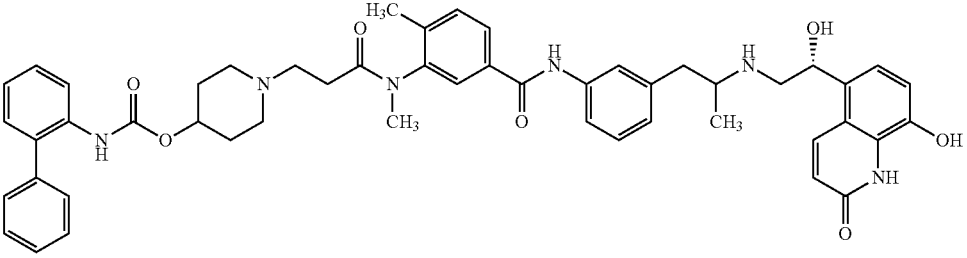 •2 CF$_3$COOH<br><br>Biphenyl-2-ylcarbamic acid 1-(2-{[5-(3-{2-[(R)-2-hydroxy-2-(8-hydroxy-2-oxo-1,2-dihydroquinolin-5-yl)-ethylamino]propyl}phenylcarbamoyl)-2-methylphenyl]-methylcarbamoyl}ethyl)piperidin-4-yl ester ditrifluoroacetic acid salt | 13 mg<br>Rt 3.10 min;<br>m/z 851.6 |
| 108 | I-38 | 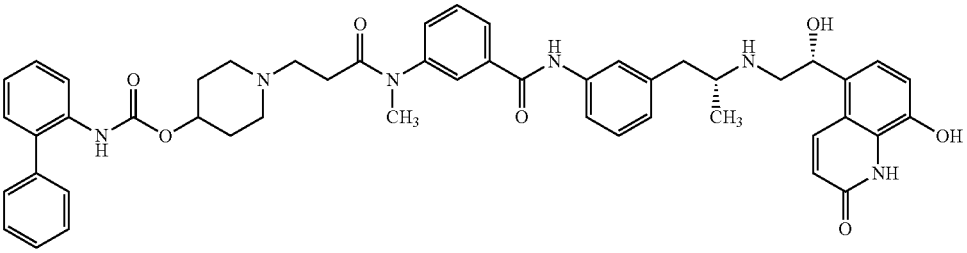 •2 CF$_3$COOH<br><br>Biphenyl-2-ylcarbamic acid 1-(2-{[3-(3-{(R)-2-[(R)-2-hydroxy-2-(8-hydroxy-2-oxo-1,2-dihydroquinolin-5-yl)-ethylamino]propyl}phenylcarbamoyl)phenyl]methyl-carbamoyl}ethyl)piperidin-4-yl ester ditrifluoroacetic acid salt | 5 mg<br>Rt 4.15 min;<br>m/z 837.5 |
| 109 | I-39 | 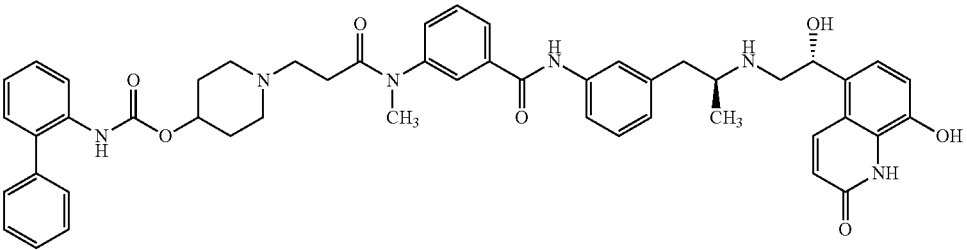 •2 CF$_3$COOH<br><br>Biphenyl-2-ylcarbamic acid 1-(2-{[3-(3-{(S)-2-[(R)-2-hydroxy-2-(8-hydroxy-2-oxo-1,2-dihydroquinolin-5-yl)-ethylamino]propyl}phenylcarbamoyl)phenyl]methyl-carbamoyl}ethyl)piperidin-4-yl ester ditrifluoroacetic acid salt | 28 mg<br>Rt 2.12 min;<br>m/z 837.8 |

TABLE II-continued

| Ex. ID No. | No. | Compound | Amount/ LC-MS[1] |
|---|---|---|---|
| 110 | I-40 | • 2 CF₃COOH<br><br>Biphenyl-2-ylcarbamic acid 1-(2-{[3-(4-{2-[(R)-2-hydroxy-2-(8-hydroxy-2-oxo-1,2-dihydroquinolin-5-yl)-ethylamino]propyl}phenylcarbamoyl)phenyl]methyl-carbamoyl}ethyl)piperidin-4-yl ester ditrifluoroacetic acid salt | 7 mg<br>Rt 3.06 min;<br>m/z 837.5 |
| 111 | I-41 | • 2 CF₃COOH<br><br>Biphenyl-2-ylcarbamic acid 1-(2-{[5-(4-{2-[(R)-2-hydroxy-2-(8-hydroxy-2-oxo-1,2-dihydroquinolin-5-yl)-ethylamino]propyl}phenylcarbamoyl)-2-methylphenyl]-methylcarbamoyl}ethyl)piperidin-4-yl ester | 13 mg<br>Rt 3.26 min;<br>m/z 851.3 |
| 112 | I-42 | • 2 CF₃COOH<br><br>Biphenyl-2-ylcarbamic acid 1-(2-{[3-(4-{(S)-2-[(R)-2-hydroxy-2-(8-hydroxy-2-oxo-1,2-dihydroquinolin-5-yl)-ethylamino]propyl}phenylcarbamoyl)phenyl]methyl-carbamoyl}ethyl)piperidin-4-yl ester ditrifluoroacetic acid salt | 5 mg<br>Rt 3.64 min;<br>m/z 837.6 |
| 113 | I-43 | • 2 CF₃COOH<br><br>Biphenyl-2-ylcarbamic acid 1-(2-{[3-(4-{(S)-2-[(R)-2-hydroxy-2-(8-hydroxy-2-oxo-1,2-dihydroquinolin-5-yl)-ethylamino]propyl}phenylcarbamoyl)phenyl]methyl-carbamoyl}ethyl)piperidin-4-yl ester ditrifluoroacetic acid salt | 39 mg<br>Rt 3.51 min;<br>m/z 837.5 |

| Ex. No. | ID No. | Compound | Amount/ LC-MS[1] |
|---|---|---|---|
| 114 | I-44 | Biphenyl-2-ylcarbamic acid 1-(2-{[3-(3-{2-[(R)-2-hydroxy-2-(8-hydroxy-2-oxo-1,2-dihydroquinolin-5-yl)-ethylamino]propyl}benzylcarbamoyl)phenyl]methyl-carbamoyl}ethyl)piperidin-4-yl ester ditrifluoroacetic acid salt •2 CF₃COOH | 11 mg Rt 3.20 min; m/z 851.5 |
| 115 | I-45 | Biphenyl-2-ylcarbamic acid 1-(2-{[5-(3-{2-[(R)-2-hydroxy-2-(8-hydroxy-2-oxo-1,2-dihydroquinolin-5-yl)-ethylamino]propyl}benzylcarbamoyl)-2-methylphenyl]-methylcarbamoyl}ethyl)piperidin-4-yl ester ditrifluoroacetic acid salt •2 CF₃COOH | 10 mg Rt 3.20 min; m/z 865.5 |
| 116 | I-46 | Biphenyl-2-ylcarbamic acid 1-(2-{[3-(4-{2-[(R)-2-hydroxy-2-(8-hydroxy-2-oxo-1,2-dihydroquinolin-5-yl)-ethylamino]propyl}benzylcarbamoyl)phenyl]methyl-carbamoyl}ethyl)piperidin-4-yl ester ditrifluoroacetic acid salt •2 CF₃COOH | 6 mg Rt 3.11 min; m/z 851.6 |
| 117 | I-47 | Biphenyl-2-ylcarbamic acid 1-(2-{[5-(4-{2-[(R)-2-hydroxy-2-(8-hydroxy-2-oxo-1,2-dihydroquinolin-5-yl)-ethylamino]propyl}benzylcarbamoyl)-2-methylphenyl]-methylcarbamoyl}ethyl)piperidin-4-yl ester ditrifluoroacetic acid salt •2 CF₃COOH | 19 mg Rt 3.30 min; m/z 865.7 |

TABLE II-continued

| Ex. ID No. | No. | Compound | Amount/ LC-MS[1] |
|---|---|---|---|
| 118 | I-48 | 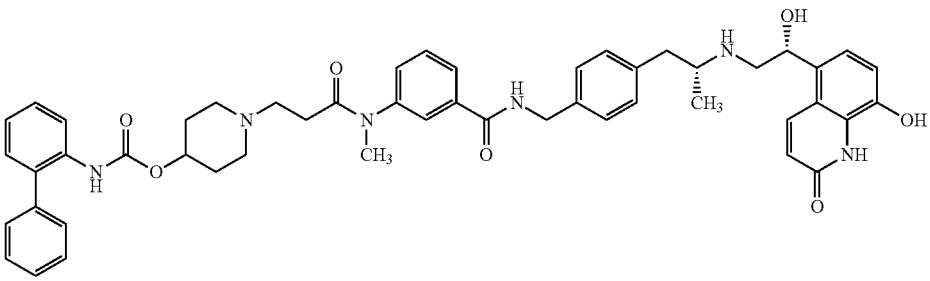<br>•2 CF₃COOH<br>Biphenyl-2-ylcarbamic acid 1-(2-{[3-(4-{(R)-2-[(R)-2-hydroxy-2-(8-hydroxy-2-oxo-1,2-dihydroquinolin-5-yl)-ethylamino]propyl}benzylcarbamoyl)phenyl]methyl-carbamoyl}ethyl)piperidin-4-yl ester ditrifluoroacetic acid salt | 41 mg Rt 3.47 min; m/z 851.5 |
| 119 | I-49 | 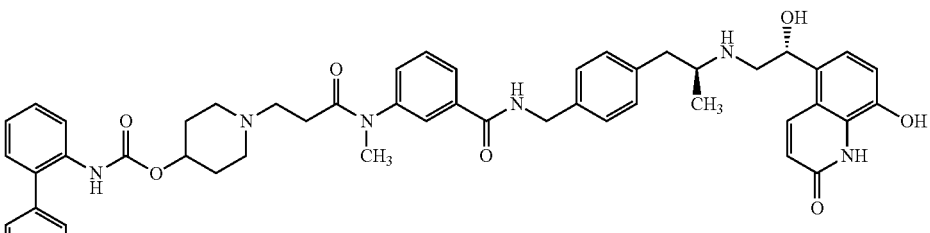<br>•2 CF₃COOH<br>Biphenyl-2-ylcarbamic acid 1-(2-{[3-(4-{(S)-2-[(R)-2-hydroxy-2-(8-hydroxy-2-oxo-1,2-dihydroquinolin-5-yl)-ethylamino]propyl}benzylcarbamoyl)phenyl]methyl-carbamoyl}ethyl)piperidin-4-yl ester ditrifluoroacetic acid salt | 108 mg Rt 3.58 min; m/z 851.6 |
| 120 | I-50 | 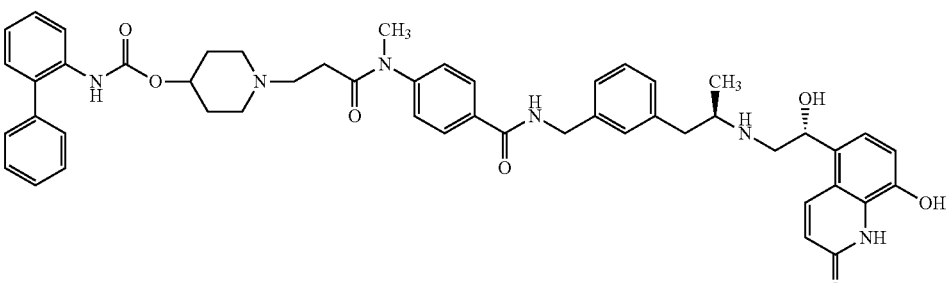<br>•2 CF₃COOH<br>Biphenyl-2-ylcarbamic acid 1-(2-{[4-(3-{(R)-2-[(R)-2-hydroxy-2-(8-hydroxy-2-oxo-1,2-dihydroquinolin-5-yl)-ethylamino]propyl}benzylcarbamoyl)phenyl]methyl-carbamoyl}ethyl)piperidin-4-yl ester ditrifluoroacetic acid salt | 6 mg Rt 2.35 min; m/z 851.4 |

TABLE II-continued

| Ex. No. | ID No. | Compound | Amount/ LC-MS[1] |
|---|---|---|---|
| 121 | I-51 | | 6 mg Rt 2.33 min; m/z 851.4 |

Biphenyl-2-ylcarbamic acid 1-(2-{[4-(3-{(S)-2-[(R)-2-hydroxy-2-(8-hydroxy-2-oxo-1,2-dihydroquinolin-5-yl)-ethylamino]propyl}benzylcarbamoyl)phenyl]methyl-carbamoyl}ethyl)piperidin-4-yl ester ditrifluoroacetic acid salt

| 122 | I-52 | | 11 mg Rt 3.31 min; m/z 851.6 |

Biphenyl-2-ylcarbamic acid 1-[2-({3-[2-(3-{2-[(R)-2-hydroxy-2-(8-hydroxy-2-oxo-1,2-dihydroquinolin-5-yl)-ethylamino]propyl}phenyl)acetylamino]phenyl}methyl-carbamoyl)ethyl]piperidin-4-yl ester ditrifluoroacetic acid salt

| 123 | I-53 | | 11 mg Rt 3.17 min; m/z 851.4 |

Biphenyl-2-ylcarbamic acid 1-[2-({3-[2-(4-{2-[(R)-2-hydroxy-2-(8-hydroxy-2-oxo-1,2-dihydroquinolin-5-yl)-ethylamino]propyl}phenyl)acetylamino]phenyl}methyl-carbamoyl)ethyl]piperidin-4-yl ester ditrifluoroacetic acid salt

| 124 | I-54 | | 15 mg Rt 3.32 min; m/z 881.6 |

Biphenyl-2-ylcarbamic acid 1-[2-({3-[2-(3-{2-[(R)-2-hydroxy-2-(8-hydroxy-2-oxo-1,2-dihydroquinolin-5-yl)-ethylamino]propyl}-4-methoxyphenyl)acetylamino]-phenyl}methylcarbamoyl)ethyl]piperidin-4-yl ester ditrifluoroacetic acid salt TABLE II-continued

| Ex. No. | ID No. | Compound | Amount/ LC-MS[1] |
|---|---|---|---|
| 125 | I-55 | 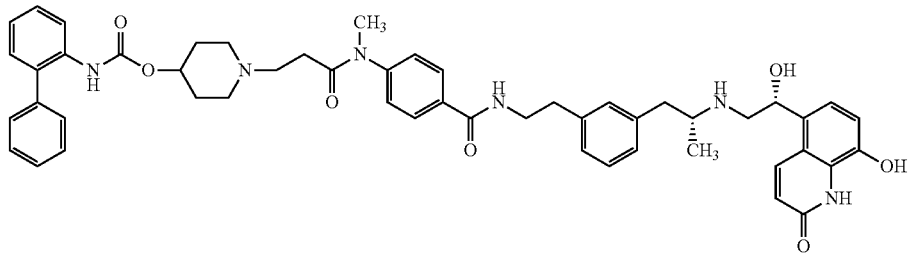  •2 CF$_3$COOH  Biphenyl-2-ylcarbamic acid 1-[2-({4-[2-(3-{(R)-2-[(R)-2-hydroxy-2-(8-hydroxy-2-oxo-1,2-dihydroquinolin-5-yl)-ethylamino]propyl}phenyl)ethylcarbamoyl]phenyl}-methylcarbamoyl)ethyl]piperidin-4-yl ester ditrifluoroacetic acid salt | 15 mg Rt 2.33 min; m/z 865.6 |
| 126 | I-56 | 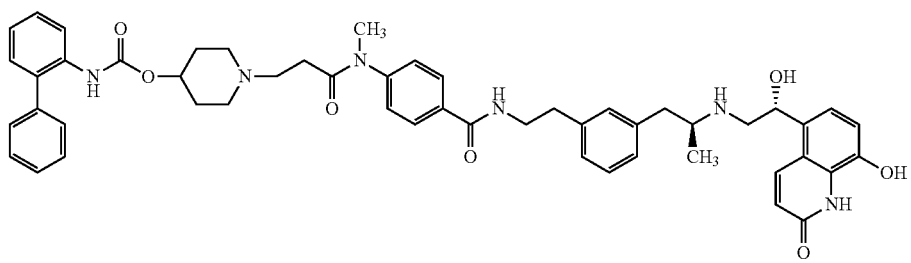  •2 CF$_3$COOH  Biphenyl-2-ylcarbamic acid 1-[2-({4-[2-(3-{(S)-2-[(R)-2-hydroxy-2-(8-hydroxy-2-oxo-1,2-dihydroquinolin-5-yl)-ethylamino]propyl}phenyl)ethylcarbamoyl]phenyl}-methylcarbamoyl)ethyl]piperidin-4-yl ester ditrifluoroacetic acid salt | 5 mg Rt 4.5 min; m/z 865.6 |
| 127 | I-57 | 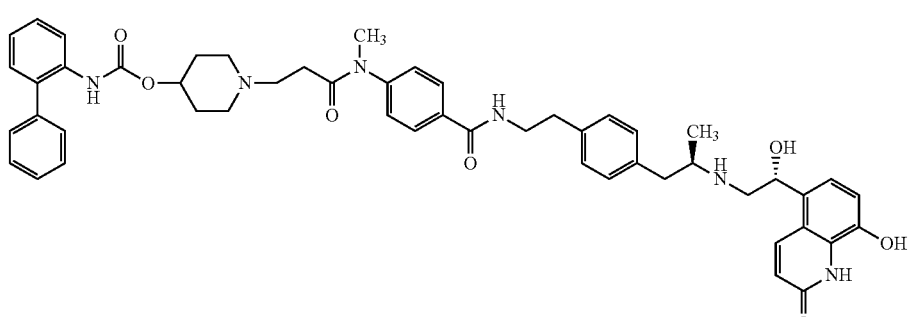  •2 CF$_3$COOH  Biphenyl-2-ylcarbamic acid 1-[2-({4-[2-(4-{(R)-2-[(R)-2-hydroxy-2-(8-hydroxy-2-oxo-1,2-dihydroquinolin-5-yl)-ethylamino]propyl}phenyl)ethylcarbamoyl]phenyl}-methylcarbamoyl)ethyl]piperidin-4-yl ester ditrifluoroacetic acid salt | 7 mg Rt 4.38 min; m/z 865.4 |

TABLE II-continued

| Ex. No. | ID No. | Compound | Amount/LC-MS[1] |
|---|---|---|---|
| 128 | I-58 | 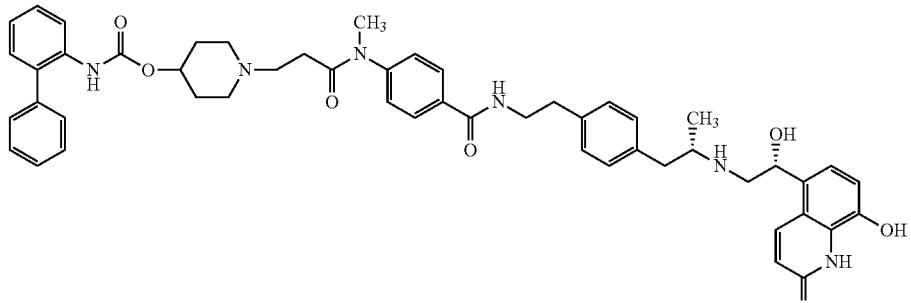•2 CF$_3$COOH<br>Biphenyl-2-ylcarbamic acid 1-[2-({4-[2-(4-{(S)-2-[(R)-2-hydroxy-2-(8-hydroxy-2-oxo-1,2-dihydroquinolin-5-yl)-ethylamino]propyl}phenyl)ethylcarbamoyl]phenyl}-methylcarbamoyl)ethyl]piperidin-4-yl ester ditrifluoroacetic acid salt | 4 mg<br>Rt 4.56 min;<br>m/z 865.5 |
| 129 | I-59 | 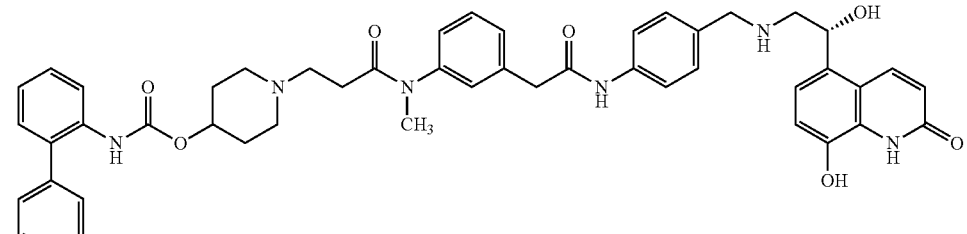•2 CF$_3$COOH<br>Biphenyl-2-ylcarbamic acid 1-[2-({3-[(4-{[(R)-2-hydroxy-2-(8-hydroxy-2-oxo-1,2-dihydroquinolin-5-yl)-ethylamino]methyl}phenylcarbamoyl)methyl]phenyl}-methylcarbamoyl)ethyl]piperidin-4-yl ester ditrifluoroacetic acid salt | 65 mg<br>Rt 2.02 min;<br>m/z 823.6 |
| 130 | I-60 | 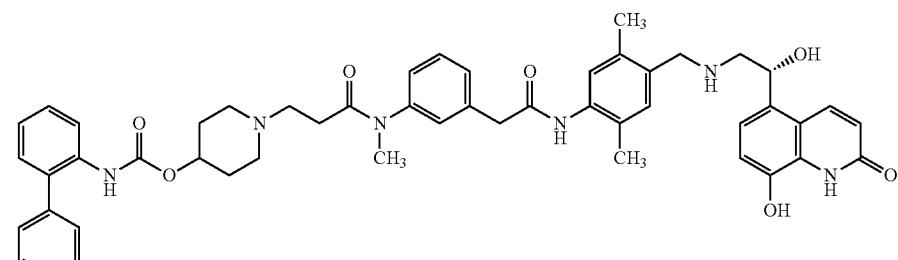•2 CF$_3$COOH<br>Biphenyl-2-ylcarbamic acid 1-[2-({3-[(4-{[(R)-2-hydroxy-2-(8-hydroxy-2-oxo-1,2-dihydroquinolin-5-yl)-ethylamino]methyl}-2,5-dimethylphenylcarbamoyl)-methyl]phenyl}methylcarbamoyl)ethyl]piperidin-4-yl ester ditrifluoroacetic acid salt | 28 mg<br>Rt 2.05 min;<br>m/z 851.6 |
| 131 | I-61 | 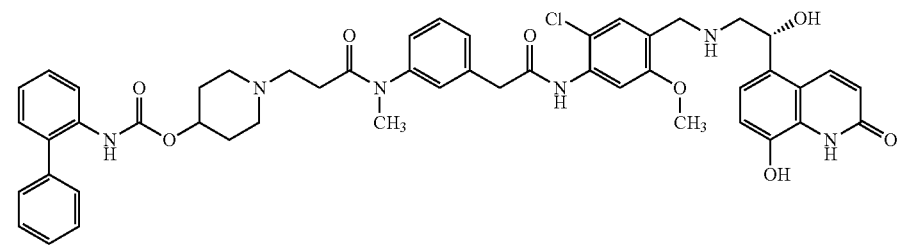•2 CF$_3$COOH<br>Biphenyl-2-ylcarbamic acid 1-[2-({3-[(2-chloro-4-{[(R)-2-hydroxy-2-(8-hydroxy-2-oxo-1,2-dihydroquinolin-5-yl)ethylamino]methyl}-5-methoxyphenylcarbamoyl)-methyl]phenyl}methylcarbamoyl)ethyl]piperidin-4-yl ester | 41 mg<br>Rt 2.32 min;<br>m/z 887.6 |

| Ex. ID No. | No. | Compound | Amount/ LC-MS[1] |
|---|---|---|---|
| 132 | I-62 | 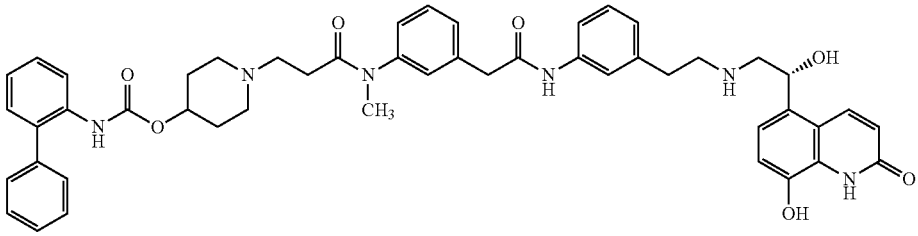<br>•2 CF₃COOH<br>Biphenyl-2-ylcarbamic acid 1-[2-({3-[(3-{2-[(R)-2-hydroxy-2-(8-hydroxy-2-oxo-1,2-dihydroquinolin-5-yl)-ethylamino]ethyl}phenylcarbamoyl)methyl]phenyl}-methylcarbamoyl)ethyl]piperidin-4-yl ester ditrifluoroacetic acid salt | 42 mg<br>Rt 2.05 min;<br>m/z 837.4 |
| 133 | I-63 | 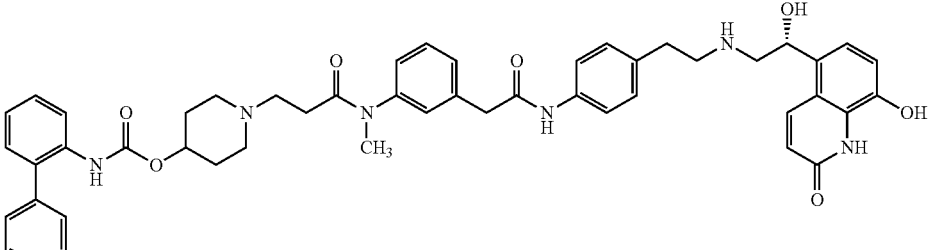<br>•2 CF₃COOH<br>Biphenyl-2-ylcarbamic acid 1-[2-({3-[(4-{2-[(R)-2-hydroxy-2-(8-hydroxy-2-oxo-1,2-dihydroquinolin-5-yl)-ethylamino]ethyl}phenylcarbamoyl)methyl]phenyl}-methylcarbamoyl)ethyl]piperidin-4-yl ester ditrifluoroacetic acid salt | 34 mg<br>Rt 2.02 min;<br>m/z 837.4 |
| 134 | I-64 | 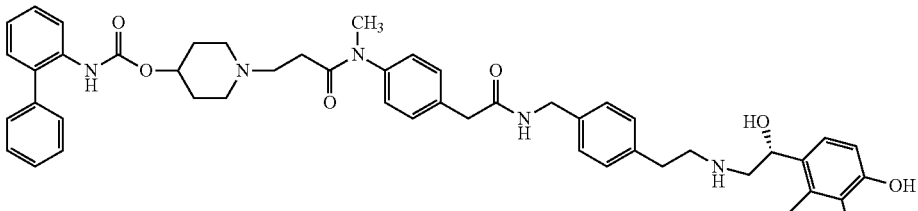<br>•2 CF₃COOH<br>Biphenyl-2-ylcarbamic acid 1-[2-({4-[(4-{2-[(R)-2-hydroxy-2-(8-hydroxy-2-oxo-1,2-dihydroquinolin-5-yl)-ethylamino]ethyl}benzylcarbamoyl)methyl]phenyl}-methylcarbamoyl)ethyl]piperidin-4-yl ester ditrifluoroacetic acid salt | na<br>Rt 2.29 min;<br>m/z 851.6 |
| 135 | I-65 | 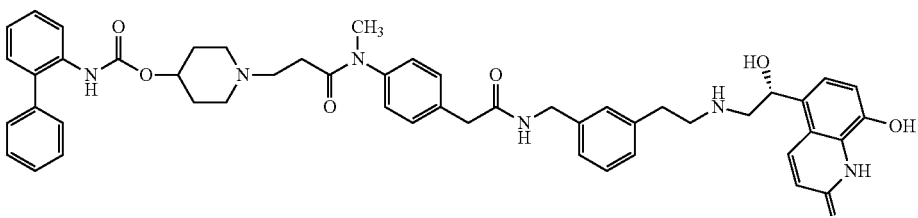<br>•2 CF₃COOH<br>Biphenyl-2-ylcarbamic acid 1-[2-({4-[(3-{2-[(R)-2-hydroxy-2-(8-hydroxy-2-oxo-1,2-dihydroquinolin-5-yl)-ethylamino]ethyl}benzylcarbamoyl)methyl]phenyl}-methylcarbamoyl)ethyl]piperidin-4-yl ester ditrifluoroacetic acid salt | 5 mg<br>Rt 2.33 min;<br>m/z 851.6 |

TABLE II-continued

| Ex. No. | ID No. | Compound | Amount/LC-MS[1] |
|---|---|---|---|
| 136 | I-66 | 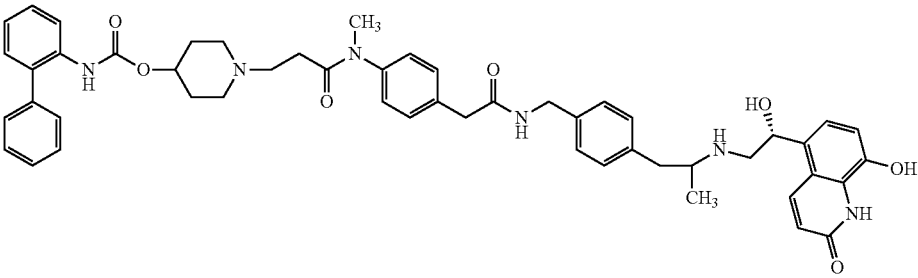 •2 CF$_3$COOH<br><br>Biphenyl-2-ylcarbamic acid 1-[2-({4-[(4-{2-[(R)-2-hydroxy-2-(8-hydroxy-2-oxo-1,2-dihydroquinolin-5-yl)-ethylamino]propyl}benzylcarbamoyl)methyl]phenyl}-methylcarbamoyl)ethyl]piperidin-4-yl ester ditrifluoroacetic acid salt | na<br>Rt 3.57 min;<br>m/z 865.7 |
| 137 | I-67 | 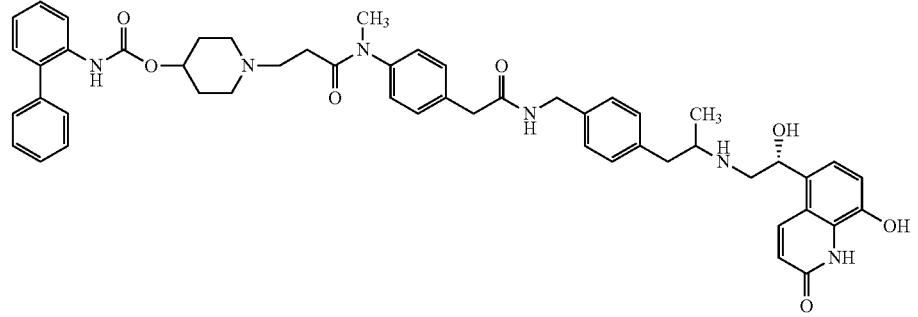 •2 CF$_3$COOH<br><br>Biphenyl-2-ylcarbamic acid 1-[2-({4-[(4-{2-[(R)-2-hydroxy-2-(8-hydroxy-2-oxo-1,2-dihydroquinolin-5-yl)-ethylamino]propyl}benzylcarbamoyl)methyl]phenyl}-methylcarbamoyl)ethyl]piperidin-4-yl ester ditrifluoroacetic acid salt | 15 mg<br>Rt 3.70 min;<br>m/z 865.4 |
| 138 | I-68 | 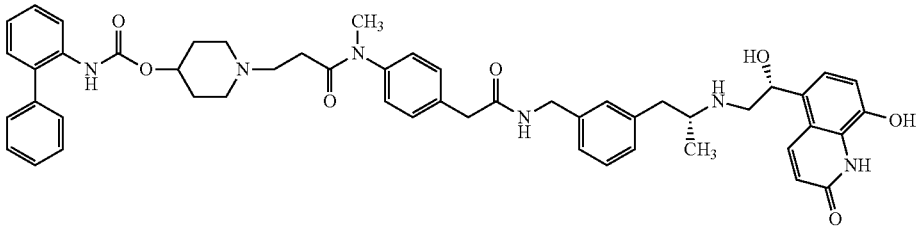 •2 CF$_3$COOH<br><br>Biphenyl-2-ylcarbamic acid 1-[2-({4-[(3-{(R)-2-[(R)-2-hydroxy-2-(8-hydroxy-2-oxo-1,2-dihydroquinolin-5-yl) ethylamino]propyl}benzylcarbamoyl)methyl]-phenyl}methylcarbamoyl)ethyl]piperidin-4-yl ester ditrifluoroacetic acid salt | 7 mg<br>Rt 4.41 min;<br>m/z 865.6 |
| 139 | I-69 | 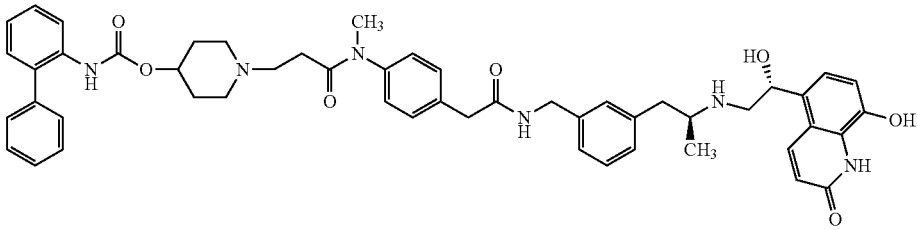 •2 CF$_3$COOH<br><br>Biphenyl-2-ylcarbamic acid 1-[2-({4-[(3-{(S)-2-[(R)-2-hydroxy-2-(8-hydroxy-2-oxo-1,2-dihydroquinolin-5-yl) ethylamino]propyl}benzylcarbamoyl)methyl]-phenyl}methylcarbamoyl)ethyl]piperidin-4-yl ester ditrifluoroacetic acid salt | 7 mg<br>Rt 4.50 min;<br>m/z 865.6 |

TABLE II-continued

| Ex. No. | ID No. | Compound | Amount/ LC-MS[1] |
|---|---|---|---|
| 140 | I-70 | 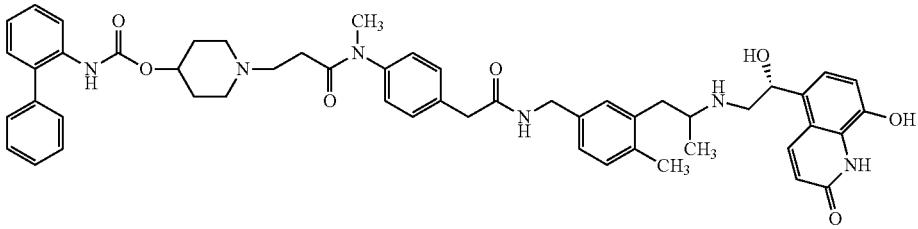<br>•2 CF₃COOH<br>Biphenyl-2-ylcarbamic acid 1-[2-({4-[(3-{2-[(R)-2-hydroxy-2-(8-hydroxy-2-oxo-1,2-dihydroquinolin-5-yl)-ethylamino]propyl}-4-methylbenzylcarbamoyl)methyl]-phenyl}methylcarbamoyl)ethyl]piperidin-4-yl ester ditrifluoroacetic acid salt | 2 mg<br>Rt 4.14 min;<br>m/z 879.6 |
| 141 | I-71 | 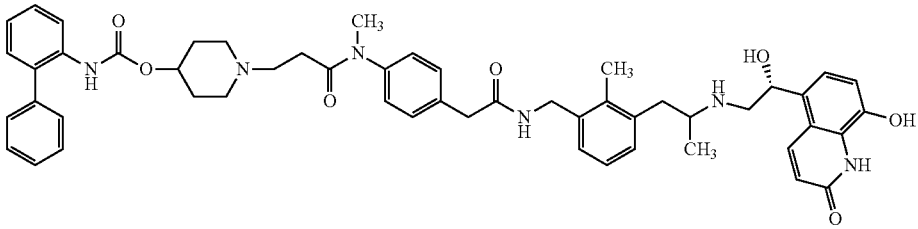<br>•2 CF₃COOH<br>Biphenyl-2-ylcarbamic acid 1-[2-({4-[(3-{2-[(R)-2-hydroxy-2-(8-hydroxy-2-oxo-1,2-dihydroquinolin-5-yl)-ethylamino]propyl}-2-methylbenzylcarbamoyl)methyl]-phenyl}methylcarbamoyl)ethyl]piperidin-4-yl ester ditrifluoroacetic acid salt | 5 mg<br>Rt 2.37 min;<br>m/z 879.6 |
| 142 | I-72 | 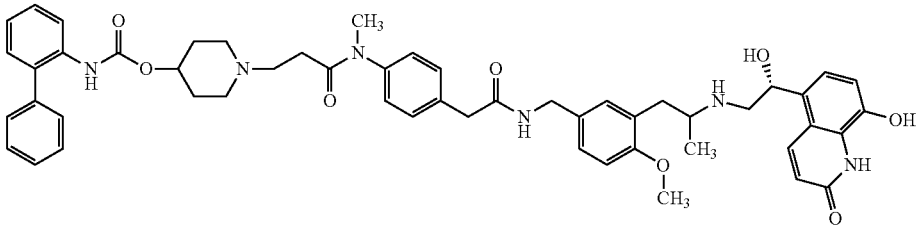<br>•2 CF₃COOH<br>Biphenyl-2-ylcarbamic acid 1-[2-({4-[(3-{2-[(R)-2-hydroxy-2-(8-hydroxy-2-oxo-1,2-dihydroquinolin-5-yl)-ethylamino]propyl}-4-methoxybenzylcarbamoyl)-methyl]phenyl}methylcarbamoyl)ethyl]piperidin-4-yl ester ditrifluoroacetic acid salt | 2 mg<br>Rt 4.24 min;<br>m/z 895.7 |
| 143 | I-73 | 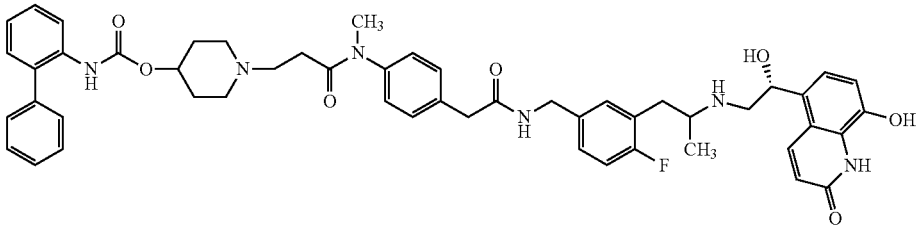<br>•2 CF₃COOH<br>Biphenyl-2-ylcarbamic acid 1-[2-({4-[(4-fluoro-3-{2-[(R)-2-hydroxy-2-(8-hydroxy-2-oxo-1,2-dihydroquinolin-5-yl)ethylamino]propyl}-benzylcarbamoyl)methyl]phenyl}methylcarbamoyl)-ethyl]piperidin-4-yl ester ditrifluoroacetic acid salt | 3 mg<br>Rt 4.14 min;<br>m/z 883.6 |

TABLE II-continued

| Ex. No. | ID No. | Compound | Amount/ LC-MS[1] |
|---|---|---|---|
| 144 | I-74 | 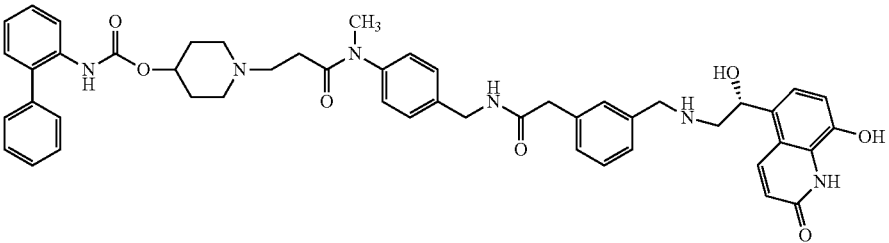  •2 CF₃COOH  Biphenyl-2-ylcarbamic acid 1-{2-[(4-{[2-(3-{[(R)-2-hydroxy-2-(8-hydroxy-2-oxo-1,2-dihydroquinolin-5-yl)-ethylamino]methyl}phenyl)acetylamino]methyl}-phenyl)methylcarbamoyl]ethyl}piperidin-4-yl ester ditrifluoroacetic acid salt | 15 mg Rt 3.23 min; m/z 837.5 |
| 145 | I-75 | 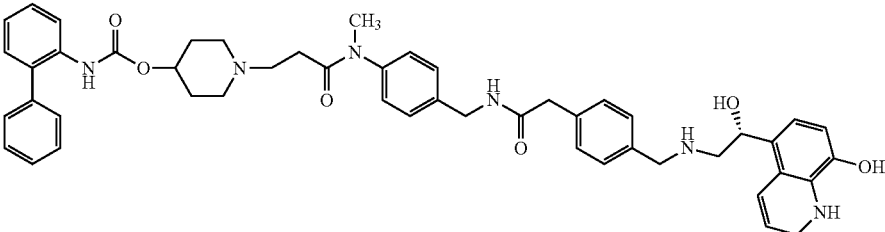  •2 CF₃COOH  Biphenyl-2-ylcarbamic acid 1-{2-[(4-{[2-(4-{[(R)-2-hydroxy-2-(8-hydroxy-2-oxo-1,2-dihydroquinolin-5-yl)-ethylamino]methyl}phenyl)acetylamino]methyl}-phenyl)methylcarbamoyl]ethyl)piperidin-4-yl ester ditrifluoroacetic acid salt | 10 mg Rt 3.63 min; m/z 837.5 |
| 146 | I-76 | 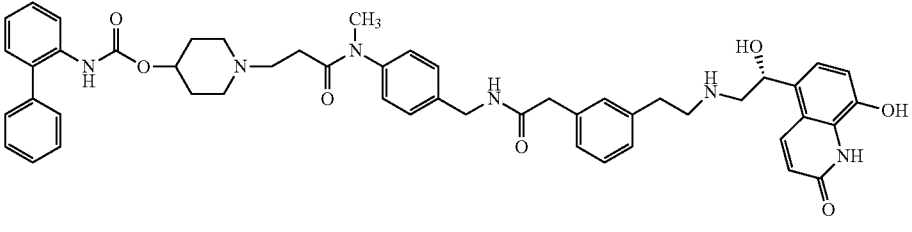  •2 CF₃COOH  Biphenyl-2-ylcarbamic acid 1-{2-[(4-{[2-(3-{2-[(R)-2-hydroxy-2-(8-hydroxy-2-oxo-1,2-dihydroquinolin-5-yl)-ethylamino]ethyl}phenyl)acetylamino]methyl}phenyl)-methylcarbamoyl]ethyl}piperidin-4-yl ester ditrifluoroacetic acid salt | 0.6 mg Rt 3.56 min; m/z 851.4 |
| 147 | I-77 | 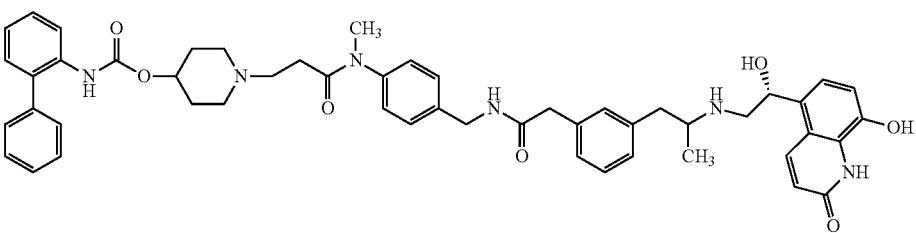  •2 CF₃COOH  Biphenyl-2-ylcarbamic acid 1-{2-[(4-{[2-(3-{2-[(R)-2-hydroxy-2-(8-hydroxy-2-oxo-1,2-dihydroquinolin-5-yl)-ethylamino]propyl}phenyl)acetylamino]methyl}-phenyl)methylcarbamoyl]ethyl}piperidin-4-yl ester ditrifluoroacetic acid salt | 15 mg Rt 4.31 min; m/z 865.3 |

TABLE II-continued

| Ex. No. | ID No. | Compound | Amount/ LC-MS[1] |
|---|---|---|---|
| 148 | I-78 | 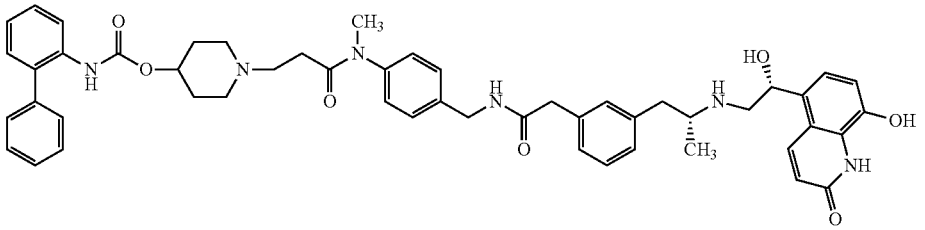  •2 CF$_3$COOH  Biphenyl-2-ylcarbamic acid 1-{2-[(4-{[2-(3-{(R)-2-[(R)-2-hydroxy-2-(8-hydroxy-2-oxo-1,2-dihydroquinalin-5-yl) ethylamino]propyl}phenyl)acetylamino]methyl}-phenyl)methylcarbamoyl]ethyl}piperidin-4-yl ester ditrifluoroacetic acid salt | 5 mg Rt 3.73 min; m/z 865.5 |
| 149 | I-79 | 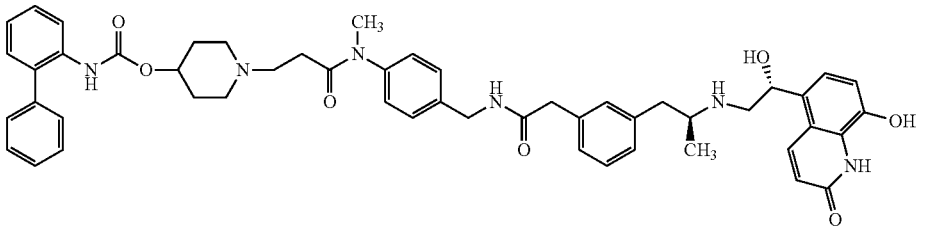  •2 CF$_3$COOH  Biphenyl-2-ylcarbamic acid 1-{2-[(4-{[2-(3-{(S)-2-[(R)-2-hydroxy-2-(8-hydroxy-2-oxo-1,2-dihydroquinolin-5-yl) ethylamino]propyl}phenyl)acetylamino]methyl}-phenyl)methylcarbamoyl]ethyl}piperidin-4-yl ester ditrifluoroacetic acid salt | 10 mg Rt 3.50 min; m/z 865.5 |
| 150 | I-80 | 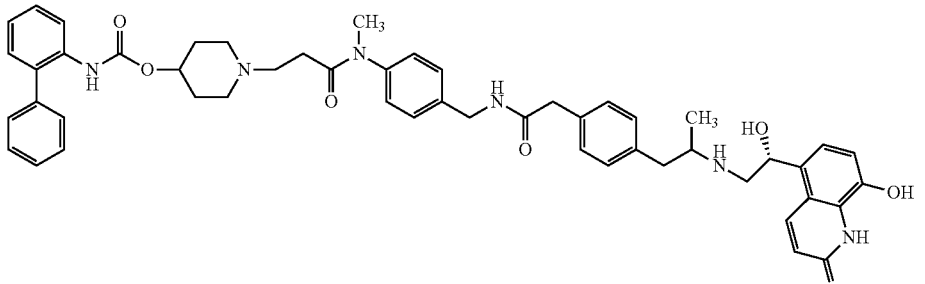  •2 CF$_3$COOH  Biphenyl-2-ylcarbamic acid 1-{2-[(4-{[2-(4-{2-[(R)-2-hydroxy-2-(8-hydroxy-2-oxo-1,2-dihydroquinolin-5-yl)- ethylamino]propyl}phenyl)acetylamino]methyl}-phenyl)methylcarbamoyl]ethyl}piperidin-4-yl ester ditrifluoroacetic acid salt | 10 mg |
| 151 | I-81 | 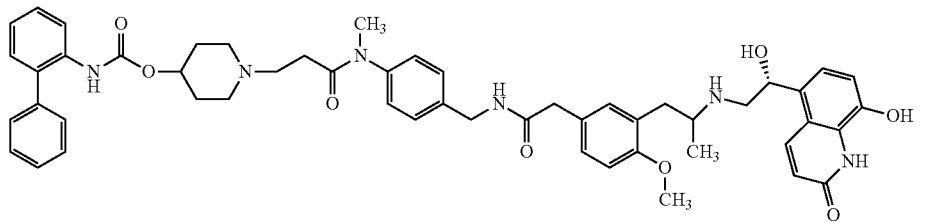  •2 CF$_3$COOH  Biphenyl-2-ylcarbamic acid 1-{2-[(4-{[2-(3-{2-[(R)-2-hydroxy-2-(8-hydroxy-2-oxo-1,2-dihydroquinolin-5-yl)- ethylamino]propyl}-4-methoxyphenyl)acetylamino]-methyl}phenyl)methylcarbamoyl]ethyl}piperidin-4-yl ester ditrifluoroacetic acid salt | 10 mg Rt 3.78 min; m/z 895.5 |

TABLE II-continued

| Ex. No. | ID No. | Compound | Amount/ LC-MS[1] |
|---|---|---|---|
| 152 | I-82 | •2 CF₃COOH<br>Biphenyl-2-ylcarbamic acid 1-{2-[(4-{[2-(3-{(R)-2-[(R)-2-hydroxy-2-(8-hydroxy-2-oxo-1,2-dihydroquinolin-5-yl) ethylamino]propyl}-4-methoxyphenyl)acetylamino]-methyl}phenyl)methylcarbamoyl]ethyl}piperidin-4-yl ester ditrifluoroacetic acid salt | 10 mg<br>Rt 3.78 min;<br>m/z 895.6 |
| 153 | I-83 | •2 CF₃COOH<br>Biphenyl-2-ylcarbamic acid 1-{2-[(4-{[2-(3-{(S)-2-[(R)-2-hydroxy-2-(8-hydroxy-2-oxo-1,2-dihydroquinalin-5-yl) ethylamino]propyl}-4-methoxyphenyl)acetylamino]-methyl}phenyl)methylcarbamoyl]ethyl}piperidin-4-yl ester ditrifluoroacetic acid salt | 5 mg<br>Rt 3.02 min;<br>m/z 895.6 |
| 154 | I-84 | •2 CF₃COOH<br>Biphenyl-2-ylcarbamic acid 1-{2-[(4-{[2-(4-fluoro-3-{2-[(R)-2-hydroxy-2-(8-hydroxy-2-oxo-1,2-dihydro-quinolin-5-yl)ethylamino]propyl}phenyl)acetylamino]-methyl}phenyl)methylcarbamoyl]ethyl}piperidin-4-yl ester ditrifluoroacctic acid salt | 15 mg<br>Rt 3.50 min;<br>m/z 883.6 |
| 155 | I-85 | •2 CF₃COOH<br>Biphenyl-2-ylcarbamic acid 1-{2-[(4-{[2-(3-{2-[(R)-2-hydroxy-2-(8-hydroxy-2-oxo-1,2-dihydroquinolin-5-yl)-ethylamino]propyl}phenyl)ethylcarbamoyl]methyl}-phenyl)methylcarbamoyl]ethyl}piperidin-4-yl ester ditrifluoroacetic acid salt | 7 mg<br>Rt 3.05 min;<br>m/z 879.8 |

| Ex. No. | ID No. | Compound | Amount/LC-MS[1] |
|---|---|---|---|
| 156 | I-86 | 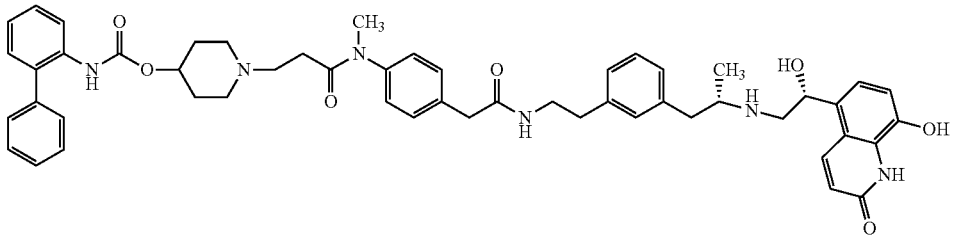<br>•2 CF$_3$COOH<br>Biphenyl-2-ylcarbamic acid 1-{2-[(4-{[2-(3-{(S)-2-[(R)-2-hydroxy-2-(8-hydroxy-2-oxo-1,2-dihydroquinolin-5-yl)-ethylamino]-propyl}-phenyl)ethylcarbamoyl]-methyl}phenyl)methylcarbamoyl]ethyl}piperidin-4-yl ester ditrifluoroacetic acid salt | 5 mg<br>Rt 4.45 min;<br>m/z 879.6 |
| 157 | I-88 | 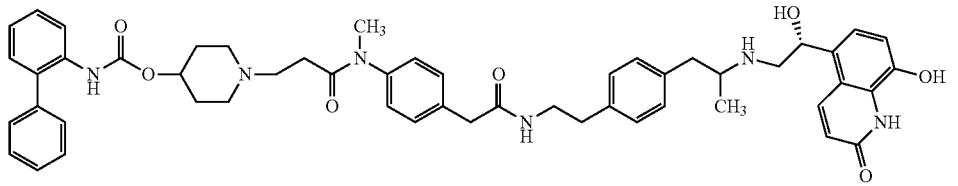<br>•2 CF$_3$COOH<br>Biphenyl-2-ylcarbamic acid 1-{2-[(4-{[2-(4-{2-[(R)-2-hydroxy-2-(8-hydroxy-2-oxo-1,2-dihydroquinolin-5-yl)-ethylamino]propyl}phenyl)ethylcarbamoyl]methyl}-phenyl)methylcarbamoyl]ethyl}piperidin-4-yl ester ditrifluoroacetic acid salt | 7 mg<br>Rt 3.03 min;<br>m/z 879.6 |
| 158 | I-89 | 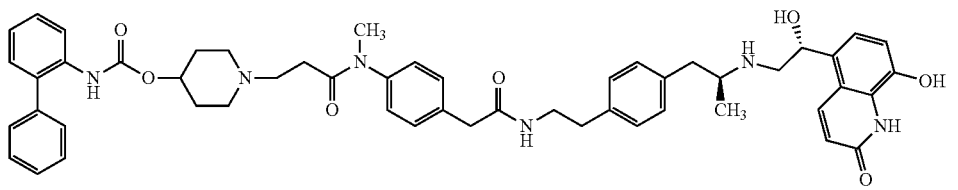<br>•2 CF$_3$COOH<br>Biphenyl-2-ylcarbamic acid 1-{2-[(4-{[2-(4-{(S)-2-[(R)-2-hydroxy-2-(8-hydroxy-2-oxo-1,2-dihydroquinolin-5-yl)ethylamino]propyl}phenyl)ethylcarbamoyl]methyl}-phenyl)methylcarbamoyl]ethyl}piperidin-4-yl ester ditrifluoroacetic acid salt | 8 mg<br>Rt 4.53 min;<br>m/z 879.5 |
| 159 | I-90 | 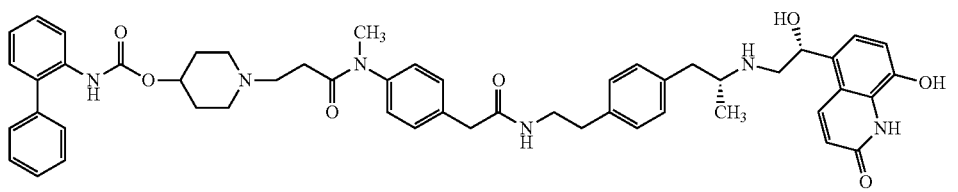<br>•2 CF$_3$COOH<br>Biphenyl-2-ylcarbamic acid 1-{2-[(4-{[2-(4-{(R)-2-[(R)-2-hydroxy-2-(8-hydroxy-2-oxo-1,2-dihydroquinolin-5-yl)ethylamino]propyl}phenyl)ethylcarbamoyl]methyl}-phenyl)methylcarbamoyl]ethyl}piperidin-4-yl ester ditrifluoroacetic acid salt | 10 mg<br>Rt 2.36 min;<br>m/z 879.6 |

TABLE II-continued

| Ex. ID No. | No. | Compound | Amount/ LC-MS[1] |
|---|---|---|---|
| 160 | I-91 | 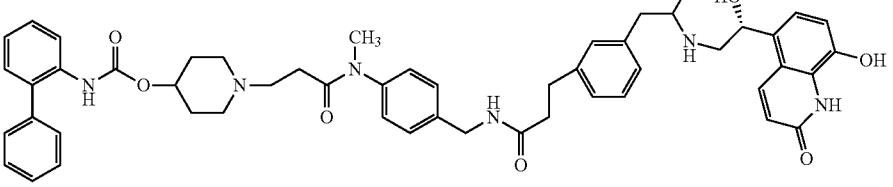 •2 CF$_3$COOH  Biphenyl-2-ylcarbamic acid 1-{2-[(4-{[3-(3-{2-[(R)-2-hydroxy-2-(8-hydroxy-2-oxo-1,2-dihydroquinolin-5-yl)-ethylamino]propyl}phenyl)propionylamino]methyl}-phenyl)methylcarbamoyl]ethyl}piperidin-4-yl ester ditrifluoroacetic acid salt | 20 mg Rt 3.61 min; m/z 879.6 |
| 161 | I-92 | 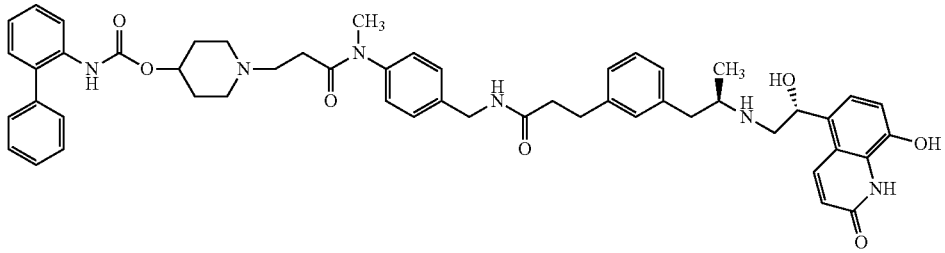 •2 CF$_3$COOH  Biphenyl-2-ylcarbamic acid 1-{2-[(4-{[3-(3-{(R)-2-[(R)-2-hydroxy-2-(8-hydroxy-2-oxo-1,2-dihydroquinolin-5-yl)ethylamino]propyl}phenyl)propionylamino]methyl}-phenyl)methylcarbamoyl]ethyl}piperidin-4-yl ester ditrifluoroacetic acid salt | 7 mg Rt 4.52 min; m/z 879.7 |
| 162 | I-93 | 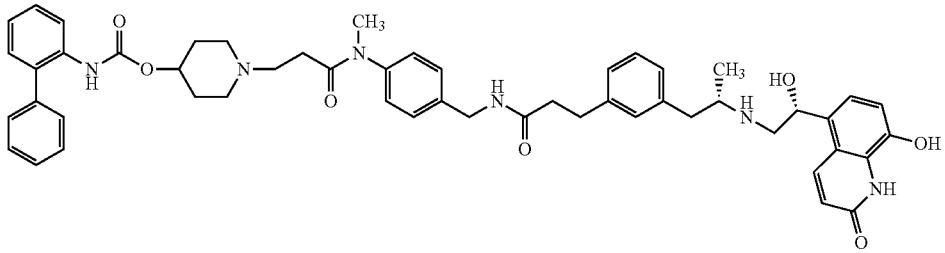 •2 CF$_3$COOH  Biphenyl-2-ylcarbamic acid 1-{2-[(4-{[3-(3-{(S)-2-[(R)-2-hydroxy-2-(8-hydroxy-2-oxo-1,2-dihydroquinolin-5-yl)ethylamino]propyl}phenyl)propionylamino]methyl}-phenyl)methylcarbamoyl]ethyl}piperidin-4-yl ester ditrifluoroacetic acid salt | 4 mg Rt 4.24 min; m/z 879.7 |
| 163 | I-94 | 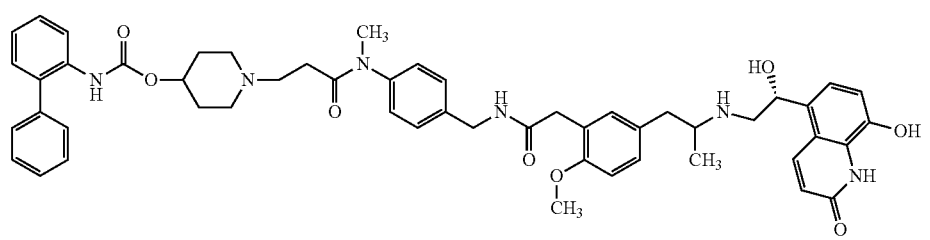 •2 CF$_3$COOH  Biphenyl-2-ylcarbamic acid 1-{2-[(4-{[2-(5-{2-[(R)-2-hydroxy-2-(8-hydroxy-2-oxo-1,2-dihydroquinolin-5-yl)-ethylamino]propyl}-2-methoxyphenyl)acetylamino]-methyl}phenyl)methylcarbamoyl]ethyl}piperidin-4-yl ester ditrifluoroacetic acid salt | 15 mg Rt 3.39 min; m/z 895.5 |

TABLE II-continued

| Ex. No. | ID No. | Compound | Amount/LC-MS[1] |
|---|---|---|---|
| 164 | I-95 | 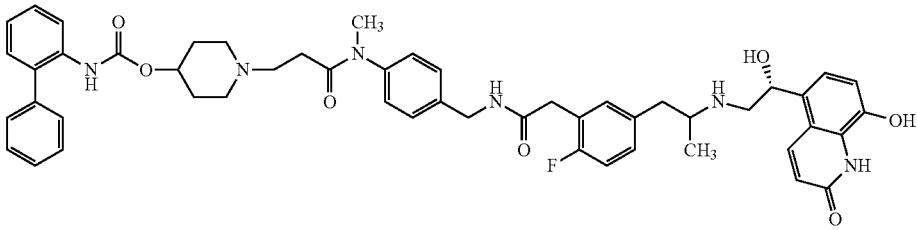•2 CF₃COOH<br><br>Biphenyl-2-ylcarbamic acid 1-{2-[(4-{[2-(2-fluoro-5-{2-[(R)-2-hydroxy-2-(8-hydroxy-2-oxo-1,2-dihydro-quinolin-5-yl)ethylamino]propyl}phenyl)-acetylamino]-methyl}phenyl)methylcarbamoyl]ethyl}piperidin-4-yl ester ditrifluoroacetic acid salt | 12 mg<br>Rt 4.10 min;<br>m/z 883.5 |
| 165 | I-96 | 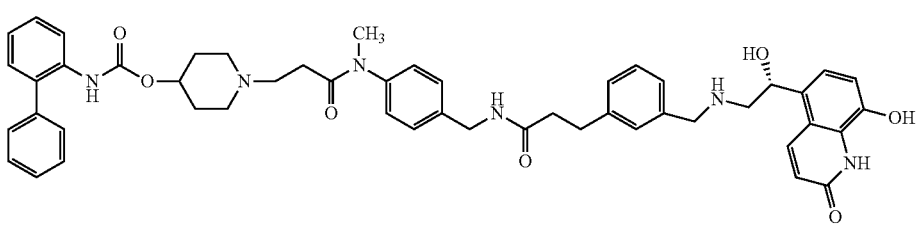•2 CF₃COOH<br><br>Biphenyl-2-ylcarbamic acid 1-{2-[(4-{[3-(3-{[(R)-2-hydroxy-2-(8-hydroxy-2-oxo-1,2-dihydroquinolin-5-yl)-ethylamino]methyl}phenyl)propionylamino]methyl}-phenyl)methylcarbamoyl]ethyl}piperidin-4-yl ester ditrifluoroacetic acid salt | 3 mg<br>Rt 4.34 min;<br>m/z 851.4 |

[1]Amount isolated (crude or pure) in milligrams;
Rt = retention time in minutes;
LC-MS: observed m/z, typically [M + H][1];
na = not available.

Biological Assays and Preparations

Example A

Cell Culture and Membrane Preparation from Cells Expressing Human $M_1$, $M_2$, $M_3$ and $M_4$ Muscarinic Receptors CHO cell lines stably expressing cloned human $hM_1$, $hM_2$, $hM_3$ and $hM_4$ muscarinic receptor subtypes, respectively, were grown to near confluency in Hams F-12 media supplemented with 10% FBS and 250 µg/mL Geneticin. The cells were grown in a 5% $CO_2$, 37° C. incubator and lifted with 2 mM EDTA in dPBS. Cells were collected by 5 minute centrifugation at 650×g, and cell pellets were either stored frozen at −80° C. or membranes were prepared immediately for use.

For membrane preparation, cell pellets were resuspended in lysis buffer and homogenized with a Polytron PT-2100 tissue disrupter (Kinematica AG; 20 seconds×2 bursts). Crude membranes were centrifuged at 40,000×g for 15 minutes at 4° C. The membrane pellet was then resuspended with re-suspension buffer and homogenized again with the Polytron tissue disrupter.

The protein concentration of the membrane suspension was determined by the method described in Lowry et al., 1951, *Journal of Biochemistry*, 193, 265. All membranes were stored frozen in aliquots at −80° C. or used immediately.

Aliquots of prepared $hM_5$ receptor membranes were purchased from PerkinElmer, Inc. (Wellesley, Mass.) and were stored at −80° C. until use.

Example B

Radioligand Binding Assay for Muscarinic Receptors

Radioligand binding assays for cloned muscarinic receptors were performed in 96-well microtiter plates in a total assay volume of 100 µL. CHO cell membranes stably expressing either the $hM_1$, $hM_2$, $hM_3$, $hM_4$ or $hM_5$ muscarinic subtype were diluted in assay buffer to the following specific target protein concentrations (µg/well): 10 µg for $hM_1$, 10-15 µg for $hM_2$, 10-20 µg for $hM_3$, 10-20 µg for $hM_4$, and 10-12 µg for $hM_5$ to get similar signals (cpm). The membranes were briefly homogenized using a Polytron tissue disruptor (10 seconds) prior to assay plate addition.

Saturation binding studies for determining $K_D$ values of the radioligand were performed using L-[N-methyl-$^3$H]scopolamine methyl chloride ([$^3$H]-NMS) (TRK666, 84.0 Ci/mmol, Amersham Pharmacia Biotech, Buckinghamshire, England) at concentrations ranging from 0.001 nM to 20 nM.

Displacement assays for determination of $K_i$ values of test compounds were performed with [$^3$H]-NMS at 1 nM and eleven different test compound concentrations. The test compounds were initially dissolved to a concentration of 400 µM in dilution buffer and then serially diluted 5× with dilution buffer to final concentrations ranging from 10 pM to 100 µM. The order of addition and volumes added to the assay plates were as follows: 25 µL radioligand, 25 µL diluted test compound, and 50 µL membranes. Assay plates were incubated for 6 hours at 37° C. Binding reactions were terminated by rapid filtration over GF/B glass fiber filter plates (PerkinElmer, Inc.) pre-treated in 1% BSA. Filter plates were rinsed three times with wash buffer (10 mM HEPES) to remove unbound radioactivity. The plates were then air-dried and 50 µL Microscint-20 liquid scintillation fluid (PerkinElmer, Inc.) were added to each well. The plates were then counted in a PerkinElmer Topcount liquid scintillation counter (PerkinElmer, Inc.).

Binding data were analyzed by nonlinear regression analysis with the GraphPad Prism Software package (GraphPad Software, Inc., San Diego, Calif.) using the one-site competition model. $K_i$ values for test compounds were calculated from observed $IC_{50}$ values and the $K_D$ value of the radioligand using the Cheng-Prusoff equation (Cheng Y; Prusoff W H. (1973) *Biochemical Pharmacology*, 22(23):3099-108). $K_i$ values were converted to $pK_i$ values to determine the geometric mean and 95% confidence intervals. These summary statistics were then converted back to $K_i$ values for data reporting.

In this assay, a lower $K_i$ value means the test compound has a higher binding affinity for the receptor. $hM_3$ receptor binding ($K_i$) data for compounds of this invention are shown in Table III.

Example C

Cell Culture and Membrane Preparation from Cells Expressing Human $\beta_1$, $\beta_2$ or $\beta_3$ Adrenergic Receptors Human embryonic kidney (HEK-293) cell lines stably expressing cloned human $\beta_1$ and $\beta_2$ adrenergic receptors or Chinese hamster ovarian (CHO) cell lines stably expressing cloned human $\beta_3$ adrenergic receptors were grown to near confluency in DMEM or Hams F-12 media with 10% FBS in the presence of 500 µg/mL Geneticin. The cell monolayer was lifted with 2 mM EDTA in PBS. Cells were pelleted by centrifugation at 1,000 rpm, and cell pellets were either stored frozen at −80° C. or membranes were prepared immediately for use.

For preparation of $\beta_1$ and $\beta_2$ receptor expressing membranes, cell pellets were re-suspended in lysis buffer (10 mM HEPES/HCl, 10 mM EDTA, pH 7.4 at 4° C.) and homogenized using a tight-fitting Dounce glass homogenizer (30 strokes) on ice.

For the more protease-sensitive $\beta_3$ receptor expressing membranes, cell pellets were homogenated in lysis buffer (10 mM Tris/HCl, pH 7.4) supplemented with one tablet of "Complete Protease Inhibitor Cocktail Tablets with 2 mM EDTA" per 50 mL buffer (Roche Molecular Biochemicals, Indianapolis, Ind.). The homogenate was centrifuged at 20,000×g, and the resulting pellet was washed once with lysis buffer by re-suspension and centrifugation as described herein. The final pellet was then re-suspended in ice-cold binding assay buffer (75 mM Tris/HCl pH 7.4, 12.5 mM $MgCl_2$, 1 mM EDTA).

The protein concentration of the membrane suspension was determined by the methods described in Lowry et al., 1951, *Journal of Biological Chemistry*, 193, 265; and Bradford, *Analytical Biochemistry*, 1976, 72, 248-54. All membranes were stored frozen in aliquots at −80° C. or used immediately.

Example D

Assay for Determining Adrenergic Receptor Agonist Potency cAMP assays were performed in a radioimmunoassay format using the Flashplate Adenylyl Cyclase Activation Assay System with [$^{125}$I]-cAMP (NEN SMP004, PerkinElmer Life Sciences Inc., Boston, Mass.), according to the manufacturers instructions. For this assay, HEK-293 cell lines stably expressing cloned human $\beta_1$ or $\beta_2$ receptors were grown to near confluency in DMEM supplemented with 10% FBS and Geneticin (500 µg/mL); or CHO-K1 cell lines stably expressing cloned human $\beta_3$ adrenergic receptors were grown to near confluency in Hams F-12 media supplemented with 10% FBS and Geneticin (250 µg/mL). Cells were rinsed with PBS and detached in dPBS (Dulbecco's Phosphate Buffered Saline, without $CaCl_2$ and $MgCl_2$) containing 2 mM EDTA or Trypsin-EDTA solution (0.05% trypsin/0.53 mM EDTA). After counting cells in Coulter cell counter, cells were pelleted by centrifugation at 1,000 rpm and re-suspended in stimulation buffer containing TBMX (PerkinElmer Kit) pre-warmed to room temperature to a concentration of $1.6\times10^6$ to $2.8\times10^6$ cells/mL. About 40,000 to 80,000 cells per well were used in this assay. Test compounds (10 mM in DMSO) were diluted into PBS containing 0.1% BSA in Beckman Biomek-2000 and tested at 11 different concentrations ranging from 100 µM to 1 pM. Reactions were incubated for 10 min at 37° C. and stopped by adding 100 µL of cold detection buffer containing [$^{125}$I]-cAMP (NEN SMP004, PerkinElmer Life Sciences, Boston, Mass.). The amount of cAMP produced (pmol/well) was calculated based on the counts observed for the samples and cAMP standards as described in the manufacturer's user manual.

Data were analyzed by nonlinear regression analysis with the GraphPad Prism Software package (GraphPad Software, Inc., San Diego, Calif.) with the sigmoidal equation. The Cheng-Prusoff equation (Cheng Y, and Prusoff W H., *Biochemical Pharmacology*, 1973, 22, 23, 3099-108) was used to calculate the $EC_{50}$ values.

In this assay, a lower $EC_{50}$ value means the test compound has a higher functional activity at the receptor tested. $h\beta_2$ efficacy ($EC_{50}$) data for compounds of this invention are shown in Table III.

Example E

Einthoven Assay

This assay measures the ability of a test compound to provide bronchoprotection against methacholine (MCh)-induced bronchoconstriction in a rat.

Male Sprague-Dawley rats (Harlan, Indianapolis, Ind.), weighing between 200 g and 350 g, were used for all studies.

Test compound or vehicle (sterile deionized water) were dosed by inhalation (1H) over a 10 min period in a pie shaped inhalation chamber (R+S Molds, San Carlos, Calif.) using 5 mL of dosing solution. Rats were exposed to an aerosol, which was generated from an LC Star Nebulizer Set Model 22F51 (PART Respiratory Equipment, Inc. Midlothian, Va.) driven by Bioblend (5% CO2/95% atmospheric air) at a pressure of 22 psi. Rats were dosed with 100 µg of test compound unless otherwise indicated.

At predetermined time points, rats were anesthetized with an intraperitoneal (IP) injection of 120 mg/kg inactin (thiobutabarbital). A supplemental dose (40 mg/kg, IP) was administered if the animal responded to physical stimuli (e.g. toe pinch). The surgical site was shaved and a 1-2 cm midline incision of the ventral aspect of the neck was made. The jugular vein was isolated and cannulated with a saline-filled polyethylene catheter (PE-50) to allow IV infusion of MCh. Trachea was dissected free and cannulated with a 14G needle (#NE-014, Small Parts, Miami Lakes, Fla.). After placement of the tracheal cannula, each rat was ventilated using a respirator (Model 683, Harvard Apparatus, Inc., MA) set at a stroke volume of 1 mL/100 g body weight (but not exceeding 2.5 mL volume) and a rate of 90 strokes per minute. A T-connector was placed along the respirator expiratory tubing to allow for measurement of changes in ventilation pressure (VP) using a Biopac transducer that was connected to a Biopac (TSD 137C) pre-amplifier. Body temperature was maintained at 37° C. using a heating pad.

Changes in VP were recorded using the Acknowledge Data Collection Software (Santa Barbara, Calif.). Baseline values were collected for at least 2.5 min. Rats were then challenged with non-cumulative intravenous (IV) infusions of 40 and 80 μg/kg MCh. MCh was infused intravenously for 2.5 minutes from a syringe pump (sp210iw, World Precision Instruments, Inc., Sarasota, Fla.) at a rate of 2 mL/kg/min, with a 2 minute interval between the two doses of MCh. Changes in ventilation pressure (cm $H_2O$) in treated animals are expressed as % inhibition of MCh response relative to control animals.

Other bronchoconstrictors, such as histamine and acetylcholine, can be used in place of MCh in this assay. Additionally, guinea pigs can be used instead of rats.

In this assay, a higher % inhibition of the MCh response indicates that the test compound provided a greater bronchoprotective effect. Inhibition greater than or equal to 30 percent at 24 h is indicative of a long duration of action. Bronchoprotection data for compounds of this invention are shown in Table III.

TABLE III

| ID No. | $hM_3$ $K_i$ (nM)[1] | $h\beta_2$ $EC_{50}$ (nM)[2] | Broncho. at 24 h[3] | ID No. | $hM_3$ $K_i$ (nM)[1] | $h\beta_2$ $EC_{50}$ (nM)[2] | Broncho. at 24 h[3] |
|---|---|---|---|---|---|---|---|
| I-1 | 0.1 | 3 | nd | I-2 | 0.1 | 1 | No |
| I-3 | 0.1 | 1 | Yes | I-4 | 0.1 | 2 | Yes |
| I-5 | 0.1 | 1 | Yes | I-6 | 0.1 | 1 | Yes |
| I-7 | 0.1 | 1 | Yes | I-8 | 0.1 | 1 | Yes |
| I-9 | 0.1 | 6 | nd | I-10 | 0.1 | 1 | Yes |
| I-11 | 0.1 | 1 | Yes | I-12 | 0.1 | 1 | No |
| I-13 | 0.1 | 1 | Yes | I-14 | 0.1 | 1 | Yes |
| I-15 | 0.1 | 1 | Yes | I-16 | 0.1 | 1 | Yes |
| I-17 | 0.1 | 1 | Yes | I-18 | 0.1 | 1 | Yes |
| I-19 | 0.1 | 1 | Yes | I-20 | 0.1 | 1 | Yes |
| I-21 | 0.1 | 1 | Yes | I-22 | 0.1 | 1 | Yes |
| I-23 | 0.1 | 1 | Yes | I-24 | 0.1 | 1 | Yes |
| I-25 | 0.1 | 1 | Yes | I-26 | 0.2 | 1 | Yes |
| I-27 | 0.1 | 1 | No | I-28 | 0.2 | 1 | No |
| I-29 | 0.1 | 1 | No | I-30 | 0.2 | 1 | No |
| I-31 | 0.2 | 1 | Yes | I-32 | 0.1 | 1 | No |
| I-33 | 0.2 | 1 | No | I-34 | 0.1 | 1 | Yes |
| I-35 | 0.2 | 1 | Yes | I-36 | 0.2 | 1 | Yes |
| I-37 | 0.2 | 1 | No | I-38 | 0.2 | 1 | No |
| I-39 | 0.2 | 1 | No | I-40 | 0.1 | 1 | Yes |
| I-41 | 0.3 | 1 | No | I-42 | 0.2 | 1 | No |
| I-43 | 0.1 | 1 | Yes | I-44 | 0.1 | 1 | No |
| I-45 | 0.2 | 1 | No | I-46 | 0.1 | 1 | Yes |
| I-47 | 0.2 | 3 | nd | I-48 | 0.3 | 1 | Yes |
| I-49 | 0.1 | 1 | Yes | I-50 | 0.4 | nd | nd |
| I-51 | 0.2 | 1 | nd | I-52 | 0.2 | 1 | No |
| I-53 | 0.1 | 1 | No | I-54 | 0.2 | 2 | nd |
| I-55 | 0.2 | 1 | Yes | I-56 | 0.2 | 1 | No |
| I-57 | 0.1 | 1 | nd | I-58 | 0.2 | 1 | nd |
| I-59 | 0.1 | 3 | nd | I-60 | 0.1 | 3 | nd |
| I-61 | 0.1 | 1 | Yes | I-62 | 0.1 | 1 | Yes |
| I-63 | 0.1 | 1 | nd | I-64 | 0.3 | 1 | No |
| I-65 | 0.1 | 1 | Yes | I-66 | 0.2 | 1 | No |
| I-67 | 0.1 | 1 | Yes | I-68 | 0.1 | 1 | Yes |
| I-69 | 0.1 | 1 | Yes | I-70 | 0.3 | 1 | nd |
| I-71 | 0.1 | 1 | nd | I-72 | 0.4 | 4 | nd |
| I-73 | 0.2 | 1 | nd | I-74 | 0.3 | 2 | nd |
| I-75 | 0.2 | 2 | nd | I-76 | 0.3 | 1 | nd |
| I-77 | 0.1 | 1 | Yes | I-78 | 0.3 | 1 | Yes |
| I-79 | 0.1 | 1 | No | I-80 | 0.2 | 1 | No |
| I-81 | 0.1 | 1 | Yes | I-82 | 0.1 | 1 | Yes |
| I-83 | 0.2 | 2 | Yes | I-84 | 0.1 | 1 | nd |
| I-85 | 0.2 | 2 | Yes | I-86 | 0.2 | 1 | Yes |
| I-87 | 0.1 | 1 | Yes | I-88 | 0.1 | 1 | Yes |
| I-89 | 0.1 | 1 | Yes | I-90 | 0.1 | 1 | nd |
| I-91 | 0.2 | 1 | Yes | I-92 | 0.2 | 1 | Yes |
| I-93 | 0.8 | 11 | nd | I-94 | 0.1 | 1 | Yes |
| I-95 | 0.2 | 1 | Yes | I-96 | 0.1 | 3 | nd | nd = not determined.

[1] $hM_3$ Muscarinic Receptor Binding ($K_i$) (data rounded to nearest 0.1 nM).
[2] $h\beta_2$ Adrenergic Receptor Agonist Potency ($EC_{50}$) (data rounded to nearest 1 nM),
[3] Bronchoprotective effect present at 24 h, e.g., ≥30% inhibition of the MCh response at 24 h in the rat Einthoven assay (100 μg).

The data in Table III demonstrate that all compounds tested had an hM₃ receptor binding (K$_i$) value in the range of from 0.1 nM to 0.8 nM. Moreover, all compounds tested had an hβ$_2$ efficacy (EC$_{50}$) value in the range of from 1 nM to 11 nM. Additionally, a majority of the compounds tested in the rat Einthoven Assay (using 100 1.1 g of test compound) provided a significant bronchoprotective effect (≥30% inhibition of MCh-induced bronchoconstriction) 24 hours after administration.

What is claimed is:

1. Biphenyl-2-ylcarbamic acid 1-(2-{[4-(4-{[(R)-2-hydroxy-2-(8-hydroxy-2-oxo-1,2-dihydroquinolin-5-yl)ethylamino]methyl}phenylcarbamoyl)-butyl]methylcarbamoyl}ethyl)piperidin-4-yl ester of the formula:

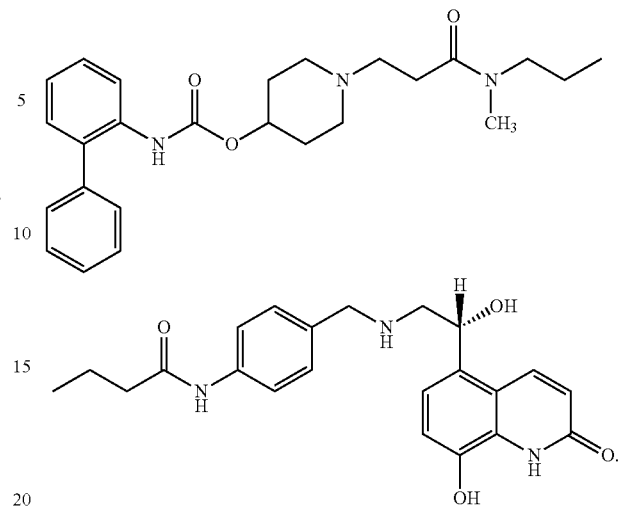

* * * * *